United States Patent
Gao et al.

(10) Patent No.: US 11,447,785 B2
(45) Date of Patent: Sep. 20, 2022

(54) METHOD FOR BASE EDITING IN PLANTS

(71) Applicant: Institute of Genetics and Developmental Biology, Chinese Academy of Sciences, Beijing (CN)

(72) Inventors: Caixia Gao, Beijing (CN); Yuan Zong, Beijing (CN)

(73) Assignee: Institute of Genetics and Developmental Biology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/347,932

(22) PCT Filed: Nov. 14, 2017

(86) PCT No.: PCT/CN2017/110841
§ 371 (c)(1),
(2) Date: May 7, 2019

(87) PCT Pub. No.: WO2018/086623
PCT Pub. Date: May 17, 2018

(65) Prior Publication Data
US 2019/0292553 A1    Sep. 26, 2019

(30) Foreign Application Priority Data

Nov. 14, 2016 (CN) .......................... 201610998842.X

(51) Int. Cl.
*C12N 15/82* (2006.01)
*C12N 9/22* (2006.01)
*C12N 9/78* (2006.01)

(52) U.S. Cl.
CPC ........... *C12N 15/8213* (2013.01); *C12N 9/22* (2013.01); *C12N 9/78* (2013.01); *C12N 15/8205* (2013.01); *C12N 15/8261* (2013.01); *C12N 15/8278* (2013.01); *C12N 15/8287* (2013.01); *C07K 2319/00* (2013.01); *C07K 2319/09* (2013.01); *C12N 2310/20* (2017.05); *C12N 2800/80* (2013.01); *C12Y 305/04005* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2015/0059010 A1* | 2/2015 | Cigan ................ | C12N 15/8213 800/260 |
| 2015/0071903 A1 | 3/2015 | Liu et al. | |
| 2015/0166980 A1* | 6/2015 | Liu ...................... | A61K 38/465 435/227 |
| 2017/0073670 A1* | 3/2017 | Nishida .............. | C12N 15/1024 |
| 2017/0121693 A1 | 5/2017 | Liu et al. | |

FOREIGN PATENT DOCUMENTS

| | | |
|---|---|---|
| CN | 105934516 A | 9/2016 |
| WO | 2015/089406 A1 | 6/2015 |
| WO | 2015/133554 A1 | 9/2015 |
| WO | 2015/189693 A1 | 12/2015 |
| WO | 2016183438 A1 | 11/2016 |
| WO | 2018/098935 A1 | 6/2018 |

OTHER PUBLICATIONS

Nishida et al 2016 (Science 353:6305) (Year: 2016).*
Yuan Zong et al., "Precise base editing in rice, wheat and maize with Cas9-cytidine deaminase fusion", Nature Biotechnology, vol. 35, No. 5, Feb. 27, 2017, pp. 1-4.
Alexis C. Komor et al., "Programmable editing of a target base in genomic DNA without double-stranded DNA cleavage", Nature, vol. 533, No. 7603, Apr. 20, 2016.
Yan Fang et al., "Overviews and applications of the CRISPR/Cas9 system in plant functional genomics and creation of new plant germplasm", Scientia Sinica Vitae, vol. 46, No. 5, May 25, 2016 pp. 498-513 (Abstract attached).
F. Ann Ran et al., "Double Nicking by RNA-Guided CRISPR Cas9 for Enhanced Genome Editing Specificity", Cell, vol. 154, No. 6, Aug. 29, 2013, pp. 1380-1389.
Written Opinion of the International Searching Authority for PCT/CN2017/110841 dated Feb. 9, 2018.
International Search Report for PCT/CN2017/110841 dated Feb. 23, 2018.
Nakamura st al., "Codon usage tabulated from the international DNA sequence databases: status for the year 2000", Nucleic Acids Research, vol. 28, No. 1, pp. 292, 2000, 3 pages.
Wang et al., "Simultaneous editing of three homoeoalleles in hexapioid bread wheat confers heritable resistance to powdery mildew", Nature Biotechnology, 2014, vol. 32, No. 9, pp. 947-951.
Shan et al., "Targeted genome modification of crop plants using a CRISPR-Cas system", Nature Biotechnology, 2013, vol. 31, No. 8, pp. 686-688.
Liang et al., "Targeted mutagenesis in *Zea mays* using TALENs and the CRISPR/Cas system", Journal of Genetics and Genomics, 2014, vol. 41, pp. 63-68.
Shan et al., "Genome editing in rice and wheat using the CRISPR/Cas system," Nature Protocols, 2014, vol. 9, No. 10, pp. 2395-2410.
Zhang et al., "Biolistic genetic transformation of a wide range of Chinese elite wheat (*Triticum aestivum* L.) varieties", Journal of Genetics and Genomics, 2015, vol. 42, pp. 39-42.

(Continued)

*Primary Examiner* — Matthew R Keogh
(74) *Attorney, Agent, or Firm* — Troutman Pepper Hamilton Sanders LLP

(57) ABSTRACT

The present invention belongs to the field of plant genetic engineering. Specifically, the invention relates to a method for base editing in plants. More particularly, the invention relates to a method for performing efficient base editing to a target sequence in the genome of a plant (such as a crop plant) by a Cas9-cytidine deaminase fusion protein, as well as plants produced through said method and progenies thereof.

12 Claims, 13 Drawing Sheets

Specification includes a Sequence Listing.

(56) References Cited

OTHER PUBLICATIONS

Osakabe et al., "Genome Editing with Engineered Nucleases in Plants", Plant & Cell Physiology, 2015, vol. 56, No. 3, pp. 389-400.
Pan et al., "CRISPR/Cas9-mediated efficient and heritable targeted mutagenesis in tomato plants in the first and later generations", Scientific Reports, 2016, vol. 6, 24765, 10 pages.
Database UniProt [Online] Nov. 2, 2016 (Nov. 2, 2016), "RecName: Full=Uracil-DNA glycosylase inhibitor;" XP002798018, retrieved from EBI accession No. UNIPROT:P14739 Database accession No. P14739.
Brooks et al., "Efficient Gene Editing in Tomato in the First Generation Using the Clustered Regularly Interspaced Short Palindromic Repeats/CRISPR-Associated9 System", Plant Physiology, 2014, vol. 166, pp. 1292-1297.
Takaori, "Antiviral defense by APOBEC3 Family Proteins", Viruses, 2005, vol. 55, No. 2, pp. 267-272.
Biochemistry, 2016, 88(5), pp. 555-556.
Japanese Office Action issued in JP 2019-505167 dated Oct. 5, 2020.
Lu et al., "Precise Editing of a Target Base in the Rice Genome Using a Modified CRISPR/Cas9 System", Molecular Plant, 2017, vol. 10, pp. 523-525.
Li et al., "Generation of Targeted Point Mutations in Rice by a Modified CRISPR/Cas9 System", Molecular Plant, 2017, vol. 10, pp. 526-529.
Li et al., "Generation of Targeted Point Mutations in Rice by a Modified CRISPR/Cas9 System", Molecular Plant, 2017, vol. 10, pp. 526-529, Supplementary Data.

* cited by examiner

|  | Thr | | | His → Tyr | | | Gly | | | Val | | | Gln | | | (SEQ ID NO: 223) |
|  | A | C | | C | A | | G | G | | G | T | G | C | A | G | (SEQ ID NO: 224) |
|---|---|---|---|---|---|---|---|---|---|---|---|---|---|---|---|---|
| Wheat | 0.0 | 0.0 | 3.56% | 3.78% | 0.0 | 6.45% | 0.0 | 0.0 | 6.47% | 0.0 | 0.0 | 0.0 | 0.0 | 0.0 | 0.0 | nCas9-PBE |
|  | 0.0 | 0.0 | 0.14% | 0.22% | 0.0 | 0.14% | 0.0 | 0.0 | 0.08% | 0.0 | 0.0 | 0.0 | 0.0 | 0.0 | 0.0 | dCas9-PBE |
| Rice | 0.0 | 0.0 | 2.48% | 3.79% | 0.0 | 5.86% | 0.0 | 0.0 | 6.85% | 0.0 | 0.0 | 0.0 | 0.0 | 0.0 | 0.0 | nCas9-PBE |
|  | 0.0 | 0.0 | 0.12% | 0.20% | 0.0 | 0.11% | 0.0 | 0.0 | 0.08% | 0.0 | 0.0 | 0.0 | 0.0 | 0.0 | 0.0 | dCas9-PBE |
| Maize | 0.0 | 0.0 | 3.92% | 3.06% | 0.0 | 8.75% | 0.0 | 0.0 | 7.56% | 0.0 | 0.0 | 0.0 | 0.0 | 0.0 | 0.0 | nCas9-PBE |
|  | 0.0 | 0.0 | 0.18% | 0.22% | 0.0 | 0.18% | 0.0 | 0.0 | 0.19% | 0.0 | 0.0 | 0.0 | 0.0 | 0.0 | 0.0 | dCas9-PBE |

FIG. 1D

| Target site | Total reads | Two Cs | | Three Cs | | Four Cs | | Five Cs | |
|---|---|---|---|---|---|---|---|---|---|
| | | Mutant reads | Mutagenesis frequency[a] | Mutant reads | Mutagenesis frequency[a] | Mutant reads | Mutagenesis frequency[a] | Mutant reads | Mutagenesis frequency[a] |
| sgRNA-TaLOX2-S1 | 127232 | 8783 | 6.90% | 4762 | 3.74% | -- | -- | -- | -- |
| sgRNA-TaLOX2-S2 | 139249 | 4763 | 3.42% | -- | -- | -- | -- | -- | -- |
| sgRNA-TaLOX2-S3 | 168509 | 21032 | 12.48% | 13936 | 8.27% | -- | -- | -- | -- |
| sgRNA-OsCDC48 | 235072 | 19632 | 8.35% | 7742 | 3.29% | 3784 | 1.61% | -- | -- |
| sgRNA-OsNRT1.1B | 212352 | 9723 | 4.58% | -- | -- | -- | -- | -- | -- |
| sgRNA-OsSPL14 | 201530 | 7073 | 3.51% | -- | -- | -- | -- | -- | -- |
| sgRNA-ZmCENH3 | 200897 | 8986 | 4.47% | 6876 | 3.42% | 1974 | 0.98% | 628 | 0.31% |

FIG. 2B

```
AtCENH3      THMLAP------PQINRWTAEALVALQEAAEDYLVGLFSDSMLCAIHA  155   (SEQ ID NO: 32)
HvβCENH3     ADNLTPLSNKKESKPTPWTPLALLSLQESAEYHLVDLFGKANLCAIHS  117   (SEQ ID NO: 33)
ZmCENH3      TNFVTN------GKVERYTAEALLALQEAAEFHLIELFEMANLCAIHA  135   (SEQ ID NO: 34)
ZmCENH3-AFL  TNFVTN------GKVERYTAEAFLALQEAAEFHLIELFEMANLCAIHA  135   (SEQ ID NO: 35)
ZmCENH3-VLL  TNFVTN------GKVERYTAEVLLALQEAAEFHLIELFEMANLCAIHA  135   (SEQ ID NO: 36)
ZmCENH3-ALF  TNFVTN------GKVERYTAEALFALQEAAEFHLIELFEMANLCAIHA  135   (SEQ ID NO: 37)
ZmCENH3-AFF  TNFVTN------GKVERYTAEAFFALQEAAEFHLIELFEMANLCAIHA  135   (SEQ ID NO: 38)
ZmCENH3-VFL  TNFVTN------GKVERYTAEVFLALQEAAEFHLIELFEMANLCAIHA  135   (SEQ ID NO: 39)
ZmCENH3-VLF  TNFVTN------GKVERYTAEVLFALQEAAEFHLIELFEMANLCAIHA  135   (SEQ ID NO: 40)
ZmCENH3-VFF  TNFVTN------GKVERYTAEVFFALQEAAEFHLIELFEMANLCAIHA  135   (SEQ ID NO: 41)
                               ***
```

FIG. 2D

```
WT:    ACCGAGTTTAGGTTCGCTGACCAGCCAGCGTCTGGCGCCGGCGCCGCCGCTGACCCCTT    (SEQ ID NO: 43)
T0-1:  ACCGAGTTTAGGTTCGCTGACtAGCCAGCGTCTGGCGCCGGCGCCGCCGCTGACCCCTT   (SEQ ID NO: 44)
T0-2:  ACCGAGTTTAGGTTCGCTGAttAGCCAGCGTCTGGCGCCGGCGCCGCCGCTGACCCCTT   (SEQ ID NO: 45)
T0-3:  ACCGAGTTTAGGTTCGCTGACCAGtCAGCGTCTGGCGCCGGCGCCGCCGCTGACCCCTT   (SEQ ID NO: 46)
T0-4:  ACCGAGTTTAGGTTCGCTGAtCAGCCAGCGTCTGGCGCCGGCGCCGCCGCTGACCCCTT   (SEQ ID NO: 47)
T0-5:  ACCGAGTTTAGGTTCGCTGACCAGtCAGCGTCTGGCGCCGGCGCCGCCGCTGACCCCTT   (SEQ ID NO: 48)
T0-6:  ACCGAGTTTAGGTTCGCTGACtAGCCAGCGTCTGGCGCCGGCGCCGCCGCTGACCCCTT   (SEQ ID NO: 49)
T0-7:  ACCGAGTTTAGGTTCGCTGACCAGtAGCGTCTGGCGCCGGCGCCGCCGCTGACCCCTT    (SEQ ID NO: 50)
T0-8:  ACCGAGTTTAGGTTCGCTGACtAGCCAGCGTCTGGCGCCGGCGCCGCCGCTGACCCCTT   (SEQ ID NO: 51)
T0-9:  ACCGAGTTTAGGTTCGCTGAttAGtCAGCGTCTGGCGCCGGCGCCGCCGCTGACCCCTT   (SEQ ID NO: 52)
T0-10: ACCGAGTTTAGGTTCGCTGACCAGCtAGCGTCTGGCGCCGGCGCCGCCGCTGACCCCTT   (SEQ ID NO: 53)
T0-11: ACCGAGTTTAGGTTCGCTGAttAGCCAGCGTCTGGCGCCGGCGCCGCCGCTGACCCCTT   (SEQ ID NO: 54)
T0-12: ACCGAGTTTAGGTTCGCTGACCAGtCAGCGTCTGGCGCCGGCGCCGCCGCTGACCCCTT   (SEQ ID NO: 55)
```

FIG. 4B

*ZmALS1/ZmALS2*

CAGGTGCCGCGACGCATGAT*TGG*  (SEQ ID NO: 56)

```
ZmALS1/ZmALS2-WT:  ccatcacgggaCAGGTGCCGCGACGCATGATTGGcaccgacgcc    (SEQ ID NO: 57)
ZmALS1/ZmALS2-T0-21:ccatcacgggaCAGGTGtCGCGACGCATGATTGGcaccgacgcc    (SEQ ID NO: 58)
      ZmALS1-T0-31:ccatcacgggaCAGGTGttGCGACGCATGATTGGcaccgacgcc    (SEQ ID NO: 59)
      ZmALS2-T0-31:ccatcacgggaCAGGTGCtGCGACGCATGATTGGcaccgacgcc    (SEQ ID NO: 60)
```

METHOD FOR BASE EDITING IN PLANTS

CROSS-REFERENCE TO RELATED APPLICATIONS

This application is a U.S. National Phase of International Patent Application No. PCT/CN2017/110841, filed Nov. 14, 2017, which claims priority to Chinese Patent Application No. 201610998842.X, filed Nov. 14, 2016, both of which applications are herein incorporated by reference in their entireties.

SEQUENCE LISTING

This application contains a Sequence Listing which has been submitted in ASCII format via EFS-Web and is hereby incorporated by reference in its entirety. Said ASCII copy, created on Jun. 30, 2020, is named 245761_000077_SL.txt, and is 196,250 bytes in size.

TECHNICAL FIELD

The present invention belongs to the field of plant genetic engineering. Specifically, the invention relates to a method for base editing in plants. More particularly, the invention relates to a method for performing efficient base editing to a target sequence in the genome of a plant (such as a crop plant) by a Cas9-cytidine deaminase fusion protein, as well as plants produced through said method and progenies thereof.

BACKGROUND

A prerequisite for efficient crop improvement is the availability of novel genetic mutations which can be easily incorporated into modern cultivars. Genetic researches, especially those whole genome related researches, indicate that single nucleotide alterations are the main reasons for the differences of traits in crops. Single nucleotide variation may lead to an amino acid substitution, and thereby lead to better alleles and traits. Before the advent of genome editing, Targeting Induced Local Lesions In Genomes (TILLING) can be used as the method for creating mutations much needed in crop improvement. However, TILLING screening is time consuming and costly, and the identified point mutations are often limited in both number and repertoire. Genome editing technologies, especially those based on the CRISPR/Cas9 system, make it possible to introduce particular base substitutions in specific genome sites through DNA repair mediated by homologous recombination (HR). But to date, the successful use of this method is greatly limited, most likely due to the low frequency of HR mediated double-strand break repair in plants. In addition, it is also a difficult task to effectively provide sufficient templates for DNA repair. These problems make it a big challenge to obtain targeted point mutations efficiently and easily through HR in plants. Therefore, there is still a strong need in the art for a new method of obtaining targeted point mutations in plant genome.

BRIEF DESCRIPTION OF THE INVENTION

In a first aspect, the invention provides a system for performing base editing to a target sequence in a plant genome, comprising at least one of the following (i) to (v):
i) a base editing fusion protein, and a guide RNA;
ii) an expression construct comprising a nucleotide sequence encoding a base editing fusion protein, and a guide RNA;
iii) a base editing fusion protein, and an expression construct comprising a nucleotide sequence encoding a guide RNA;
iv) an expression construct comprising a nucleotide sequence encoding a base editing fusion protein, and an expression construct comprising a nucleotide sequence encoding a guide RNA;
v) an expression construct comprising a nucleotide sequence encoding a base editing fusion protein and a nucleotide sequence encoding guide RNA;
wherein said base editing fusion protein comprises a nuclease-inactivated Cas9 domain and a deaminase domain, said guide RNA can target said base editing fusion protein to the target sequence in the plant genome.

In a second aspect, the invention provides a method of producing genetically modified plant, comprising the step of introducing a system for performing base editing to a target sequence in a plant genome of the invention into a plant, and thereby said base editing fusion protein is targeted to the target sequence in said plant genome by the guide RNA, and results in one or more C to T substitutions in said target sequence.

In a third aspect, the invention provides a genetically modified plant or progenies thereof, wherein said plant is obtained through the method of the invention.

In a fourth aspect, the invention provides a plant breeding method, comprising the step of crossing a first plant containing a genetic modification obtained through the method of the invention with a second plant that does not contain said genetic modification, and thereby introducing said genetic modification into said second plant.

DETAILED DESCRIPTION OF THE INVENTION

1. Definition

Figure 1A:
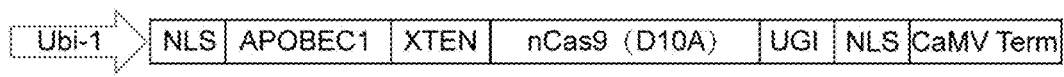
FIG. 1. Establishment of a targeted-Plant Base Editing (PBE) mediated genome editing system in plant protoplasts by a BFP-to-GFP reporter system. (a) Schematic representation of n/dCas9-PBE expression vectors. APOBEC1, n/dCas9, XTEN, and UGI are all codon-optimized for wheat, and NLS is attached to both ends of n/dCas9-PBE. The fusion protein is driven by a maize Ubiquitin-1 promoter. (b) Diagram of the BFP-to-GFP reporter system for detecting Targeted-PBE mediated precision genome editing in plant protoplasts. (c) Measurement of Targeted-PBE mediated BFP to GFP mutation efficiency in wheat and maize protoplasts by flow cytometry. Four fields of protoplasts are shown. Protoplasts were transformed with the following DNA constructs (from left to right): (i) pnCas9-PBE, pUbi-BFPm, and pBFP-sgRNA; (ii) pdCas9-PBE, pUbi-BFPm and pBFP-sgRNA; (iii) only pUbi-BFPm and BFP-sgRNA; (iv) positive control pUbi-GFP for GFP expression, which is driven by the maize Ubiquitin-1 promoter. Scale bars, 800 µm. (d) The genotype and frequency of BFP target site induced by Targeted-PBE system. In the sequence, the target base is C located at the fourth position. The number underneath represents the location thereof in the target sequence. Following each sequence are the percentages of the corresponding base relative to total sequencing reads. Three adjacent C (C3, C6, and C9) are also converted to T, but with no alteration to the protein sequence.
Figure 1A:
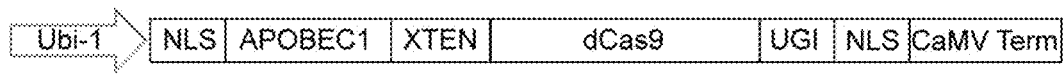
Figure 1A:
Figure 1A:

In the present invention, unless indicated otherwise, the scientific and technological terminologies used herein refer to meanings commonly understood by a person skilled in the art. Also, the terminologies and experimental procedures used herein relating to protein and nucleotide chemistry, molecular biology, cell and tissue cultivation, microbiology, immunology, all belong to terminologies and conventional methods generally used in the art. For example, the standard DNA recombination and molecular cloning technology used herein are well known to a person skilled in the art, and are described in details in the following references: Sambrook, J., Fritsch, E. F. and Maniatis, T., Molecular Cloning: A Laboratory Manual; Cold Spring Harbor Laboratory Press: Cold Spring Harbor, 1989 (hereinafter refers to as "Sambrook et al"). In the meantime, in order to better understand the present invention, definitions and explanations for the relevant terminologies are provided below.

"Cas9 nuclease" and "Cas9" can be used interchangeably herein, which refer to a RNA directed nuclease, including the Cas9 protein or fragments thereof (such as a protein comprising an active DNA cleavage domain of Cas9 and/or a gRNA binding domain of Cas9). Cas9 is a component of the CRISPR/Cas (clustered regularly interspaced short palindromic repeats and its associated system) genome editing system, which targets and cleaves a DNA target sequence to form a DNA double strand breaks (DSB) under the guidance of a guide RNA.

"guide RNA" and "gRNA" can be used interchangeably herein, which typically are composed of crRNA and tracrRNA molecules forming complexes through partial complement, wherein crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA.

"Deaminase" refers to an enzyme that catalyzes the deamination reaction. In some embodiments of the present invention, the deaminase refers to a cytidine deaminase, which catalyzes the deamination of a cytidine or a deoxycytidine to a uracil or a deoxyuridine, respectively.

"Genome" as it applies to plant cells encompasses not only chromosomal DNA found within the nucleus, but organelle DNA found within subcellular components (e.g., mitochondrial, plastid) of the cell.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast", as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

"Progeny" of a plant comprises any subsequent generation of the plant.

A "genetically modified plant" includes a plant which comprises within its genome an exogenous polynucleotide. For example, the exogenous polynucleotide is stably integrated within the genome such that the polynucleotide is passed on to successive generations. The exogenous polynucleotide may be integrated into the genome alone or as part of a recombinant DNA construct. The modified gene or expression regulatory sequence means that, in the plant genome, said sequence comprises one or more nucleotide substitution, deletion, or addition. For example, a genetically modified plant obtained by the present invention may contain one or more C to T substitutions relative to the wild type plant (corresponding plant that is not genetically modified).

The term "exogenous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

As used herein, an "expression construct" refers to a vector suitable for expression of a nucleotide sequence of interest in a plant, such as a recombinant vector. "Expression" refers to the production of a functional product. For example, the expression of a nucleotide sequence may refer to transcription of the nucleotide sequence (such as transcribe to produce an mRNA or a functional RNA) and/or translation of RNA into a protein precursor or a mature protein.

"Expression construct" of the invention may be a linear nucleic acid fragment, a circular plasmid, a viral vector, or, in some embodiments, an RNA that can be translated (such as an mRNA).

"Expression construct" of the invention may comprise regulatory sequences and nucleotide sequences of interest that are derived from different sources, or regulatory sequences and nucleotide sequences of interest derived from the same source, but arranged in a manner different than that normally found in nature.

"Regulatory sequence" or "regulatory element" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. A plant expression regulatory element refers to a nucleotide sequence capable of controlling the transcription, RNA processing or stability or translation of a nucleotide sequence of interest in a plant.

Regulatory sequences may include, but are not limited to, promoters, translation leader sequences, introns, and polyadenylation recognition sequences.

"Promoter" refers to a nucleic acid fragment capable of controlling transcription of another nucleic acid fragment. In some embodiments of the invention, the promoter is a promoter capable of controlling gene transcription in a plant cell whether or not its origin is from a plant cell. The promoter may be a constitutive promoter or a tissue-specific promoter or a developmentally regulated promoter or an inducible promoter.

"Constitutive promoter" refers to a promoter that generally causes gene expression in most cell types in most circumstances. "Tissue-specific promoter" and "tissue-preferred promoter" are used interchangeably, and refer to a promoter that is expressed predominantly but not necessarily exclusively in one tissue or organ, but that may also be expressed in one specific cell or cell type. "Developmentally regulated promoter" refers to a promoter whose activity is determined by developmental events. "Inducible promoter" selectively expresses a DNA sequence operably linked to it in response to an endogenous or exogenous stimulus (environment, hormones, or chemical signals, and so on).

As used herein, the term "operably linked" means that a regulatory element (for example but not limited to, a promoter sequence, a transcription termination sequence, and so on) is associated to a nucleic acid sequence (such as a coding sequence or an open reading frame), such that the transcription of the nucleotide sequence is controlled and regulated by the transcriptional regulatory element. Techniques for operably linking a regulatory element region to a nucleic acid molecule are known in the art.

"Introduction" of a nucleic acid molecule (such as a plasmid, a linear nucleic acid fragment, RNA, and so on) or protein into a plant means transforming the plant cell with the nucleic acid or protein so that the nucleic acid or protein can function in the plant cell. "Transformation" as used herein includes stable transformation and transient transformation.

"Stable transformation" refers to introducing an exogenous nucleotide sequence into a plant genome, resulting in genetically stable inheritance. Once stably transformed, the exogenous nucleic acid sequence is stably integrated into the genome of the plant and any successive generations thereof.

"Transient transformation" refers to introducing a nucleic acid molecule or protein into a plant cell, performing its function without stable inheritance. In transient transformation, the exogenous nucleic acid sequence is not integrated into the plant genome.

"Trait" refers to the physiological, morphological, biochemical, or physical characteristics of a plant or a particular plant material or cell. In some embodiments, the characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield. In some embodiments, trait also includes ploidy of a plant, such as haploidy which is important for plant breeding. In some embodiments, trait also includes resistance of a plant to herbicides.

"Agronomic trait" is a measurable parameter including but not limited to, leaf greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, disease resistance, cold resistance, salt tolerance, and tiller number and so on.

2. Base Editing System for Plants

The present invention provides a system for performing base editing to a target sequence in the genome of a plant, comprising at least one of the following (i) to (v):

i) a base editing fusion protein, and a guide RNA;

ii) an expression construct comprising a nucleotide sequence encoding a base editing fusion protein, and a guide RNA;

iii) a base editing fusion protein, and an expression construction comprising a nucleotide sequence encoding a guide RNA;

iv) an expression construct comprising a nucleotide sequence encoding a base editing fusion protein, and an expression construct comprising a nucleotide sequence encoding a guide RNA;

v) an expression construct comprising a nucleotide sequence encoding base editing fusion protein and a nucleotide sequence encoding guide RNA;

wherein said base editing fusion protein contains a nuclease-inactivated Cas9 domain and a deaminase domain, said guide RNA can target said base editing fusion protein to the target sequence in the plant genome.

The DNA cleavage domain of Cas9 nuclease is known to contain two subdomains: the HNH nuclease subdomain and the RuvC subdomain. HNH subdomains cleave the chain that is complementary to gRNA, whereas the RuvC subdomain cleaves the non-complementary chain. Mutations in these subdomains can inactivate Cas9 nuclease to form "nuclease-inactivated Cas9". The nuclease-inactivated Cas9 retains DNA binding capacity directed by gRNA. Thus, in principle, when fused with an additional protein, the nuclease-inactivated Cas9 can simply target said additional protein to almost any DNA sequence through co-expression with appropriate guide RNA.

Cytidine deaminase can catalyze the deamination of cytidine (C) in DNA to form uracil (U). If nuclease-inactivated Cas9 is fused with Cytidine deaminase, the fusion protein can target a target sequence in the genome of a plant through the direction of a guide RNA. The DNA double strand is not cleaved due to the loss of Cas9 nuclease activity, whereas the deaminase domain in the fusion protein is capable of converting the cytidine of the single-strand DNA produced during the formation of the Cas9-guide RNA-DNA complex into a U, and then C to T substitution may be achieved by base mismatch repair.

Therefore, in some embodiments of the invention, the deaminase is a cytidine deaminase, such as an apolipoprotein B mRNA editing complex (APOBEC) family deaminase. Particularly, the deaminase described herein is a deaminase that can accept single-strand DNA as the substrate.

Examples of cytidine deaminase can be used in the present invention include but are not limited to APOBEC1 deaminase, activation-induced cytidine deaminase (AID), APOBEC3G, or CDA1.

In some embodiments of the present invention, the cytidine deaminase comprises the amino acid sequence set forth in SEQ ID NO: 11.

The nuclease-inactivated Cas9 of the present invention can be derived from Cas9 of different species, for example, derived from S. pyogenes Cas9 (SpCas9, the nucleotide sequence of which is shown in SEQ ID NO: 18; the amino acid sequence is shown in SEQ ID NO: 21). Mutations in both the HNH nuclease subdomain and the RuvC subdomain of the SpCas9 (includes, for example, D10A and H840A mutations) inactivate S. pyogenes Cas9 nuclease, resulting in a nuclease dead Cas9 (dCas9). Inactivation of one of the subdomains by mutation allows Cas9 to gain nickase activity, i.e., resulting in a Cas9 nickase (nCas9), for example, nCas9 with a D10A mutation only.

Therefore, in some embodiments of the invention, the nuclease-inactivated Cas9 of the invention comprises amino acid substitutions D10A and/or H840A relative to wild-type Cas9.

In some preferred embodiments of the invention, the nuclease-inactivated Cas9 of the invention has nickase activity. Without being bound by any theory, it is believed that Eukaryotic mismatch repair uses nicks on a DNA strand for the removal and repair of the mismatched base in the DNA strand. The U: G mismatch formed by cytidine deaminase may be repaired into C: G. Through the introduction of a nick on the chain containing unedited G, it will be possible to preferentially repair the U: G mismatch to the desired U:A or T:A. Therefore, preferably, the nuclease-inactivated Cas9 is a Cas9 nickase that retains the cleavage activity of the HNH subdomain of Cas9, whereas the cleavage activity of the RuvC subdomain is inactivated. For example, the nuclease-inactivated Cas9 contains an amino acid substitution D10A relative to wild-type Cas9.

In some embodiments of the present invention, the nuclease-inactivated Cas9 comprises the amino acid sequence of SEQ ID NO:14. In some preferred embodiments, the nuclease-inactivated Cas9 comprises the amino acid sequence of SEQ ID NO: 13.

In some embodiments of the invention, the deaminase domain is fused to the N-terminus of the nuclease-inactivated Cas9 domain. In some embodiments, the deaminase domain is fused to the C-terminus of the nuclease-inactivated Cas9 domain.

In some embodiments of the invention, the deaminase domain and the nuclease inactivated Cas9 domain are fused through a linker. The linker can be a non-functional amino acid sequence having no secondary or higher structure, which is 1 to 50 (for example, 1, 2, 3, 4, 5, 6, 7, 8, 9, 10, 11, 12, 13, 14, 15, 16, 17, 18, 19, 20, or 20-25, 25-50) or more amino acids in length. For example, the linker may be a flexible linker, such as GGGGS (SEQ ID NO: 67), GS, GAP, (GGGGS)×3 (SEQ ID NO: 68), GGS, (GGS)×7 (SEQ ID NO: 69), and the like. In some preferred embodiments, the linker is an XTEN linker as shown in SEQ ID NO: 12.

In cells, uracil DNA glycosylase catalyzes the removal of U from DNA and initiates base excision repair (BER), which results in the repair of U: G to C: G Therefore, without any theoretical limitation, including uracil DNA glycosylase inhibitor in the base editing fusion protein of the invention or the system of the present invention will be able to increase the efficiency of base editing.

Accordingly, in some embodiments of the invention, the base editing fusion protein further comprises a uracil DNA glycosylase inhibitor (UGI). In some embodiments, the uracil DNA glycosylase inhibitor comprises the amino acid sequence set forth in SEQ ID NO: 15.

In some embodiments of the invention, the base editing fusion protein of the invention further comprises a nuclear localization sequence (NLS). In general, one or more NLSs in the base editing fusion protein should have sufficient strength to drive the accumulation of the base editing fusion protein in the nucleus of a plant cell in an amount sufficient for the base editing function. In general, the strength of the nuclear localization activity is determined by the number and position of NLSs, and one or more specific NLSs used in the base editing fusion protein, or a combination thereof.

In some embodiments of the present invention, the NLSs of the base editing fusion protein of the invention may be located at the N-terminus and/or the C-terminus. In some embodiments, the base editing fusion protein comprises about 1, 2, 3, 4, 5, 6, 7, 8, 9, 10, or more NLSs. In some embodiments, the base editing fusion protein comprises about 1, 2, 3, 4, 5, 6, 7, 8, 9, 10, or more NLSs at or near the N-terminus. In some embodiments, the base-editing fusion protein comprises about 1, 2, 3, 4, 5, 6, 7, 8, 9, 10, or more NLSs at or near the C-terminus. In some embodiments, the base editing fusion protein comprises a combination of these, such as one or more NLSs at the N-terminus and one or more NLSs at the C-terminus. Where there are more than one NLS, each NLS may be selected as independent from other NLSs. In some preferred embodiments of the invention, the base-editing fusion protein comprises two NLSs, for example, the two NLSs are located at the N-terminus and the C-terminus, respectively.

In general, NLS consists of one or more short sequences of positively charged lysine or arginine exposed on the surface of a protein, but other types of NLS are also known in the art. Non-limiting examples of NLSs include KKRKV (SEQ ID NO: 70)(nucleotide sequence 5'-AAGAAGAGAAAGGTC-3' (SEQ ID NO: 71)), PKKKRKV (SEQ ID NO: 30)(nucleotide sequence 5'-CCCAAGAAGAAGAGGAAGGTG-3' (SEQ ID NO: 72) or CCAAAGAAGAAGAGGAAGGTT (SEQ ID NO: 73)), or SGGSPKKKRKV (SEQ ID NO: 31)(nucleotide sequence 5'-TCGGGGGGGAGCCCAAAGAAGAAGCG-GAAGGTG-3' (SEQ ID NO: 74)).

In some embodiments of the invention, the N-terminus of the base editing fusion protein comprises an NLS with an amino acid sequence shown by PKKKRKV (SEQ ID NO: 30). In some embodiments of the invention, the C-terminus of the base-editing fusion protein comprises an NLS with an amino acid sequence shown by SGGSPKKKRKV (SEQ ID NO: 31).

In addition, the base editing fusion protein of the present invention may also include other localization sequences, such as cytoplasmic localization sequences, chloroplast localization sequences, mitochondrial localization sequences, and the like, depending on the location of the DNA to be edited.

In some embodiments of the present invention, the base editing fusion protein comprises the amino acid sequence set forth in SEQ ID NO: 22 or 23.

In order to obtain efficient expression in plants, in some embodiments of the invention, the nucleotide sequence encoding the base editing fusion protein is codon optimized for the plant to be base edited.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y, et al. "Codon usage tabulated from the international DNA sequence databases: status for the year 2000" Nucl. Acids Res. 28:292 (2000).

In some embodiments of the invention, the codon-optimized nucleotide sequence encoding the base editing fusion protein is set forth in SEQ ID NO: 19 or 20.

In some embodiments of the invention, the guide RNA is a single guide RNA (sgRNA). Methods of constructing suitable sgRNAs according to a given target sequence are known in the art. See e.g., Wang, Y. et al. Simultaneous editing of three homoeoalleles in hexaploid bread wheat confers heritable resistance to powdery mildew. *Nat. Biotechnol.* 32, 947-951 (2014); Shan, Q. et al. Targeted genome modification of crop plants using a CRISPR-Cas system. *Nat. Biotechnol.* 31, 686-688 (2013); Liang, Z. et al. Targeted mutagenesis in *Zea mays* using TALENs and the CRISPR/Cas system. *J Genet Genomics.* 41, 63-68 (2014).

In some embodiments of the invention, the nucleotide sequence encoding the base-edited fusion protein and/or the nucleotide sequence encoding the guide RNA is operably linked to a plant expression regulatory element, such as a promoter.

Examples of promoters that can be used in the present invention include but not limited to the cauliflower mosaic virus 35S promoter (Odell et al. (1985) *Nature* 313: 810-812), a maize Ubi-1 promoter, a wheat U6 promoter, a rice U3 promoter, a maize U3 promoter, a rice actin promoter, a TrpPro5 promoter (U.S. patent application Ser. No. 10/377,318; filed on Mar. 16, 2005), a pEMU promoter (Last et al. *Theor. Appl. Genet.* 81: 581-588), a MAS promoter (Velten et al. (1984) *EMBO J.* 3: 2723-2730), a maize H3 histone promoter (Lepetit et al. *Mol. Gen. Genet.* 231: 276-285 and Atanassova et al. (1992) *Plant J.* 2 (3): 291-300), and a *Brassica napus* ALS3 (PCT Application WO 97/41228) promoters. Promoters that can be used in the present invention also include the commonly used tissue specific promoters as reviewed in Moore et al. (2006) Plant J. 45 (4): 651-683.

3. The Method of Producing a Genetically Modified Plant

In another aspect, the present invention provides a method of producing a genetically modified plant, comprising introducing a system for performing base editing to a target sequence in a plant genome of the invention into a plant, and thereby said base editing fusion protein is targeted to the target sequence in said plant genome by the guide RNA, and results in one or more C to T substitutions in said target sequence.

The design of the target sequence that can be recognized and targeted by a Cas9 and guide RNA complex is within the technical skills of one of ordinary skill in the art. In general, the target sequence is a sequence that is complementary to a leader sequence of about 20 nucleotides comprised in guide RNA, and the 3'-end of which is immediately adjacent to the protospacer adjacent motif (PAM) NGG.

For example, in some embodiments of the invention, the target sequence has the structure: 5'-Nx-NGG-3', wherein N is selected independently from A, C, and T; X is an integer of 14≤X≤30; Nx represents X contiguous nucleotides, and NGG is a PAM sequence. In some specific embodiments of the invention, X is 20.

The base editing system of the present invention has a broad deamination window in plants, for example, a deamination window with a length of 7 nucleotides. In some embodiments of the methods of the invention, one or more C bases within positions 3 to 9 of the target sequence are substituted with Ts. For example, if present, any one, two, three, four, five, six, or seven Cs within positions 3 to 9 in the target sequence can be replaced with Ts. For example, if there are four Cs within positions 3 to 9 of the target sequence, any one, two, three, four Cs can be replaced by Ts. The C bases may be contiguous or separated by other nucleotides. Therefore, if there are multiple Cs in the target sequence, a variety of mutation combinations can be obtained by the method of the present invention. In some embodiments of the methods of the invention, further comprises screening plants having the desired nucleotide substitutions. Nucleotide substitutions in plants can be detected by T7EI, PCR/RE or sequencing methods, see e.g., Shan, Q., Wang, Y, Li, J. & Gao, C. Genome editing in rice and wheat using the CRISPR/Cas system. Nat. Protoc. 9, 2395-2410 (2014).

In the methods of the invention, the base editing system can be introduced into plants by various methods well known to people skilled in the art. Methods that can be used to introduce the base editing system of the present invention into plants include but not limited to particle bombardment, PEG-mediated protoplast transformation, *Agrobacterium*-mediated transformation, plant virus-mediated transformation, pollen tube approach, and ovary injection approach.

In the methods of the present invention, modification of the target sequence can be accomplished simply by introducing or producing the base editing fusion protein and guide RNA in plant cells, and the modification can be stably inherited without the need of stably transformation of plants with the base editing system. This avoids potential off-target effects of a stable base editing system, and also avoids the integration of exogenous nucleotide sequences into the plant genome, and thereby resulting in higher biosafety.

In some preferred embodiments, the introduction is performed in the absence of a selective pressure, thereby avoiding the integration of exogenous nucleotide sequences in the plant genome.

In some embodiments, the introduction comprises transforming the base editing system of the invention into isolated plant cells or tissues, and then regenerating the transformed plant cells or tissues into an intact plant. Preferably, the regeneration is performed in the absence of a selective pressure, i.e., no selective agent against the selective gene carried on the expression vector is used during the tissue culture. Without the use of a selective agent, the regeneration efficiency of the plant can be increased to obtain a modified plant that does not contain exogenous nucleotide sequences.

In other embodiments, the base editing system of the present invention can be transformed to a particular site on an intact plant, such as leaf, shoot tip, pollen tube, young ear, or hypocotyl. This is particularly suitable for the transformation of plants that are difficult to regenerate by tissue culture.

In some embodiments of the invention, proteins expressed in vitro and/or RNA molecules transcribed in vitro are directly transformed into the plant. The proteins and/or RNA molecules are capable of achieving base-editing in plant cells, and are subsequently degraded by the cells to avoid the integration of exogenous nucleotide sequences into the plant genome.

Plant that can be base-edited by the methods of the invention includes monocotyledon and dicotyledon. For example, the plant may be a crop plant such as wheat, rice, maize, soybean, sunflower, sorghum, rape, alfalfa, cotton, barley, millet, sugar cane, tomato, tobacco, cassava, or potato.

In some embodiments of the invention, the target sequence is associated with plant traits such as agronomic traits, and thereby the base editing results in the plant having altered traits relative to a wild type plant.

In the present invention, the target sequence to be modified may be located anywhere in the genome, for example, within a functional gene such as a protein-coding gene or, for example, may be located in a gene expression regulatory region such as a promoter region or an enhancer region, and thereby accomplish the functional modification of said gene or accomplish the modification of a gene expression. Accordingly, in some embodiments of the invention, C to T substitution(s) results in amino acid substitutions in a target protein or the truncation of a target protein (resulting in a stop codon). In other embodiments of the invention, C to T substitution(s) results in a change in the expression of a target gene.

In some embodiments, the gene modified by the methods of the invention can be wheat LOX2, rice CDC48, NRT1.1B and SPL14, maize CENH3, and ALS gene.

In some embodiments of the invention, the method further comprises obtaining progeny of the genetically modified plant.

In a further aspect, the invention also provides a genetically modified plant or progeny thereof or parts thereof, wherein the plant is obtained by the method of the invention described above.

In another aspect, the present invention also provides a plant breeding method comprising crossing a first genetically modified plant obtained by the above-mentioned method of the present invention with a second plant not containing said genetic modification, thereby introducing said genetic modification into said second plant.

4. Production Method of Maize Haploid Plants and the Use Thereof

CENH3 encodes centromeric histones, which are essential for the normal functioning of centromeres in animals and plants. TILLING studies have shown that amino acid substitutions of several residues in the C-terminal region of *Arabidopsis* CENH3 (AtCENH3) can result in haploid induction, which is advantageous for accelerating crop breeding. Substitution of a highly conserved leucine residue in the CENP-A targeting domain (CATD, FIG. 2d) of the plant CENH3 protein with a phenylalanine (F) results in a haploid induction in *Arabidopsis*, whereas in barley, although the loading of CENH3 into centromere is impaired, no haploid induction is occurred. The present inventors found that the mutation of the CATD domain in ZmCENH3 by the base editing method of the present invention, particularly the mutation of the conserved leucine residue, can be used for the induction of maize haploid, and can be widely used in the improvement of maize varieties.

The present invention provides a method of producing a maize haploid inducer line comprising modifying the ZmCENH3 gene in a maize plant by the base editing method of the invention, resulting in one or more amino acid substitutions in the CATD domain in ZmCENH3, the one or more amino acid substitutions confer a haploid inducer activity to the maize plant.

In a specific embodiment, the modification results in one or more amino acid substitutions in the conserved motif alanine-leucine-leucine (ALL) at positions 109-111 in ZmCENH3 of SEQ ID NO: 25. For example, the ALL motif is modified as single substitution: AFL, VLL, or ALF; double substitution: AFF, VFL, or VLF; or triple substitution: VFF.

In some embodiments, the target sequence for modification of ZmCENH3 by the base editing method of the invention is AGCCCTCCTTGCGCTGCAAG<u>AGG</u> (SEQ ID NO: 75), wherein the underlined sequence is a PAM sequence.

In some embodiments, the maize plant is a Zong31 variety. In some embodiments, the maize plant is a HiII variety.

The present invention provides a method of producing maize haploid comprising crossing a maize haploid inducer line obtained by the method of the present invention with a wild-type maize plant, and harvesting the hybrid progeny to obtain a maize haploid plant. In some embodiments, the maize haploid inducer line is used as a male parent and the wild-type maize plant is used as a maternal parent for cross.

The present invention also encompasses the maize haploid inducer line and the maize haploid plant obtained by the methods of the invention and their use in maize breeding.

5. Methods of Producing Herbicide-resistant Maize Plants

The present invention provides a method of producing a herbicide-resistant maize plant comprising modifying the ZmALS gene (encoding acetolactate synthase) in a maize plant by the base editing method of the invention, resulting in one or more amino acid substitutions in ZmALS, said one or more amino acid substitutions confer herbicide resistance to the maize plant.

In a specific embodiment, the modification simultaneously results in one or more amino acid substitutions of both ZmALS1 of SEQ ID NO: 27 and ZmALS2 of SEQ ID NO: 29. For example, the 165th residues of ZmALS1 and ZmALS2 are substituted.

In some embodiments, the target sequence for the modification of ZmALS1 and ZmALS2 by the base editing methods of the present invention is CAGGTGCCGCGACGCATGAT<u>TGG</u> (SEQ ID NO: 56), wherein the underlined sequence is a PAM sequence.

In some embodiments, the maize plant is a Zong31 variety. In some embodiments, the maize plant is a HiII variety.

The present invention also provides a method of breeding a herbicide-resistant maize plant, comprising crossing a first herbicide-resistant maize plant obtained by the above-described method of the present invention with a second plant so as to introduce the herbicide resistance into the second plant.

The present invention also encompasses herbicide-resistant maize plants or progeny thereof obtained by the methods of the invention.

A method of controlling undesired plants in a maize plant growing area, comprising applying an ALS inhibitor herbicide to the plants in the area, wherein the maize plant is a herbicide-resistant maize plant obtained by the method of the invention.

Examples

Materials and Methods

Construction of pn/dCas9-PBE Expression Vector

The APOBEC1, XTEN, nCas9(D10A), dCas9, and UGI sequences were codon-optimized for wheat (SEQ ID NO:1-5) and ordered from GenScript (Nanjing). The full length n/dCas9 fragment was amplified using the primer set AflII-F (with AflII restriction site) and MluI-R (with MluI restriction site). The PCR products were digested with AflII and MluI, and then inserted into the both enzymes-digested pUC57-APOBEC1-XTEN-UGI vector (the sequence of the vector is set forth in SEQ ID NO: 10) to generate the fusion cloning vector pUC57-APOBECI-XTEN-n/dCas9-UGI. Then the primer set BamHI-F and Bsp1047I-R was used to amplify the fragment of APOBECI-XTEN-n/dCas9-UGI. Products were digested with BamHI and Bsp1047I, and further inserted into BamHI and Bsp1047I-digested pUbi-GFP (the sequence of the vector is set forth in SEQ ID NO: 8) to generate the fusion expression vector pn/dCas9-PBE.

Construction of sgRNA Expression Vectors sgRNA target sequences in the experiment are shown in the Table 1 below:

TABLE 1

Target genes and gRNA target sequences

| sgRNA | SEQ ID NO:target sequence | SEQ ID NO:Oligo-F | SEQ ID NO:Oligo-R |
|---|---|---|---|
| sgRNA-OsBFPm | 77 ACCCACGGCGTGCAGTGCTTCGG | 84 GGCAACC-CACGG CGTGCAGTGCTT | 94 AAACAAGCACTG CACGCCGTGGGT |
| sgRNA-TaBFPm | 78 ACCCACGGCGTGCAGTGCTTCGG | 85 CTTGACC-CACGG CGTGCAGTGCTT | 94 AAACAAGCACTG CACGCCGTGGGT |
| sgRNA-ZmBFPm | 79 ACCCACGGCGTGCAGTGCTTCGG | 86 AGCAACC-CACGG CGTGCAGTGCTT | 94 AAACAAGCACTG CACGCCGTGGGT |
| sgRNA-OsCDC48 | 61 GACCAGCCAGCGTCTGGCGCCGG | 87 GGCA-GACCAGCC AGCGTCTGGCGC | 95 AAACGCGCCAGA CGCTGGCTGGTC |
| sgRNA-OsNRT1.1B | 80 CGGCGACGGCGAGCAAGTGGAGG | 88 GGCACGGCGACG GCGAGCAAGTGG | 96 AAACC-CACTTGC TCGCCGTCGCCG |
| sgRNA-OsSPL14 | 81 CTCTTCTGTCAACCCAGCCATGG | 89 GGCACTCTTCTG TCAACCCAGCCA | 97 AAACTGGCTGGG TTGACAGAAGAG |
| sgRNA-TaLOX2-S1 | 65 GTCGACATCAACAACCTCGACGG | 90 CTTGGTCGA-CAT CAACAACCTCGA | 98 AAACTCGAGGTT GTT-GATGTCGAC |
| sgRNA-TaLOX2-S2 | 82 CTTCCTGGGCTACACGCTCAAGG | 91 CTTGCTTCCTGG GCTA-CACGCTCA | 99 AAACT-GAGCGTG TAGCCCAG-GAAG |
| sgRNA-TaLOX2-S3 | 83 AAGGACCTCATCCCCATGGGCGG | 92 CTT-GAAGGACCT CATCCC-CATGGG | 100 AAACCC-CATGGG GAT-GAGGTCCTT |
| sgRNA-ZmCENH3 | 75 AGCCCTCCTTGCGCTGCAAGAGG | 93 AGCAAGCCCTCC TTGCGCTGCAAG | 101 AAACCTTGCAGC GCAAGGAGGGCT |

The italic Cs represent Cs to be mutated in the deamination window from positions 3-9; bold letters represents PAM sequence.

According to the previous description (Wang, Y. et al. Simultaneous editing of three homoeoalleles in hexaploid bread wheat confers heritable resistance to powdery mildew. *Nat. Biotechnol.* 32, 947-951, 2014; Shan, Q. et al. Targeted genome modification of crop plants using a CRISPR-Cas system. *Nat. Biotechnol.* 31, 686-688, 2013; and Liang, Z. et al. Targeted mutagenesis in *Zea mays* using TALENs and the CRISPR/Cas system. *J Genet Genomics.* 41, 63-68, 2014), sgRNA expression vectors were constructed based on pTaU6-sgRNA (Addgene ID53062), pOsU3-sgRNA (Addgene ID53063), or pZmU3-sgRNA (Addgene ID53061):

pTaU6-BFP-sgRNA, pOsU3-BFP-sgRNA, pZmU3-BFP-sgRNA, pTaU6-LOX2-S1-sgRNA, pTaU6-LOX2-S2-sgRNA, pTaU6-LOX2-S3-sgRNA, pOsU3-CDC48-sgRNA, pOsU3-NRT1.1-sgRNA, pOsU3-SPL14-sgRNA, and pZmU3-CENH3-sgRNA.

BFP and GFP Expression Vectors

The sequence of pUbi-BFPm is set forth in SEQ ID NO: 9. The amino acid sequence of BFP is set forth in SEQ ID NO: 17.

The sequence of pUbi-GFP is set forth in SEQ ID NO: 8. The amino acid sequence of GFP is set forth in SEQ ID NO: 16.

Construction of pAG-n/dCas9-PBE-CDC48-sgRNA Expression Vector

The APOBEC1-XTEN-d/nCas9-UGI fragment was fused to the StuI and SacI-digested pHUE411 (Addgen #62203) with primer set Gibson-F and Gibson-R through Gibson cloning method, generating the vector pHUE411-APOBEC1-XTEN-d/nCas9-UGI without sgRNA target sites. Paired oligonucleotides (oligos) comprising OsCDC48 targeting sequences were synthesized, annealed and cloned into BsaI-digested pHUN411 vector, obtaining the pHUE411-sgRNA-CDC48. Then the fragment resulted from the digestion of pHUE411-sgRNA-CDC48 with PmeI and AvrII was inserted into pHUE411-APOBEC-XTEN-d/nCas9-UGI which was also digested with PmeI and AvrII, to finally obtain the Agrobacterium-mediated transformation vector pAG-n/dCas9-PBE-CDC48-sgRNA.

Protoplast Assays

Wheat Bobwhite variety, rice Nipponbare, and maize inbred line variety Zong31 were used in this study. Protoplasts transformation is performed as described below. The average transformation efficiency is 55-70%. Transformation is carried out with 10 μg of each plasmid by PEG-mediated transfection. Protoplasts were collected after 48 h and DNA was extracted for T7E1 and PCR-RE assay.

Preparation and Transformation of Wheat (Maize) Protoplasts

1) The middle parts of wheat (maize) tender leaves were cut into strips of 0.5-1 mm in width. The strips were placed into 0.6M Mannitol solution for 10 minutes, filtered, and then placed in 50 ml enzyme solution 20-25° C. in darkness, with gently shaking (10 rmp) for 5 hours.

2) 10 ml W5 was added to dilute the enzymolysis products and the products were filtered with a 75 μm nylon filter in a round bottom centrifuge tube (50 ml).

3) 23° C. 100 g centrifugation for 3 min, and the supernatant was discarded.

4) The products were gently suspended with 10 ml W5, placed on the ice for 30 min to allow the protoplasts gradually settling, and the supernatant was discarded.

5) Protoplasts were suspended by adding an appropriate amount of MMG, placed on ice until transformation.

6) 10-20 μg plasmid, 200 μl protoplasts (about $4 \times 10^5$ cells), 220 μl fresh PEG solution were added into a 2 ml centrifuge tube, mixed up, and placed under room temperature in darkness for 10-20 minutes to induce transformation.

7) After the induction of transformation, 880 μl W5 solution was slowly added, and the tubes were gently turned upside down for mixing, then 100 g horizontal centrifuged for 3 min, and the supernatant was discarded.

8) The products were resuspended in 2 ml W5 solution, transferred to a six-well plate, cultivated under room temperature (or 25° C.) in darkness. For protoplast genomic DNA extraction, the products need to be cultivated for 48 h.

Preparation and Transformation of Rice Protoplast

1) Leaf sheath of the seedlings were used for protoplasts isolation, and cut into about 0.5 mm wide with a sharp blade.

2) Immediately after incision, transferred into 0.6M Mannitol solution, and placed in the dark for 10 min.

3) Mannitol solution was removed by filtration, and the products were transferred into enzymolysis solution, and evacuated for 30 min.

4) Enzymolysis was performed for 5-6 h in darkness with gently shaking (decolorization shaker, speed 10).

5) After enzymolysis completion, an equal volume of W5 was added, horizontal shake for 10 s to release protoplasts.

6) Protoplasts were filtered into a 50 ml round bottom centrifuge tube with a 40 μm nylon membrane and washed with W5 solution.

7) 250 g horizontal centrifugation for 3 min to precipitate the protoplasts, the supernatant was discarded.

8) Protoplasts were resuspended by adding 10 ml W5, and then centrifuged at 250 g for 3 min, and the supernatant was discarded.

9) An appropriate amount of MMG solution was added to resuspend the protoplasts to a concentration of $2 \times 10^6$/ml.

Note: All the above steps were carried out at room temperature.

10) 10-20 μg plasmid, 200 μl protoplasts (about $4 \times 10^5$ cells), and 220 μl fresh PEG solution were added into a 2 ml centrifugal tube, mixed, and placed at room temperature in darkness for 10-20 minutes to induce transformation.

11) After the completion of the transformation, 880 μl W5 solution was slowly added, and the tubes were gently turned upside down for mixing, 250 g horizontal centrifuged for 3 min, and the supernatant was discarded.

12) The products were resuspended in 2 ml WI solution, transferred to a six-well plate, cultivated in room temperature (or 25° C.) in darkness. For protoplast genomic DNA extraction, the products need to be cultivated for 48 h.

Transformation of DNA Constructs into Wheat Calli by Particle Bombardment

Plasmid DNA (pnCas9-PBE and pTaU6-LOX2-S1-sgRNA) was used to bombard Bobwhite immature embryos. Particle bombardment transformation was performed as described previously (Zhang, K., Liu, J., Zhang, Y, Yang, Z. & Gao, C. Biolistic genetic transformation of a wide range of Chinese elite wheat (*Triticum aestivum* L.) varieties. J. Genet Genomics 42, 39-42 (2015)). After bombardment, the embryos are treated according to the literature, but no selection agents were used during tissue culture.

Transformation of pAG-n/dCas9-PBE-CDC48-sgRNA into Rice Calli by Agrobacterium pAG-n/dCas9-PBE-CDC48-sgRNA binary vector was transformed into Agrobacterium AGL1 strain by electroporation. Agrobacterium-mediated transformation, tissue culture, and regeneration of rice Nipponbare were performed according to Shan et al. (Shan, Q. et al. Targeted genome modification of crop plants using a CRISPR-Cas system. *Nat. Biotechnol.* 31, 686-688 (2013)). Hygromycin (50 μg/ml) was used in all the subsequent tissue culture process for screen.

Identification of Mutations by T7EI and PCR/RE Assay

DNA from individual rice plant was extracted to detect the mutations by T7EI assay, and then mutations were confirmed by Sanger sequencing. In wheat, in order to save costs and labor, 3-4 plants were randomly selected as a group to detect mutations by T7EI and PCR/RE. Once a group showed a positive result, all the plants in the group were further tested by T7EI and PCR/RE, and then the results were confirmed by Sanger sequencing.

T7EI Detect Method:

1) Genomic DNA was extracted from a plant, amplified by PCR and detected by electrophoresis.

2) PCR products were added into T7EI buffer as follows:

| | |
|---|---|
| 10 × T7EI buffer | 1.1 μl |
| PCR product | 5 μl |
| ddH$_2$O | 4.4 μl |

3) The mixture was heated in the PCR device to 95° C. for 5 min, and then cooled to room temperature such that the PCR products re-anneal to form heteroduplex DNA.

4) T7EI endonuclease was added as follows:

| | |
|---|---|
| Anneal product in 3) | 10.5 μl |
| T7EI, 5 units/μl | 0.5 μl |
| Total volume | 11 μl |

5) 37° C. for 1 h, all 11 μl products was subjected to gel electrophoresis. Cleavage of the PCR products indicates that the products contain indel mutations.

PCR/RE:

1) Plant genomic DNA was extracted.

2) Fragments containing the target sites, the length of which is between 350-1000 bp, were amplified with synthetic gene-specific primers:

| | |
|---|---|
| 10 × EasyTaq Buffer | 5 μl |
| dNTP (2.5 mM) | 4 μl |
| Forward primer (10 μM) | 2 μl |
| Forward primer (10 μM) | 2 μl |
| Easy Taq | 0.5 μl |
| DNA | 2 μl |
| ddH$_2$O | To 50 μl |

3) The general reaction conditions are: denaturation at 94° C. for 5 min; denaturation at 94° C. for 30 s; anneal at 58° C. for 30 s, extension at 72° C. for 30 s, amplification for 30 to 35 cycles; incubation at 72° C. for 5 min; incubation at 12° C. 5 μl PCR products were subjected to electrophoresis.

4) PCR products were digested with restriction endonuclease as follows:

| | |
|---|---|
| 10 × Fastdigest Buffer | 2 μl |
| Restriction enzymes | 1 μl |
| PCR product | 3-5 μl |
| ddH₂O | To 20 μl |

5) Digestion at 37° C. for 2-3 h. Products were analyzed by 1.2% agarose gel electrophoresis.

6) The uncut mutant bands in the PCR products were recovered and purified, and subjected to TA cloning as follows:

| | |
|---|---|
| pEasy-T Vector | 1 μl |
| Recovered uncleaved PCR product | 4 μl |

7) The ligation was performed at 22° C. for 12 min. And the products were transformed into *E. coli* competent cells, which were then plated on LB plates (Amp100, IPTG, and X-gal), incubated at 22° C. for 12-16 h. White colonies were picked for identifying positive clones and sequencing.

In-Depth Sequencing

Different sgRNA expression vectors in combination with pnCas9-PBE, pdCas9-PBE, and pwCas9 respectively were transformed into wheat, rice, or maize protoplasts for 48 hours. After that, protoplasts were collected and DNA was extracted for in-depth sequencing. In the first round of PCRs, the target regions were amplified with site-specific primers (Table 5). In the second round of PCRs, forward and reverse tags were added to the end of the PCR products for library construction (Table 5). Equal amount of different PCR products were pooled. The samples were then sequenced with Illumina High-Seq 4000 at Beijing Genomics Institute.

Example 1. Base Editing of BFP in Plant Protoplasts by nCas9-PBE and dCas9-PBE

In the nCas9-PBE fusion protein, from N-terminal to C-terminal are NLD (SEQ ID NO: 30), APOBEC1 (SEQ ID NO: 11), XTEN linker (SEQ ID NO: 12), Cas9 nickase (nCas9, SEQ ID NO: 13), uracil DNA glycosylase inhibitors (UGI, SEQ ID NO: 15) and NLS (SEQ ID NO: 31) respectively; whereas in the dCas9-PBE fusion protein, from N-terminal to C-terminal are NLS, APOBEC1, XTEN linkers, catalytically deactivated Cas9 (dCas9, SEQ ID NO: 14), UGI, and NLS, respectively. Codon-optimized fusion protein coding sequences for efficient expression in cereal crops were placed downstream of the Ubiquitin-1 gene promoter Ubi-1 in the plasmid constructs pnCas9-PBE and pdCas9-PBE (FIG. 1a).

The ability to convert blue fluorescent protein (BFP) into green fluorescent protein (GFP) of the two constructs in wheat and rice protoplasts was compared. This conversion involves mutating the first nucleotide of the 66th codon of the BFP encoding gene from C to T, resulting in alteration of CAC (histidine) to TAC (tyrosine).

Figure 1B:
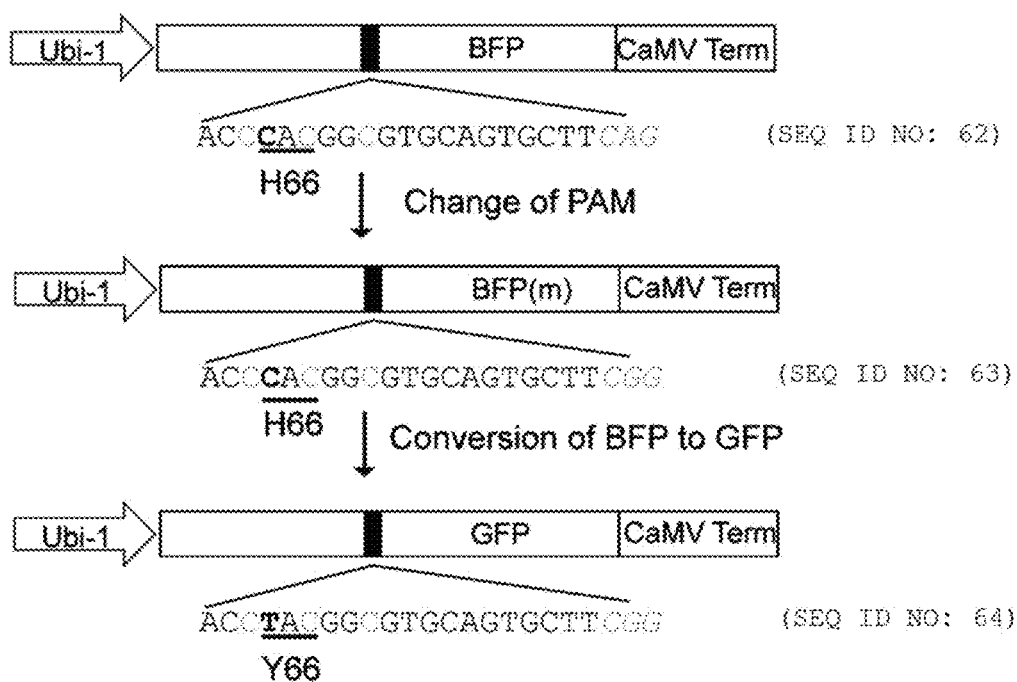

The target region of BFP-specific sgRNA is designed to cover codons ranging from codon 65 to 71 and the first two nucleotides of the codon 72, and the last three bases (CAG) constitute the protospacer adjacent motif (PAM) (FIG. 1b). The C base to be mutated is located at position 4 of the target sequence. The sgRNAs are transcribed using the promoters TaU6 and OsU3, respectively (FIG. 1b). The construction of the sgRNA expression vectors pTaU6-BFP-sgRNA and pOsU3-BFP-sgRNA is described above.

Because CAG is not the optimal PAM for CRISPR/Cas9, CAG was artificially mutated into CGG, and the resulting BFP sequence (BFPm) was cloned downstream of the Ubi-1 promoter to form the expression construct pUbi-BFPm (FIG. 1b) as the target to be edited in protoplasts.

Figure 1C:
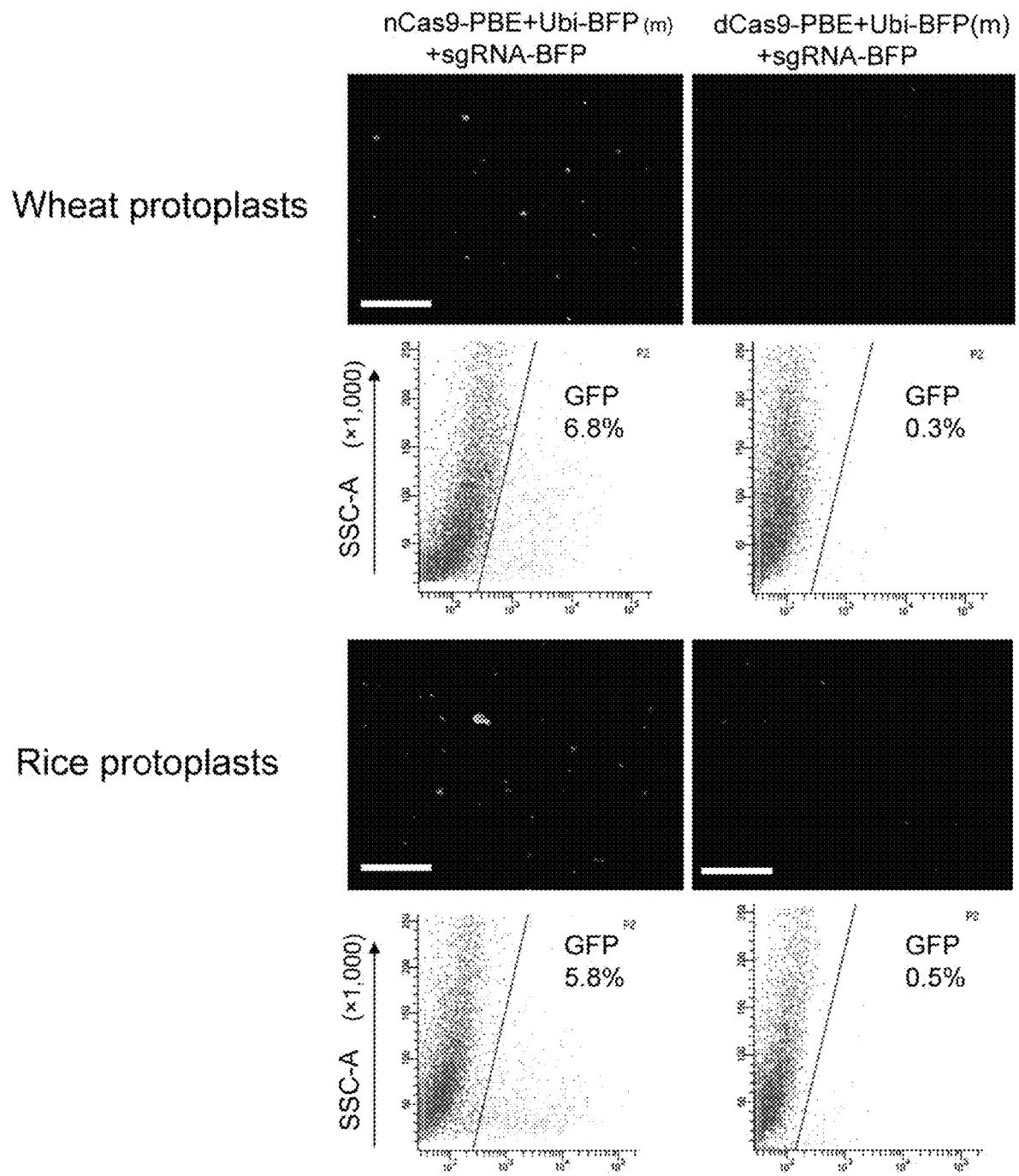
Figure 1C:
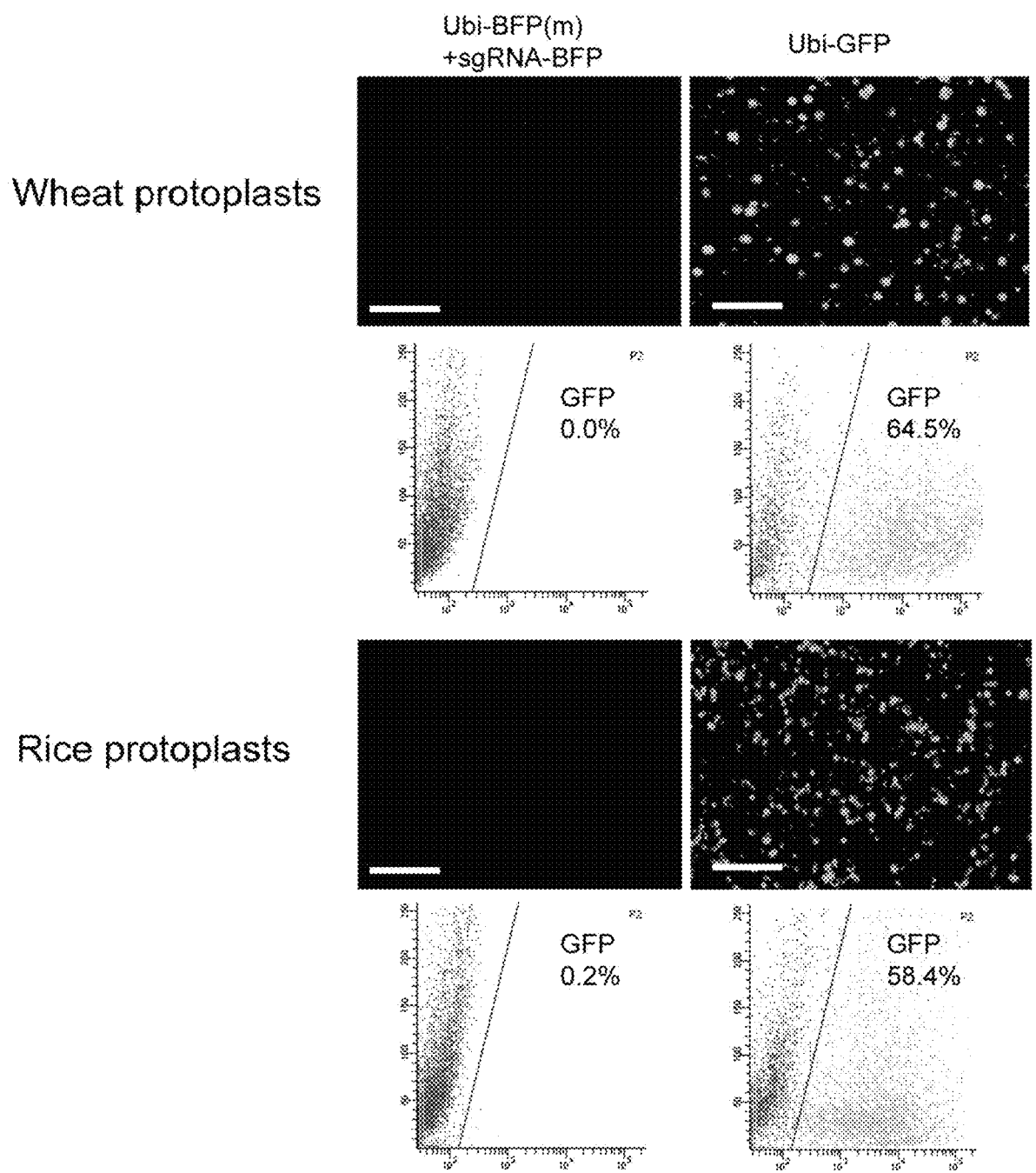

The combination of pnCas9-PBE, pUbi-BFPm, and pOsU3-BFP-sgRNA resulted in the expression of GFP in 5.8% of cells when introduced into rice protoplasts, whereas the replacement of pnCas9-PBE with pdCas9-PBE resulted in only 0.5% GFP-expressing cells; no GFP-expressing cell was detected when pnCas9-PBE or pdCas9-PBE were not included. 58.4% of cells expressed GFP (FIG. 1c) in parallel positive controls (cells were transformed with GFP-expressing construct pUbi-GFP).

In wheat protoplasts, more GFP-expressing cells were produced by using pnCas9-PBE (6.8%) than pdCas9-PBE (0.3%).

In-depth sequencing of rice (wheat or maize) protoplasts transformed with pnCas9-PBE, pUbi-BFPm, and pOsU3-BFP-sgRNA (pTaU6-BFP-sgRNA or pZmU3-BFP-sgRNA) showed that about 4.00% of the total DNA reads carrying C to T mutation (FIG. 1d). Mutation only occurred to C bases at position 3, 4, 6, and 9 in the protospace sequence (target sequence), and the mutation frequencies are 2.48-3.92%, 3.06-3.79%, 5.86-8.75%, and 6.47-7.86% respectively (FIG. 1d). The desired C (position 4) was also mutated, although its mutation frequency is not the highest. When pdCas9-PBE is replaced with pnCas9-PBE, the C bases at the above positions were also mutated, but the mutation frequency (0.06-0.22%) is significantly lower than pnCas9-PBE (2.48-8.75%) (FIG. 1d).

Therefore, the results of the fluorescent protein reporter assay show that both nCas9-PBE and dCas9-PBE are able to convert C to T in the target region in wheat, rice, and maize protoplasts, and the deamination window encompasses position 3-9 of the protospace sequence (target sequence). And the activity of nCas9-PBE is stronger than that of dCas9-PBE.

Example 2. Base Editing of Endogenous Genes in Plant Protoplasts by nCas9-PBE and dCas9-PBE In this example, the activity of pnCas9-PBE or pdCas9-PBE on wheat, rice, and maize endogenous genes was further studied. As a control for the induction of indel, a construct pwCas9 (Addgene ID53064) expressing wild-type Cas9 was also used in this experiment.

Three different sgRNA target sites (Si, S2, and S3) were designed in the TaLOX2 gene of wheat. For each of the three rice genes OsCDC48, OsNRT1.1B, and OsSPL14, one sgRNA target site was designed. One sgRNA target site was designed in maize ZmCENH3 gene (see Table 1).

Each sgRNA expression construct was combined with pnCas9-PBE, pdCas9-PBE, and pwCas9, respectively, and co-expressed in wheat, rice, and maize protoplasts, respectively. Protoplast DNA was extracted. PCR amplicons for seven different targets were prepared and sequenced. 100000 to 270000 sequencing reads were used for detailed analysis of the mutagenicity.

Figure 2A:
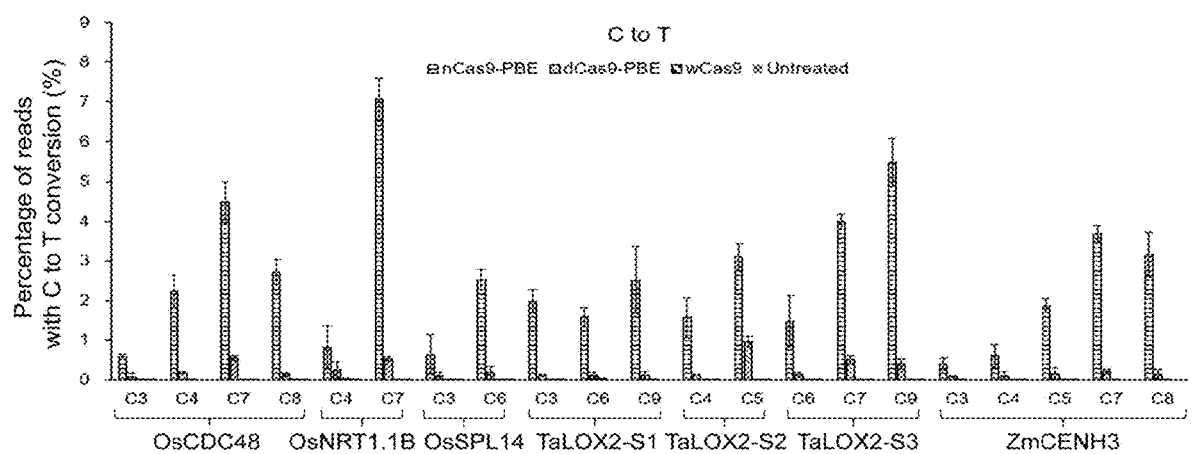
FIG. 2. The Targeted-PBE system mediates point mutation of endogenous genes in plant protoplasts. (a) Frequency of targeted single C to T substitution. The values and error bars reflect means and standard deviations (s.d.) of three biologically replicates on different days. (b) Frequency of multiple Cytidine substitution created by nCas9-PBE, based on the number of mutant reads relative to the total number of captured reads. "--" indicates not available. (c) Frequency of indels formation for seven target sites of endogenous genes in plant protoplasts. The percentage of total DNA sequencing reads with T or indels at the target positions indicated are shown for treatment with nCas9-PBE, dCas9-PBE, or wild type Cas9. The values and error bars reflect the mean and s.d. for three biological replicates performed on different days. (d) Spectrum of point mutations created by using nCas9-PBE in the CENP-A targeting domain (CATD) of ZmCENH3. The three consecutive residues, alanine-leucine-leucine (ALL), in wild type ZmCENH3 were mutated into AFL, VLL, ALF, AFF, VFL, VLF, or VFF. The CATD regions of Arabidopsis thaliana CENH3 (AtCENH3) and Hordeum vulgare L. CENH3 (HvβCENH3) were included in this figure to facilitate the comparison. The underlined leucine residue has previously been shown to be required for the proper function of AtCENH3 and HvCENH3. It has been found that the underlined leucine and alanine residues in AtCENH3 are substituted to result in haploid induction. The GenBank accession numbers for ZmCENH3, AtCENH3, and HvCENH3 are AF519807, AF465800 and JF419329, respectively.

For pnCas9-PBE, C to T transitions were observed in all 7 targets, and the deamination window encompasses positions 3-6 of the protospace sequence (target sequence) (FIG. 2a). The frequency of a single substitution of C to T is 0.57% to 7.07%, the C base at position 7 or near position 7 has the highest substitution frequency, and the editing event is independent of the sequence structure (FIG. 2a). The frequency of multiple C editing (including 2 to 5 Cs) is between 0.31% and 12.48%, while the frequency of editing two or three Cs is higher (FIG. 2b). The pnCas9-PBE-induced indel frequency is very low (0.01%-0.34%) at 7 target sites compared to pwCas9-induced indel frequency (6.27%-11.68%) (FIG. 2c and Table 3).

Figure 2C:
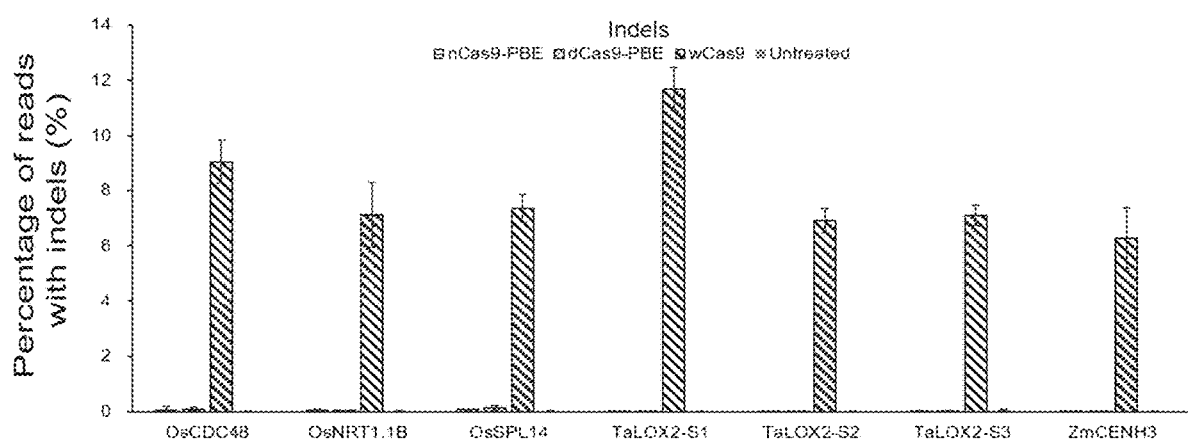

On the other hand, the expression of pdCas9-PBE produced only a low frequency of single C-editing (<0.96%) or multiple Cs-editing (<1.29%) at 7 target sites (FIG. 2a and Table 2), whereas the frequency of the appearance of indel (<0.06%) is comparable to pnCas9-PBE (FIG. 2c and Table 3). It is clear that the results of this experiment verify the previous result in reporter gene assays that nCas9-PBE is superior over dCas9-PBE, and verify the size of the deamination window in cereal plant cells (a 7 nucleotides window at positions 3-9). It also verifies that nCas9-PBE does not rely on target site context sequences to edit a single C and multiple Cs in high efficiency.

Using ZmCENH3 as an example, the amino acid mutation caused by nCas9-PBE in the target genome region was analyzed. As shown in FIG. 2d, in the wild-type ZmCENH3, the conserved residue is leucine residue located in the middle of an alanine-leucine-leucine (ALL, residues 109-111) segment. In the amplicons of ZmCENH3 target site obtained from the protoplasts treated with nCas-PBE, it is easy to identify A109V, L110V, and/or L111F substitutions (FIG. 2d). The ability of nCas9-PBE to edit a single C and multiple Cs allows a total of 7 different types of substitution to ALL, including a single substitution for each residue (AFL, VLL, and ALF), double substitutions of two residues (AFF, VFL, and VLF) and triple substitutions of all three residues (VFF) (FIG. 2d). Substitution event ZmCENH3-AFL has been studied in Arabidopsis and barley, but the remaining single, double, and triple substitutions events have not been reported in any research previously.

TABLE 3

Efficiency of Indel Induction

| | nCas9-PBE | dCas9-PBE | wCas9 | Untreated |
|---|---|---|---|---|
| TaLOX2-S1 | 0.01 | 0.01 | 11.68 | 0.01 |
| TaLOX2-S2 | 0.03 | 0.02 | 6.92 | 0.02 |
| TaLOX2-S3 | 0.04 | 0.03 | 7.10 | 0.06 |
| OsCDC48 | 0.22 | 0.13 | 9.04 | 0.02 |
| OsNRT1.1B | 0.06 | 0.05 | 7.12 | 0.03 |
| OsSPL14 | 0.08 | 0.14 | 7.34 | 0.04 |
| ZmCENH3 | 0.02 | 0.01 | 6.27 | 0.01 |

Example 3. Analysis for Mutant Plants

This example further investigated the functional differences between nCas9-PBE and dCas9-PBE and tested the functional properties of nCas9-PBE by analyzing mutant plants.

Figure 3A:
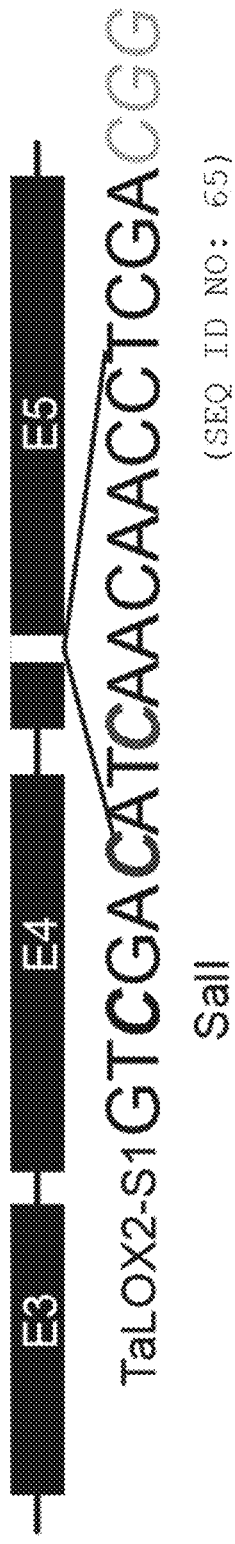
FIG. 3. Genetically engineered wheat and rice plants obtained by application of the Targeted-PBE system. (a) Sequence of a sgRNA designed to target a site of exon 5 of TaLOX2. The targeted C in the deamination window is bold and italic. The PAM sequence is shown in italic, and the SalI restriction site is GTCGAC. (b) Results of T7E1 and PCR-RE assays analyzing two mutants with TaLOX2 point mutation. Lanes T0-1 to T0-5 show blots of PCR fragments amplified from independent wheat plants digested with T7E1 and SalI. Lanes labeled WT/D and WT/U are PCR fragments amplified from wild type plants digested with or without T7E1 and SalI, respectively. The bands marked by arrowheads are caused by Targeted-PBE-induced mutations. Genotypes of two mutants with point mutation were further identified by Sanger sequencing. (c) Schematic of the Agrobacterium expression vector pAG-n/dCas9-PBE, which is used for targeting the OsCDC48 gene. Hyg is driven by the 2×35S promoter. (d) Sequence of an sgRNA designed to target exon 9 of OsCDC48. The results of T7E1 assays analyzing twelve representative mutants with OsCDC48 point mutation are shown. (e) Genotype and frequency of rice mutants with OsCDC48 point mutation identified through Sanger sequencing. The frequency of point mutation for each genotype (each genotype mutant vs. rice mutants in total) is shown at right. Target bases are $C_3$, $C_4$, $C_7$, and $C_8$, the subscripted number represents its location in the target sequence. The sequences below are the sequencing results for rice mutants.
Figure 3B:
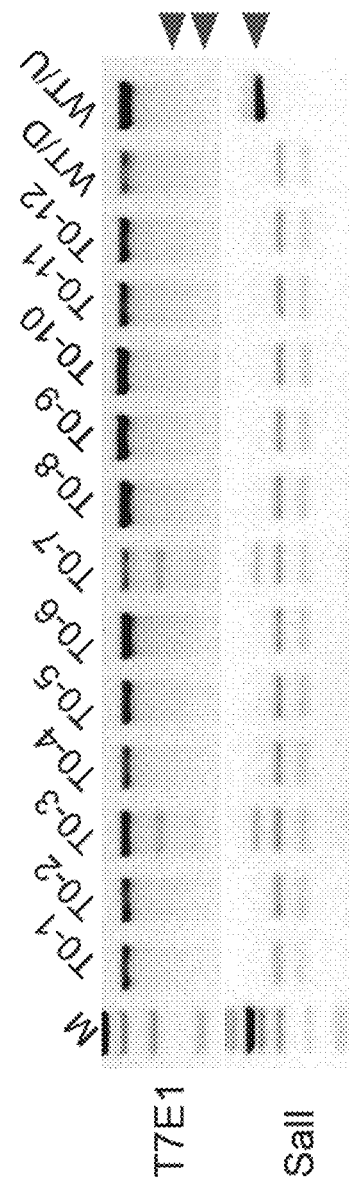

For wheat transformation, pnCas9-PBE and pTaU6-sgRNA-LOX2-s1 (FIG. 3a) were co-transformed into a bread wheat variety, Bobwhite by particle bombardment, and plants were regenerated without herbicide selection. The target site of sgRNA-LOX2-s1 was amplified from the genomic DNA of the regenerated plants using specific primers (Table 4). Two lines carrying nucleotide substitutions were identified from 160 immature embryos by T7EI and restriction enzyme digestion (PCR-RE). The mutation efficiency is 1.25% (2/160) (FIG. 3b). Sanger sequencing confirmed that the mutant T0-3 contains all three C to T substitutions at positions 3, 6, and 9 downstream of the PAM, whereas the mutant T0-7 carries a C to T mutation at position 3 (FIG. 3b). We failed to detect indels in these two mutant plants.

Figure 3C:
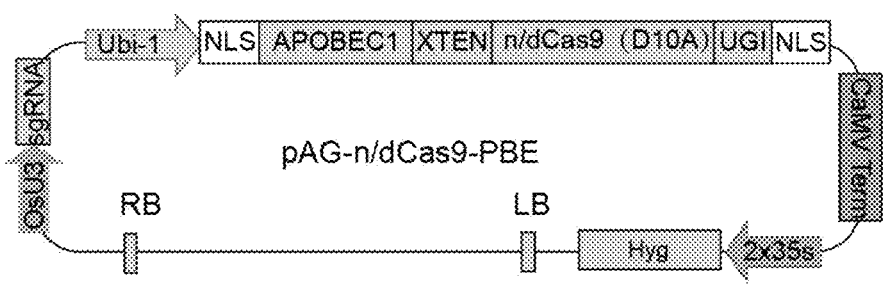

Rice variety Nipponbare (Japonica) was used for rice transformation, because this variety is highly responsive to genetic manipulation and its whole genome sequence is available. The OsCDC48 gene, which has been found to regulate rice senescence and cell death, is adopted as a target (FIG. 3c and Table 1). The pAG-n/dCas9-PBE-CDC48-sgRNA binary vector was transformed into rice by Agrobacterium-mediated gene transfer method.

Figure 3D:
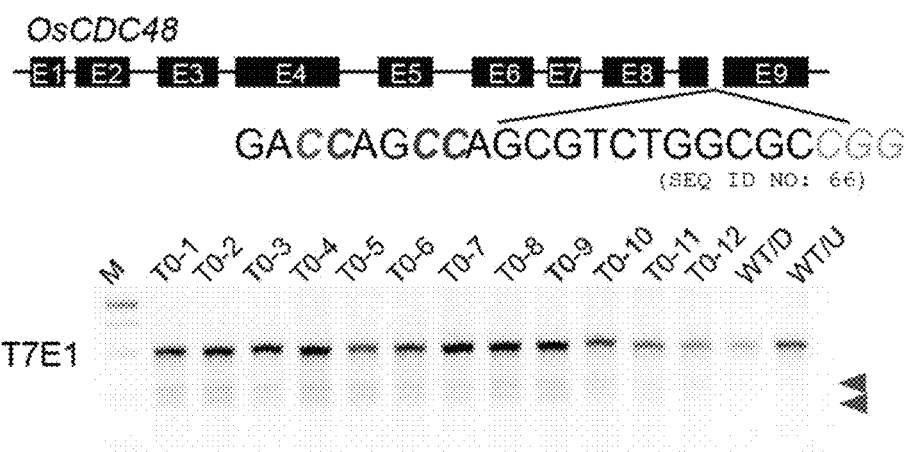

92 and 87 independent transgenic T0 plants were obtained for nCas9-PBE and dCas9-PBE, respectively. After T7EI analysis and Sanger sequencing, it is found that among the 92 nCas9-PBE plants, 40 of them carry at least one C to T substitution in the OsCDC48 target region, and the mutant production efficiency is 43.48% (40/92) (FIG. 3d). A representative sequencing result is shown in FIG. 4. Among the

TABLE 2

Efficiency of dCas9-PBE treatment induced multiple C substitution

| Gene Name | Total reads | 2 Cs | | 3 Cs | | 4 Cs | | 5 Cs | |
|---|---|---|---|---|---|---|---|---|---|
| | | Mutant reads | Mutagenesis frequency | Mutant reads | Mutagenesis frequency | Mutant reads | Mutagenesis frequency | Mutant reads | Mutagenesis frequency |
| sgRNA-TaLOX2-s1 | 197064 | 72 | 0.04% | 4 | 0.00% | — | — | — | — |
| sgRNA-TaLOX2-s2 | 149200 | 420 | 0.28% | — | — | — | — | — | — |
| sgRNA-TaLOX2-s3 | 96396 | 1244 | 1.29% | — | — | — | — | — | — |
| sgRNA-OsCDC48 | 154760 | 40 | 0.03% | 0 | 0.00% | 0 | 0.00% | — | — |
| sgRNA-OsNRT1.1B | 142130 | 0 | 0.00% | — | — | — | — | — | — |
| sgRNA-OsSPL14 | 96659 | 36 | 0.04% | — | — | — | — | — | — |
| sgRNA-ZmCENH3 | 275466 | 36 | 0.01% | 0 | 0.00% | 0 | 0.00% | 0 | 0.00% |

"—" represents not applicable;
[a]The number of mutant reads relative to the number of total reads.

Figures 3E, 4A:
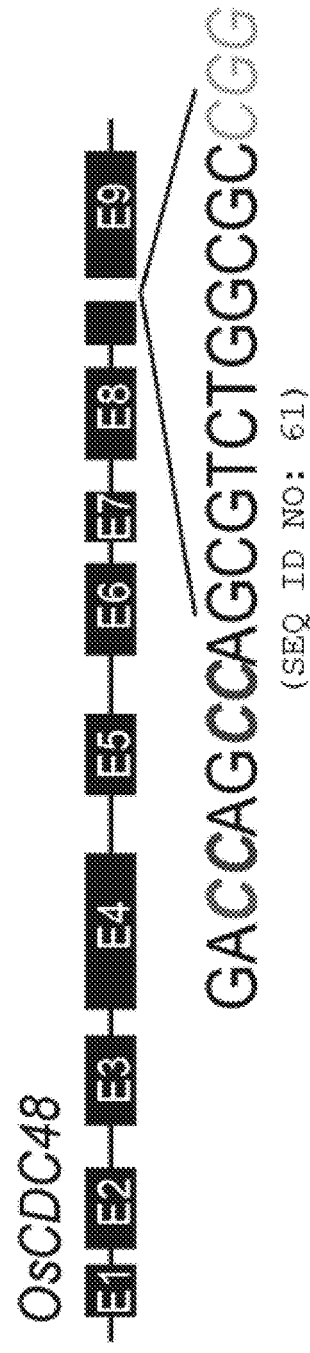
FIG. 4. Genotypes of 12 representative mutants with OsCDC48 point mutation identified through Sanger sequencing. Italic and bold base C represents the Cs to be mutated at position 3, 4, 7, and 8 of the deamination window. t represents successful C to T substitution in the target sites.

40 mutants, mutations are detected only for C bases at positions 3, 4, 7, and 8 of the target region, and a total of seven different types of point mutations are identified (FIG. 3e). Specifically, there are four single nucleotide mutations (C3T, C4T, C7T, and C8T), two double nucleotide mutations (C3C4 to T3T4 and C7C8 to T7T8), and one triple nucleotide mutation (C3C4C7 to T3T4T7) (FIG. 3e). Therefore, nCas9-PBE encompasses 7 nucleotides (positions 3-9) in the deamination window in these rice mutants. The mutation frequency for each C ranges between 5.00% (C3, 2/40) to 32.50% (C7, 13/40) with the highest editing frequency for C at position 7. No indel is observed in the target region of the 40 mutants. Surprisingly, when using T7EI assay and Sanger sequencing analysis, no point mutation or indel was detected in the target region of OsCDC48 for the 87 dCas9-PBE plants.

The potential off-target effect of the base editing method of the present invention was investigated based on the obtained 40 strains of nCas-PBE mutants. Five possible off-target sites are found in the Nipponbare genomic sequence, each of them has three nucleotide mismatches with the sgRNA target region of OsCDC48 (Table 4). Amplicons of these 5 sites are carefully analyzed using T7EI assay and Sanger sequencing. No point mutation or indel was detected, indicating that base editing by nCas9-PBE is highly specific.

Figures 5A, 5B:
FIG. 5. Base editing of ZmALS1/ZmALS2 through nCas9-PBE system. (a) Genome structure of ZmALS1/ZmALS2 and the common sgRNA target sequence; (b) detecting C to T substitution types of ZmALS1/ZmALS2 in different nCas9-PBE modified lines.

NO: 28) (Svitashev et al., Plant Physiol., 2015), which is CAGGTGCCGCGACGCATGAT<u>TGG</u> (SEQ ID NO: 56). A base editing system was constructed as described above, and transformed into maize variety Zong31 by particle bombardment method. After PCR/RE detection, plants with C7 to T7 substitution on ZmALS1 and ZmALS2 were obtained (FIG. 5).

Based on the data shown above, the modified and optimized nCas9-PBE induces highly efficient and specific C to T base editing in wheat, rice, and maize cells, and the point mutation produced by nCas9-PBE is unique comparing to the ones produced by TILLING. nCas9-PBE in combination of a properly engineered sgRNA can make it possible to perform a point mutation to a desired residue and adjacent residues, and thus facilitates the analysis for the effect of a single or combined mutations of amino acids located in a key domain of a protein. On the other hand, point mutations identified by TILLING usually only appear to a single amino acid residue, and accordingly it is difficult to simultaneously obtain mutations of the target residue and its adjacent residues by TILLING. Therefore, nCas9-PBE is clearly advantageous for the rapid generation of multiple mutations, and can be used for the detail analysis of the function of one or more amino acids in a key protein domain. Important functional properties of nCas9-PBE include a relatively

TABLE 4

Potential off-target effect analysis for OsCDC48

| Site name | SEQ ID NO: | Sequence | Number of mismatch | Gene | Mutagenesis frequency | Sequencing method |
|---|---|---|---|---|---|---|
| On-target | 61 | GACCAGCCAGCGTCTGGC GCCGG | | LOC_Os03g05730 | | |
| OT-1 | 102 | GACCAGCCgGCGTgTGGtG CAGG | 3 | LOC_Os12g09720 | 0 | T7EI/Sanger Sequencing |
| OT-2 | 102 | GACCAGCCgGCGTgTGGtG CAGG | 3 | LOC_Os12g09700 | 0 | T7EI/Sanger Sequencing |
| OT-3 | 102 | GACCAGCCgGCGTgTGGtG CAGG | 3 | LOC_Os12g14440 | 0 | T7EI/Sanger Sequencing |
| OT-4 | 103 | GACCAGCCAGCGTCTGaa GgCGG | 3 | LOC_Os03g19390 | 0 | T7EI/Sanger Sequencing |
| OT-5 | 104 | GACCAagCAGCGgCTGGC GCCGG | 3 | LOC_Os04g34030 | 0 | T7EI/Sanger Sequencing |

Lowercase bases are bases mismatched with OsCDC48. The bold letters show the PAM sequence.

Example 4. Base Editing of Maize ALS Gene

Using AtALS (AT3G48560.1) as a seed sequence, two ZmALS homologous genes are obtained by BLASTN alignment analysis in a maize database (https://phytozome.jgi.doe.gov), wherein the two ZmALS homologous genes are named as ZmALS1 (Locus Name: GRMZM2G143357) and ZmALS2 (Locus Name: GRMZM2G143008). ZmALS1 and ZmALS2 have a sequence identify of 93.84%. A common sgRNA target sequence was designed in the conserved region of ZmALS1 (SEQ ID NO: 26) and ZmALS2 (SEQ ID large deamination window (covering 7 bases of the protospace sequence/target sequence), its base editing is independent of the sequence context structure of the target region, and there are few indel mutations. nCas9-PBE has a larger deamination window in cereal plants, which is advantageous for generating more diverse mutations.

The present invention demonstrates that C to T base-editing, which is mediated by the Cas9 variant-cytidine deaminase fusion protein, is a highly efficient tool for producing site-directed point mutations in the plant genome, and thereby increases the efficiency of improving crops through genomic engineering.

TABLE 5

All of the Primers Used in the Examples

| Primer Name | SEQ ID NO: | Primer Sequence (5'-3') | Application |
|---|---|---|---|
| BFPm-F | 105 | ACGGCGTGCAGTGCTTCGGCCGCTACCCCGACCA | Construct |
| BFPm-R | 106 | TGGTCGGGGTAGCGGCCGAAGCACTGCACGCCGT | pJIT163-Ubi-BFPm |
| AfIII-n/dCas9-F | 107 | GGCTTAAGGACAAGAAGTACTCGATCGGCCT | Amplify n/dCas9 segment |
| MluI-n/dCas9-R | 108 | GCGACGCGTCTTCTTCTTCTTTGCTTGCCCTGC | |
| BamHI-n/dCas9-F | 109 | CGGGATCCATGCCAAAGAAGAAGAGGAAGGTTTCATC | Amplify |
| Bsp1047I-n/dCas9-R | 110 | CCGTGTACACTACACCTTCCGCTTCTTCTTTGGGCTC | APOBEC1-XTEN-n/dCas9 segment |
| Gibson-F | 111 | AATACTTGTATGGCCGCGGCCATGC-CAAAGAAGAAGAGG | Amplify |
| Gibson-R | 112 | ACTTGTATGGAGGCCTGAGCTCTA-CACCTTCCGCTTCTT | APOBEC1-XTEN-n/dCas9 segment |
| BFP-F | 113 | ATGGTGAGCAAGGGCGAGGAG | Amplify BFP gene target site and for first-round PCR for in-depth sequencing |
| BFP-R | 114 | CCTCGATGTTGTGGCGGATCT | |
| OsBFP-nCas9-F | 115 | CGATGTCGAGGGCGATGCCACCTAC | Second-round PCR for BFP in-depth sequencing in nCas9-PBE treated rice protoplasts |
| OsBFP-nCas9-R | 116 | TGGTCAAAGTCGTGCTGCTTCATGTGG | |
| OsBFP-dCas9-F | 117 | ATCACGCGAGGGCGATGCCACCTAC | Second-round PCR for BFP in-depth sequencing in dCas9-PBE treated rice protoplasts |
| OsBFP-dCas9-R | 118 | GCCTAAAAGTCGTGCTGCTTCATGTGG | |
| OsBFP-Cas9-F | 119 | AGTTCCCGAGGGCGATGCCACCTAC | Second-round PCR for BFP in-depth sequencing in wild-type Cas9 treated rice protoplasts |
| OsBFP-Cas9-R | 120 | CTCTACAAGTCGTGCTGCTTCATGTGG | |
| OsBFP-CK-F | 121 | CACTCACGAGGGCGATGCCACCTAC | Second-round PCR for BFP in-depth sequencing in control rice protoplasts |
| OsBFP-CK-R | 122 | TGTTGGAAGTCGTGCTGCTTCATGTGG | |
| TaBFP-nCas9-F | 123 | GTGGCCCGAGGGCGATGCCACCTAC | Second-round PCR for BFP in-depth sequencing in nCas9-PBE treated wheat protoplasts |
| TaBFP-nCas9-R | 124 | CGAAACAAGTCGTGCTGCTTCATGTGG | |
| TaBFP-dCas9-F | 125 | CGTACGCGAGGGCGATGCCACCTAC | Second-round PCR for BFP in-depth sequencing in dCas9-PBE treated wheat protoplasts |
| TaBFP-dCas9-R | 126 | CCACTCAAGTCGTGCTGCTTCATGTGG | |
| TaBFP-Cas9-F | 127 | GGTAGCCCGAGGGCGATGCCACCTAC | Second-round PCR for BFP in-depth sequencing in wild-type Cas9 treated wheat protoplasts |
| TaBFP-Cas9-R | 128 | ATCAGTAAGTCGTGCTGCTTCATGTGG | |
| TaBFP-CK-F | 129 | CACCGGCCGAGGGCGATGCCACCTAC | Second-round PCR for BFP in-depth sequencing in control wheat protoplasts |
| TaBFP-CK-R | 130 | ATCGTGAAGTCGTGCTGCTTCATGTGG | |
| ZmBFP-nCas9-F | 131 | ATGAGCCGAGGGCGATGCCACCTAC | Second-round PCR for BFP in-depth sequencing in nCas9-PBE treated maize protoplasts |
| ZmBFP-nCas9-R | 132 | AGGAATAAGTCGTGCTGCTTCATGTGG | |
| ZmBFP-dCas9-F | 133 | CAAAAGGCGAGGGCGATGCCACCTAC | Second-round PCR for BFP in-depth sequencing in dCas9-PBE treated maize protoplasts |
| ZmBFP-dCas9-R | 134 | TAGTTGAAGTCGTGCTGCTTCATGTGG | |
| ZmBFP-Cas9-F | 135 | TCGGCACGAGGGCGATGCCACCTAC | Second-round PCR for BFP in-depth sequencing in wild-type Cas9 treated maize protoplasts |
| ZmBFP-Cas9-R | 136 | GAATGAAAGTCGTGCTGCTTCATGTGG | |
| ZmBFP-CK-F | 137 | TCCCGACGAGGGCGATGCCACCTAC | Second-round PCR for BFP in-depth sequencing in control maize protoplasts |
| ZmBFP-CK-R | 138 | CTTCGAAAGTCGTGCTGCTTCATGTGG | |

TABLE 5-continued

All of the Primers Used in the Examples

| Primer Name | SEQ ID NO: | Primer Sequence (5'-3') | Application |
|---|---|---|---|
| OsCDC48-F | 139 | TTCAGGACATCGAGATGGAGAAG | Amplify OsCDC48 target site and for first-round PCR for in-depth sequencing |
| OsCDC48-R | 140 | ACAACGCAAATCTATCCATGCTC | |
| OsCDC48-nCas9-F | 141 | CGATGTGCCGACATCCGCAAGTACCAG | Second-round PCR for OsCDC48 in-depth sequencing in nCas9-PBE treated rice protoplasts |
| OsCDC48-nCas9-R | 142 | TGGTCATCATCATCGTCAGCTGCGGC | |
| OsCDC48-dCas9-F | 143 | ATCACGGCCGACATCCGCAAGTACCAG | Second-round PCR for OsCDC48 in-depth sequencing in dCas9-PBE treated rice protoplasts |
| OsCDC48-dCas9-R | 144 | GCCTAATCATCATCGTCAGCTGCGGC | |
| OsCDC48-Cas9-F | 145 | AGTTCCGCCGACATCCGCAAGTACCAG | Second-round of PCR for OsCDC48 in-depth sequencing in wild-type Cas9 treated rice protoplasts |
| OsCDC48-Cas9-R | 146 | CTCTACTCATCATCGTCAGCTGCGGC | |
| OsCDC48-CK-F | 147 | CACTCAGCCGACATCCGCAAGTACCAG | Second-round PCR for OsCDC48 deep sequencing in control rice protoplasts |
| OsCDC48-CK-R | 148 | TGTTGGTCATCATCGTCAGCTGCGGC | |
| OsNRT1.1B-F | 149 | GATGTCACCTGATGATCTGAAGTAGC | Amplify OsNRT1.1B target site and for first-round PCR for in-depth sequencing |
| OsNRT1.1B-R | 150 | ATGATGGTGGTCGCCCAGAT | |
| OsNRT1.1B-nCas9-F | 151 | CGATGTGGTGCAGGTTCCTGGACCAT | Second-round PCR for OsNRT1.1B in-depth sequencing in nCas9-PBE treated rice protoplasts |
| OsNRT1.1B-nCas9-R | 152 | TGGTCAATGATGGTGGTCGCCCAGAT | |
| OsNRT1.1B-dCas9-F | 153 | ATCACGGGTGCAGGTTCCTGGACCAT | Second-round PCR for OsNRT1.1B in-depth sequencing in dCas9-PBE treated rice protoplasts |
| OsNRT1.1B-dCas9-R | 154 | GCCTAAATGATGGTGGTCGCCCAGAT | |
| OsNRT1.1B-Cas9-F | 155 | AGTTCCGGTGCAGGTTCCTGGACCAT | Second-round PCR for OsNRT1.1B in-depth sequencing in wild-type Cas9 treated rice protoplasts |
| OsNRT1.1B-Cas9-R | 156 | CTCTACATGATGGTGGTCGCCCAGAT | |
| OsNRT1.1B-CK-F | 157 | CACTCAGGTGCAGGTTCCTGGACCAT | Second-round PCR for OsNRT1.1B in-depth sequencing in control rice protoplasts |
| OsNRT1.1B-CK-R | 158 | TGTTGGATGATGGTGGTCGCCCAGAT | |
| OsSPL14-F | 159 | CGCTGATGTGTTGTTTGTTGCGA | Amplify OsSPL14 target site and for first-round PCR for in-depth sequencing |
| OsSPL14-R | 160 | CCTGCAGAGCAAGCTCAAGCTCA | |
| OsSPL14-nCas9-F | 161 | CGATGTTCGCTGGCCCAAATCTCCCT | Second-round PCR for OsSPL14 in-depth sequencing in nCas9-PBE treated rice protoplasts |
| OsSPL14-nCas9-R | 162 | TGGTCAGACATGGCTGCAGCCTGGTT | |
| OsSPL14-dCas9-F | 163 | ATCACGTCGCTGGCCCAAATCTCCCT | Second-round PCR for OsSPL14 in-depth sequencing in dCas9-PBE treated rice protoplasts |
| OsSPL14-dCas9-R | 164 | GCCTAAGACATGGCTGCAGCCTGGTT | |
| OsSPL14-Cas9-F | 165 | AGTTCCTCGCTGGCCCAAATCTCCCT | Second-round PCR for OsSPL14 in-depth sequencing in wild-type Cas9 treated rice protoplasts |
| OsSPL14-Cas9-R | 166 | CTCTACGACATGGCTGCAGCCTGGTT | |
| OsSPL14-CK-F | 167 | CACTCATCGCTGGCCCAAATCTCCCT | First-round PCR for OsSPL14 in-depth sequencing in control rice protoplasts |
| OsSPL14-CK-R | 168 | TGTTGGGACATGGCTGCAGCCTGGTT | |

TABLE 5-continued

All of the Primers Used in the Examples

| Primer Name | SEQ ID NO: | Primer Sequence (5'-3') | Application |
|---|---|---|---|
| TaLOX2-S1-F | 169 | ACTCCGTCTACCGACCATTGAG | Amplify TaLOX2 S1 target site and for first-round PCR for in-depth sequencing |
| TaLOX2-S1-R | 170 | TAGACCATGGAGGACATGGGCAT | |
| TaLOX2-S1-nCas9-F | 171 | GTGGCCAGGGCCTCACCGTGGAGCAGA | Second-round PCR for TaLOX2-S1 in-depth sequencing in nCas9-PBE treated wheat protoplasts |
| TaLOX2-S1-nCas9-R | 172 | CGAAACTCCCCTCGCAGGAAGAGCAG | |
| TaLOX2-S1-dCas9-F | 173 | CGTACGAGGGCCTCACCGTGGAGCAGA | Second-round PCR for TaLOX2-S1 in-depth sequencing in dCas9-PBE treated wheat protoplasts |
| TaLOX2-S1-dCas9-R | 174 | CCACTCTCCCCTCGCAGGAAGAGCAG | |
| TaLOX2-S1-Cas9-F | 175 | GGTAGCAGGGCCTCACCGTGGAGCAGA | Second-round PCR for TaLOX2-S1 in-depth sequencing in Cas9 treated wild-type wheat protoplasts |
| TaLOX2-S1-Cas9-R | 176 | ATCAGTTCCCCTCGCAGGAAGAGCAG | |
| TaLOX2-S1-CK-F | 177 | CGGAATAGGGCCTCACCGTGGAGCAGA | Second-round PCR for TaLOX2-S1 in-depth sequencing in control wheat protoplasts |
| TaLOX2-S1-CK-R | 178 | TCTGAGTCCCCTCGCAGGAAGAGCAG | |
| TaLOX2-S2-F | 179 | CAATCATCGATGTACTAGTGTGGTCCAG | Amplify TaLOX2 S2 target site and for first-round PCR for in-depth sequencing |
| TaLOX2-S2-R | 180 | GGATGTCGGCGAAGGAGTCGAACT | |
| TaLOX2-S2-nCas9-F | 181 | ATGAGCTATGTATGGCTGGCGCAGAGC | Second-round PCR for TaLOX2-S2 in-depth sequencing in nCas9-PBE treated wheat protoplasts |
| TaLOX2-S2-nCas9-R | 182 | AGGAATGTATGATCCCGTCCACCAGC | |
| TaLOX2-S2-dCas9-F | 183 | CAAAAGTATGTATGGCTGGCGCAGAGC | Second-round PCR for TaLOX2-S2 in-depth sequencing in dCas9-PBE treated wheat protoplasts |
| TaLOX2-S2-dCas9-R | 184 | TAGTTGGTATGATCCCGTCCACCAGC | |
| TaLOX2-S2-Cas9-F | 185 | CACCGGTATGTATGGCTGGCGCAGAGC | Second-round PCR for TaLOX2-S2 in-depth sequencing in Cas9 treated wild-type wheat protoplasts |
| TaLOX2-S2-Cas9-R | 186 | ATCGTGGTATGATCCCGTCCACCAGC | |
| TaLOX2-S2-CK-F | 187 | CTAGCTTATGTATGGCTGGCGCAGAGC | Second-round PCR for TaLOX2-S2 in-depth sequencing in control wheat protoplasts |
| TaLOX2-S2-CK-R | 188 | TCTGAGGTATGATCCCGTCCACCAGC | |
| TaLOX2-S3-F | 189 | GTCCCCTTCCTTCCGATCTAATCTC | Amplify TaLOX2 S3 target site and for first-round PCR for in-depth sequencing |
| TaLOX2-S3-R | 190 | TGCACGCAGTCAAATAATGGTACGA | |
| TaLOX2-S3-nCas9-F | 191 | CGATGTCATCAAGCTGCCCAACATCCC | Second-round PCR for TaLOX2-S3 in-depth sequencing in nCas9-PBE treated wheat protoplasts |
| TaLOX2-S3-nCas9-R | 192 | TGGTCATCGGTCATCCATGCCTTCTCGT | |
| TaLOX2-S3-dCas9-F | 193 | ATCACGCATCAAGCTGCCCAACATCCC | Second-round PCR for TaLOX2-S3 in-depth sequencing in dCas9-PBE treated wheat protoplasts |
| TaLOX2-S3-dCas9-R | 194 | GCCTAATCGGTCATCCATGCCTTCTCGT | |
| TaLOX2-S3-Cas9-F | 195 | AGTTCCCATCAAGCTGCCCAACATCCC | Second-round PCR for TaLOX2-S3 in-depth sequencing in Cas9 treated wild-type wheat protoplasts |
| TaLOX2-S3-Cas9-R | 196 | CTCTACTCGGTCATCCATGCCTTCTCGT | |
| TaLOX2-S3-CK-F | 197 | CTATACCATCAAGCTGCCCAACATCCC | Second-round PCR for TaLOX2-S3 in-depth sequencing in control wheat protoplasts |
| TaLOX2-S3-CK-R | 198 | TCTGAGTCGGTCATCCATGCCTTCTCGT | |
| ZmCENH3-F | 199 | AATGTGCCAGTTCCATGTGGGTGT | Amplify ZmCENH3 target site and for first-round PCR for in-depth sequencing |
| ZmCENH3-R | 200 | GCAGGCCATAATGCTGTCGGGTAT | |

TABLE 5-continued

All of the Primers Used in the Examples

| Primer Name | SEQ ID NO: | Primer Sequence (5'-3') | Application |
| --- | --- | --- | --- |
| ZmCENH3-nCas9-F | 201 | ATGAGCATGGAAAGTTATTCTTCTGAGAA | Second-round PCR for ZmCENH3 in-depth sequencing in nCas9-PBE treated maize protoplasts |
| ZmCENH3-nCas9-R | 202 | AGGAATTATGAAGAGGATCTTAACAGAGAG | |
| ZmCENH3-dCas9-F | 203 | CAAAAGATGGAAAGTTATTCTTCTGAGAA | Second-round PCR for ZmCENH3 in-depth sequencing in dCas9-PBE treated maize protoplasts |
| ZmCENH3-dCas9-R | 204 | TAGTTGTATGAAGAGGATCTTAACAGAGAG | |
| ZmCENH3-Cas9-F | 205 | TCGGCAATGGAAAGTTATTCTTCTGAGAA | Second-round PCR for ZmCENH3 in-depth sequencing in Cas9 treated wild-type maize protoplasts |
| ZmCENH3-Cas9-R | 206 | GAATGATATGAAGAGGATCTTAACAGAGAG | |
| ZmCENH3-CK-F | 207 | CTATACATGGAAAGTTATTCTTCTGAGAA | Second-round PCR for ZmCENH3 in-depth sequencing in control maize protoplasts |
| ZmCENH3-CK-R | 208 | TCTGAGTATGAAGAGGATCTTAACAGAGAG | |
| Off-target-1F | 209 | ATGTCGGCCAGCAACAACAA | Potential off-target effect for detection site 1 |
| Off-target-1R | 210 | AGTAGTGTATCCATCCTCGTGCAT | |
| Off-target-2F | 211 | AATAGCCCATTCACCTTGTTCAACA | Potential off-target effect for detection site 2 |
| Off-target-2R | 212 | CAGCCATAGACCATAGTACTACACCAC | |
| Off-target-3F | 213 | TCATCCTCGAACACTAGGCTGAAG | Potential off-target effect for detection site 3 |
| Off-target-3R | 214 | TACTACTCGCAGCGCATCACTCA | |
| Off-target-4F | 215 | ATTGAACGGTGTCACTTCAGACCA | Potential off-target effect for detection site 4 |
| Off-target-4R | 216 | TATTGAGCTGATCAGCTGAACAGAAC | |
| Off-target-5F | 217 | ACTCGCTGGAACTATCCATCTTGGC | Potential off-target effect for detection site 5 |
| Off-target-5R | 218 | AAGCGCTCGACGGCGTGGA | |
| ZmALS1-F | 219 | CTCCGACATCCTCGTCGAGGCT | For maize ZmALS1 PCR/RE test |
| ZmALS1-R | 220 | GATTCACCAACAAGACGCAGCA | |
| ZmALS2-F | 221 | AACCACCTCTTCCGCCACGAG | For maize ZmALS2 PCR/RE test |
| ZmALS2-R | 222 | ACGCAGCACCTGCTCAAGCAAC | |

The invention claimed is:

1. A system for performing base editing to a target sequence in a plant genome, comprising at least one of the following (i) to (v):
   i) a base editing fusion protein, and a guide RNA;
   ii) an expression construct comprising a nucleotide sequence encoding a base editing fusion protein, and a guide RNA;
   iii) a base editing fusion protein, and an expression construct comprising a nucleotide sequence encoding a guide RNA;
   iv) an expression construct comprising a nucleotide sequence encoding a base editing fusion protein, and an expression construct comprising a nucleotide sequence encoding a guide RNA;
   v) an expression construct comprising a nucleotide sequence encoding base editing fusion protein and a nucleotide sequence encoding guide RNA;
   wherein said base editing fusion protein contains a nuclease-inactivated Cas9 domain and a deaminase domain, said guide RNA can target said base editing fusion protein to the target sequence in the plant genome,
   wherein said deaminase domain is fused through a linker to the N-terminal of said nuclease-inactivated Cas9 domain,
   wherein the base editing fusion protein comprises an amino acid sequence as encoded by the nucleotide sequence as set forth in SEQ ID NO: 19 or 20,
   wherein the deaminase is an apolipoprotein B mRNA editing complex (APOBEC) family deaminase having a deamination window of 7 nucleotides at positions 3-9 of the protospacer sequence, and
   wherein the nucleotide sequence encoding the base editing fusion protein is codon optimized for plants to be base edited.

2. The system according to claim 1, wherein said guide RNA is a single guide RNA (sgRNA).

3. The system according to claim 1, wherein a nucleotide sequence encoding said base editing fusion protein and/or a nucleotide sequence encoding said guide RNA are operably linked to an expression regulatory element for the plant.

4. The system according to claim 3, wherein said expression regulatory element is a promoter selected from the group consisting of a 35S promoter, a maize Ubi-1 promoter, a wheat U6 promoter, a rice U3 promoter, and a maize U3 promoter.

5. A method for producing a genetically modified plant, comprising introducing the system according to claim 1 into the plant, and thereby said guide RNA target said base editing fusion protein to a target sequence in the genome of said plant, resulting in one or more C to T substitutions in said target sequence.

6. The method according to claim 5, further comprising screening for plants with desired nucleotide substitution(s).

7. The method according to claim 5, wherein said plant is selected from monocotyledon and dicotyledon.

8. The method according to claim 7, wherein said plant is a crop plant selected from the group consisting of wheat, rice, maize, soybean, sunflower, sorghum, rape, alfalfa, cotton, barley, millet, sugar cane, tomato, tobacco, cassava, and potato.

9. The method according to claim 5, wherein said target sequence is associated with an agronomic trait, and thereby said base editing results in a change of the trait in the plant relative to a wild-type plant.

10. The method according to claim 5, wherein said system is introduced into said plant through a method selected from the group consisting of particle bombardment, PEG-mediated protoplast transformation, *Agrobacterium*-mediated transformation, plant virus-mediated transformation, a pollen tube approach, and ovary injection approach.

11. The method according to claim 5, further comprising obtaining a progeny of the genetically modified plant.

12. The method according to claim 5, wherein the introduction is performed in the absence of any selective pressure.

* * * * *

SEQUENCE LISTING

<160> NUMBER OF SEQ ID NOS: 234

<210> SEQ ID NO 1
<211> LENGTH: 681
<212> TYPE: DNA
<213> ORGANISM: Artificial Sequence
<220> FEATURE:
<223> OTHER INFORMATION: Description of Artificial Sequence: Synthetic
      APOBEC1 encoding sequence

<400> SEQUENCE: 1

```
tcatcggaga ccggccctgt tgctgttgac cccaccctgc ggcggagaat cgagccacac    60
gagttcgagg tgttcttcga cccaagggag ctccgcaagg agacgtgcct cctgtacgag   120
atcaactggg gcggcaggca ctccatctgg aggcacacca gccaaaacac caacaagcac   180
gtggaggtca acttcatcga gaagttcacc accgagaggt acttctgccc aaacacccgc   240
tgctccatca cctggttcct gtcctggagc ccatgcggcg agtgctccag ggccatcacc   300
gagttcctca gccgctaccc acacgtcacc ctgttcatct acatcgccag gctctaccac   360
cacgccgacc caaggaacag gcagggcctc cgcgacctga tctccagcgg cgtgaccatc   420
caaatcatga ccgagcagga gtccggctac tgctggagga acttcgtcaa ctactcccca   480
```

```
agcaacgagg cccactggcc aaggtaccca cacctctggg tgcgcctcta cgtgctcgag    540
ctgtactgca tcatcctcgg cctgccacca tgcctcaaca tcctgaggcg caagcaacca    600
cagctgacct tcttcaccat cgccctccaa agctgccact accagaggct cccaccacac    660
atcctgtggg ctaccggcct c                                              681

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      XTEN encoding sequence

<400> SEQUENCE: 2
aagtccggca gcgagacgcc aggcacctcc gagagcgcta cgcctgaa                 48

<210> SEQ ID NO 3
<211> LENGTH: 4152
<212> TYPE: DNA
<213> ORGANISM: Artificial Sequence
<220> FEATURE:
<223> OTHER INFORMATION: Description of Artificial Sequence: Synthetic
      nCas9(D10A) encoding sequence

<400> SEQUENCE: 3
atggacaaga agtactcgat cggcctcgcc atcgggacga actcagttgg ctgggccgtg    60
atcaccgacg agtacaaggt gccctctaag aagttcaagg tcctggggaa caccgaccgc    120
cattccatca agaagaacct catcggcgct ctcctgttcg acagcgggga gaccgctgag    180
gctacgaggc tcaagagaac cgctaggcgc cggtacacga aggaagaaca ggatctgc      240 tacctccaag agattttctc caacgagatg gccaaggttg acgattcatt cttccaccgc    300
ctggaggagt ctttcctcgt ggaggaggat aagaagcacg agcggcatcc catcttcggc    360
aacatcgtgg acgaggttgc ctaccacgag aagtacccta cgatctacca tctgcggaag    420
aagctcgtgg actccaccga taaggcggac ctcagactga tctacctcgc tctggcccac    480
atgatcaagt tccgcggcca tttcctgatc gaggggatc tcaacccaga caacagcgat    540
gttgacaagc tgttcatcca actcgtgcag acctacaacc aactcttcga ggagaacccg    600
atcaacgcct ctggcgtgga cgcgaaggct atcctgtccg cgaggctctc gaagtccagg    660
aggctggaga acctgatcgc tcagctccca ggcgagaaga gaacggcct gttcgggaac    720 ctcatcgctc tcagcctggg gctcacccg aacttcaagt cgaacttcga tctcgctgag    780
gacgccaagc tgcaactctc caaggacacc tacgacgatg acctcgataa cctcctggcc    840
cagatcggcg atcaatacgc ggacctgttc ctcgctgcca gaaacctgtc ggacgccatc    900
ctcctgtcag atatcctccg cgtgaacacc gagatcacga aggctccact ctctgcctcc    960
atgatcaagc gctacgacga gcaccatcag gatctgaccc tcctgaaggc gctggtccgc    1020
caacagctcc cggagaagta caaggagatt ttcttcgatc agtcgaagaa cggctacgct    1080
gggtacatcg acggcggggc ctcacaagag gagttctaca gttcatcaa gccaatcctg    1140 gagaagatgg acggcacgga ggagctcctg gtgaagctca caggagga cctcctgcgg    1200 aagcagagaa ccttcgataa cggcagcatc ccccaccaaa tccatctcgg ggagctgcac    1260
gccatcctga aaggcaaga ggacttctac ccttttcctca aggataaccg ggagaagatc    1320
gagaagatcc tgaccttcag aatcccatac tacgtcggcc ctctcgcgcg ggggaactca    1380
```

-continued

```
agattcgctt ggatgacccg caagtctgag gagaccatca cgccgtggaa cttcgaggag    1440
gtggtggaca agggcgctag cgctcagtcg ttcatcgaga ggatgaccaa cttcgacaag    1500
aacctgccca acgagaaggt gctccctaag cactcgctcc tgtacgagta cttcaccgtc    1560
tacaacgagc tcacgaaggt gaagtacgtc accgagggca tgcgcaagcc agcgttcctg    1620
tccggggagc agaagaaggc tatcgtggac ctcctgttca agaccaaccg gaaggtcacg    1680
gttaagcaac tcaaggagga ctacttcaag aagatcgagt gcttcgattc ggtcgagatc    1740
agcggcgttg aggaccgctt caacgccagc ctcgggacct accacgatct cctgaagatc    1800
atcaaggata aggacttcct ggacaacgag gagaacgagg atatcctgga ggacatcgtg    1860
ctgaccctca cgctgttcga ggacagggag atgatcgagg agcgcctgaa gacgtacgcc    1920
catctcttcg atgacaaggt catgaagcaa ctcaagcgcc ggagatacac cggctgggg    1980 aggctgtccc gcaagctcat caacggcatc cgggacaagc agtccgggaa gaccatcctc    2040
gacttcctca gagcgatgg cttcgccaac aggaacttca tgcaactgat ccacgatgac    2100
agcctcacct tcaaggagga tatccaaaag gctcaagtga gcggccaggg ggactcgctg    2160
cacgagcata tcgcgaacct cgctggctcc ccgcgatca agaagggcat cctccagacc    2220
gtgaaggttg tggacgagct cgtgaaggtc atgggccggc acaagcctga gaacatcgtc    2280
atcgagatgg ccagagagaa ccaaaccacg cagaaggggc aaaagaactc tagggagcgc    2340
atgaagcgca tcgaggaggg catcaaggag ctggggtccc aaatcctcaa ggagcaccca    2400
gtggagaaca cccaactgca gaacgagaag ctctacctgt actacctcca gaacggcagg    2460
gatatgtacg tggaccaaga gctggatatc aaccgcctca gcgattacga cgtcgatcat    2520
atcgttcccc agtctttcct gaaggatgac tccatcgaca acaaggtcct caccaggtcg    2580
gacaagaacc gcggcaagtc agataacgtt ccatctgagg aggtcgttaa gaagatgaag    2640
aactactgga ggcagctcct gaacgccaag ctgatcacgc aaaggaagtt cgacaacctc    2700
accaaggctg agagaggcgg gctctcagag ctggacaagg ccggcttcat caagcggcag    2760
ctggtcgaga ccagacaaat cacgaagcac gttgcgcaaa tcctcgactc tcggatgaac    2820
acgaagtacg atgagaacga caagctgatc agggaggtta aggtgatcac cctgaagtct    2880
aagctcgtct ccgacttcag gaaggatttc cagttctaca aggttcgcga gatcaacaac    2940
taccaccatg cccatgacgc ttacctcaac gctgtggtcg gcaccgctct gatcaagaag    3000
tacccaaagc tggagtccga gttcgtgtac ggggactaca aggtttacga tgtgcgcaag    3060
atgatcgcca gtcggagca agagatcggc aaggctaccg ccaagtactt cttctactca    3120
aacatcatga acttcttcaa gaccgagatc acgctggcca acggcgagat ccggaagaga    3180
ccgctcatcg agaccaacgg cgagacgggg gagatcgtgt gggacaaggg cagggatttc    3240
gcgaccgtcc gcaaggttct ctccatgccc caggtgaaca tcgtcaagaa gaccgaggtc    3300
caaacgggcg ggttctcaaa ggagtctatc ctgcctaagc ggaacagcga caagctcatc    3360
gccagaaaga aggactggga cccaaagaag tacggcgggt tcgacagccc taccgtggcc    3420
tactcggtcc tggttgtggc gaaggttgag aagggcaagt ccaagaagct caagagcgtg    3480
aaggagctcc tggggatcac catcatggag aggtccagct cgagaagaa cccaatcgac    3540 ttcctggagg ccaagggcta caaggaggtg aagaaggacc tgatcatcaa gctcccgaag    3600
tactctctct tcgagctgga gaacggcagg aagagaatgc tggcttccgc tggcgagctc    3660
cagaagggga cgagctcgc gctgccaagc aagtacgtga acttcctcta cctggcttcc    3720
cactacgaga agctcaaggg cagcccggag gacaacgagc aaaagcagct gttcgtcgag    3780
```

-continued

```
cagcacaagc attacctcga cgagatcatc gagcaaatct ccgagttcag caagcgcgtg    3840
atcctcgccg acgcgaacct ggataaggtc ctctccgcct acaacaagca ccgggacaag    3900
cccatcagag agcaagcgga gaacatcatc catctcttca ccctgacgaa cctcggcgct    3960
cctgctgctt tcaagtactt cgacaccacg atcgatcgga agagatacac ctccacgaag    4020
gaggtcctgg acgcgaccct catccaccag tcgatcaccg gcctgtacga cgaggatc     4080 gacctctcac aactcggcgg ggataagaga cccgcagcaa ccaagaaggc agggcaagca    4140
aagaagaaga ag                                                        4152
```

<210> SEQ ID NO 4
<211> LENGTH: 4152
<212> TYPE: DNA
<213> ORGANISM: Artificial Sequence
<220> FEATURE:
<223> OTHER INFORMATION: Description of Artificial Sequence: Synthetic dCas9 encoding sequence

<400> SEQUENCE: 4

```
atggacaaga agtactcgat cggcctcgcc atcgggacga actcagttgg ctgggccgtg     60
atcaccgacg agtacaaggt gccctctaag aagttcaagg tcctggggaa caccgaccgc    120
cattccatca agaagaacct catcggcgct ctcctgttcg acagcgggga gaccgctgag    180
gctacgaggc tcaagagaac cgctaggcgc cggtacacga agaagaagaa caggatctgc    240
tacctccaag agattttctc aacgagatg gccaaggttg acgattcatt cttccaccgc    300
ctggaggagt ctttcctcgt ggaggaggat aagaagcacg agcggcatcc catcttcggc    360
aacatcgtgg acgaggttgc ctaccacgag aagtacccta cgatctacca tctgcggaag    420
aagctcgtga ctccaccga taaggcggac ctcagactga tctacctcgc tctggcccac    480
atgatcaagt ccgcggcca tttcctgatc gaggggatc tcaacccaga caacagcgat    540
gttgacaagc tgttcatcca actcgtgcag acctacaacc aactcttcga ggagaacccg    600
atcaacgcct ctggcgtgga cgcgaaggct atcctgtccg cgaggctctc gaagtccagg    660
aggctggaga acctgatcgc tcagctccca ggcgagaaga gaacggcct gttcgggaac    720 ctcatcgctc tcagcctggg gctcacccg aacttcaagt cgaacttcga tctcgctgag    780
gacgccaagc tgcaactctc caaggacacc tacgacgatg acctcgataa cctcctggcc    840
cagatcggcg atcaatacgc ggacctgttc ctcgctgcca gaaacctgtc ggacgccatc    900
ctcctgtcag atatcctccg cgtgaacacc gagatcacga aggctccact ctctgcctcc    960
atgatcaagc gctacgacga gcaccatcag gatctgaccc tcctgaaggc gctggtccgc   1020
caacagctcc cggagaagta caaggagatt ttcttcgatc agtcgaagaa cggctacgct   1080
gggtacatcg acggcgggc ctcacaagag gagttctaca gttcatcaa gccaatcctg   1140 gagaagatgg acggcacgga ggagctcctg gtgaagctca caggagga cctcctgcgg   1200 aagcagagaa ccttcgataa cggcagcatc ccccaccaaa tccatctcgg ggagctgcac   1260
gccatcctga aaggcaaga ggacttctac cctttcctca aggataaccg ggagaagatc   1320
gagaagatcc tgaccttcag aatcccatac acgtcggcc ctctcgcgcg ggggaactca   1380
agattcgctt ggatgacccg caagtctgag gagaccatca cgccgtggaa cttcgaggag   1440
gtggtggaca agggcgctag cgctcagtcg ttcatcgaga ggatgaccaa cttcgacaag   1500
aacctgccca cgagaaggt gctccctaag cactcgctcc tgtacgagta cttcaccgtc   1560
tacaacgagc tcacgaaggt gaagtacgtc accgagggca tgcgcaagcc agcgttcctg   1620
```

```
tccggggagc agaagaaggc tatcgtggac ctcctgttca agaccaaccg gaaggtcacg   1680
gttaagcaac tcaaggagga ctacttcaag aagatcgagt gcttcgattc ggtcgagatc   1740
agcggcgttg aggaccgctt caacgccagc ctcgggacct accacgatct cctgaagatc   1800
atcaaggata aggacttcct ggacaacgag gagaacgagg atatcctgga ggacatcgtg   1860
ctgaccctca cgctgttcga ggacagggag atgatcgagg agcgcctgaa gacgtacgcc   1920
catctcttcg atgacaaggt catgaagcaa ctcaagcgcc ggagatacac cggctggggg   1980
aggctgtccc gcaagctcat caacggcatc cggacaagc agtccgggaa gaccatcctc   2040
gacttcctca gagcgatgg cttcgccaac aggaacttca tgcaactgat ccacgatgac   2100
agcctcacct tcaaggagga tatccaaaag gctcaagtga gcggccaggg ggactcgctg   2160
cacgagcata tcgcgaacct cgctggctcc cccgcgatca agaagggcat cctccagacc   2220
gtgaaggttg tggacgagct cgtgaaggtc atgggccggc acaagcctga aacatcgtc   2280 atcgagatgg ccagagagaa ccaaaccacg cagaaggggc aaaagaactc tagggagcgc   2340
atgaagcgca tcgaggaggg catcaaggag ctggggtccc aaatcctcaa ggagcaccca   2400
gtggagaaca cccaactgca gaacgagaag ctctacctgt actacctcca gaacggcagg   2460
gatatgtacg tggaccaaga gctggatatc aaccgcctca gcgattacga cgtcgatgct   2520
atcgttcccc agtctttcct gaaggatgac tccatcgaca caaggtcct caccaggtcg   2580 gacaagaacc gcggcaagtc agataacgtt ccatctgagg aggtcgttaa gaagatgaag   2640
aactactgga ggcagctcct gaacgccaag ctgatcacgc aaaggaagtt cgacaacctc   2700
accaaggctg agagaggcgg gctctcagag ctggacaagg ccggcttcat caagcggcag   2760
ctggtcgaga ccagacaaat cacgaagcac gttgcgcaaa tcctcgactc tcggatgaac   2820
acgaagtacg atgagaacga caagctgatc agggaggtta aggtgatcac cctgaagtct   2880
aagctcgtct ccgacttcag gaaggatttc cagttctaca aggttcgcga gatcaacaac   2940
taccaccatg cccatgacgc ttacctcaac gctgtggtcg gcaccgctct gatcaagaag   3000
tacccaaagc tggagtccga gttcgtgtac ggggactaca aggtttacga tgtgcgcaag   3060
atgatcgcca agtcggagca agagatcggc aaggctaccg ccaagtactt cttctactca   3120
aacatcatga acttcttcaa gaccgagatc acgctggcca acggcgagat ccggaagaga   3180
ccgctcatcg agaccaacgg cgagacgggg gagatcgtgt gggacaaggg cagggatttc   3240
gcgaccgtcc gcaaggttct ctccatgccc caggtgaaca tcgtcaagaa gaccgaggtc   3300
caaacgggcg ggttctcaaa ggagtctatc ctgcctaagc ggaacagcga caagctcatc   3360
gccagaaaga aggactggga cccaaagaag tacggcgggt tcgacagccc taccgtggcc   3420
tactcggtcc tggttgtggc gaaggttgag aagggcaagt ccaagaagct caagagcgtg   3480
aaggagctcc tggggatcac catcatggag aggtccagct tcgagaagaa cccaatcgac   3540
ttcctggagg ccaagggcta caaggaggtg aagaaggacc tgatcatcaa gctcccgaag   3600
tactctctct tcgagctgga gaacggcagg aagagaatgc tggcttccgc tggcgagctc   3660
cagaagggga cgagctcgc gctgccaagc aagtacgtga acttcctcta cctggcttcc   3720
cactacgaga agctcaaggg cagcccggag gacaacgagc aaaagcagct gttcgtcgag   3780
cagcacaagc attacctcga cgagatcatc gagcaaatct ccgagttcag caagcgcgtg   3840
atcctcgccg acgcgaacct ggataaggtc ctctccgcct acaacaagca ccgggacaag   3900
cccatcagag agcaagcgga gaacatcatc catctcttca ccctgacgaa cctcggcgct   3960
```

```
cctgctgctt tcaagtactt cgacaccacg atcgatcgga agagatacac ctccacgaag    4020
gaggtcctgg acgcgaccct catccaccag tcgatcaccg gcctgtacga gacgaggatc    4080
gacctctcac aactcggcgg ggataagaga cccgcagcaa ccaagaaggc agggcaagca    4140
aagaagaaga ag                                                        4152

<210> SEQ ID NO 5
<211> LENGTH: 249
<212> TYPE: DNA
<213> ORGANISM: Artificial Sequence
<220> FEATURE:
<223> OTHER INFORMATION: Description of Artificial Sequence: Synthetic
      UGI encoding sequence

<400> SEQUENCE: 5
accaacctgt ccgacatcat cgagaaggag acgggcaagc aactcgtgat ccaggagagc      60
atcctcatgc tgccagagga ggtggaggag gtcatcggca acaagccaga gtccgacatc     120
ctggtgcaca ccgcctacga cgagtccacc gacgagaacg tcatgctcct gaccagcgac     180
gccccagagt acaagccatg ggccctcgtc atccaggaca gcaacgggga gaacaagatc     240
aagatgctg                                                             249

<210> SEQ ID NO 6
<211> LENGTH: 720
<212> TYPE: DNA
<213> ORGANISM: Artificial Sequence
<220> FEATURE:
<223> OTHER INFORMATION: Description of Artificial Sequence: Synthetic
      GFP encoding sequence

<400> SEQUENCE: 6
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 7
<211> LENGTH: 720
<212> TYPE: DNA
<213> ORGANISM: Artificial Sequence
<220> FEATURE:
<223> OTHER INFORMATION: Description of Artificial Sequence: Synthetic
      BFPm encoding sequence

<400> SEQUENCE: 7
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
```

| | |
|---|---|
| ggcaagctga cccctgaagtt catctgcacc accggcaagc tgcccgtgcc ctggcccacc | 180 |
| ctcgtgacca ccttcaccca cggcgtgcgg tgcttcagcc gctacccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actcacggca tggacgagct gtacaagtaa | 720 |

<210> SEQ ID NO 8
<211> LENGTH: 5696
<212> TYPE: DNA
<213> ORGANISM: Artificial Sequence
<220> FEATURE:
<223> OTHER INFORMATION: Description of Artificial Sequence: Synthetic
      pUbi-GFP vector

<400> SEQUENCE: 8

| | |
|---|---|
| gagctcggta cctgacccgg tcgtgcccct ctctagagat aatgagcatt gcatgtctaa | 60 |
| gttataaaaa attaccacat atttttttg tcacacttgt ttgaagtgca gtttatctat | 120 |
| ctttatacat atatttaaac tttactctac gaataatata atctatagta ctacaataat | 180 |
| atcagtgttt tagagaatca tataaatgaa cagttagaca tggtctaaag gacaattgag | 240 |
| tattttgaca acaggactct acagttttat cttttagtg tgcatgtgtt ctcctttttt | 300 |
| tttgcaaata gcttcaccta tataatactt catccatttt attagtacat ccatttaggg | 360 |
| tttaggggtta atggttttta tagctaatt ttttagtac atctatttta ttctatttta | 420 |
| gcctctaaat taagaaaact aaaactctat tttagttttt ttatttaata atttagatat | 480 |
| aaaatagaat aaaataaagt gactaaaaat taaacaaata ccctttaaga aattaaaaaa | 540 |
| actaaggaaa cattttttctt gtttcgagta gataatgcca gcctgttaaa cgccgtcgac | 600 |
| gagtctaacg gacaccaacc agcgaaccag cagcgtcgcg tcgggccaag cgaagcagac | 660 |
| ggcacggcat ctctgtcgct gcctctggac ccctctcgat cgagagttcc gctccaccgt | 720 |
| tggacttgct ccgctgtcgg catccagaaa ttgcgtggcg gagcggcaga cgtgagccgg | 780 |
| cacggcaggc ggcctcctcc tcctctcacg gcaccggcag ctacggggga ttcctttccc | 840 |
| accgctcctt cgctttcccct tcctcgcccg ccgtaataaa tagacacccc ctccacaccc | 900 |
| tctttcccca acctcgtgtt gttcggagcg cacacacaca caaccagatc tcccccaaat | 960 |
| ccacccgtcg caacctccgc ttcaaggtac gccgctcgtc ctcccccccc ccccctctct | 1020 |
| accttctcta gatcggcgtt ccggtccatg gttagggccc ggtagttcta cttctgttca | 1080 |
| tgttttgtgtt agatccgtgt ttgtgttaga tccgtgctgc tagcgttcgt acacggatgc | 1140 |
| gacctgtacg tcagacacgt tctgattgct aacttgccag tgtttctctt tggggaatcc | 1200 |
| tgggatggct ctagccgttc cgcagacggg atcgatttca tgattttttt tgtttcgttg | 1260 |
| catagggttt ggtttgccct tttcctttat ttcaatatat gccgtgcact tgtttgtcgg | 1320 |
| gtcatctttt catgcttttt tttgtcttgg ttgtgatgat gtggtctggt tgggcggtcg | 1380 |
| ttctagatcg gagtagaatt aattctgttt caaactacct ggtggattta ttaatttgg | 1440 |

-continued

```
atctgtatgt gtgtgccata catattcata gttacgaatt gaagatgatg gatggaaata    1500
tcgatctagg ataggtatac atgttgatgc gggtttttact gatgcatata cagagatgct   1560
ttttgttcgc ttggttgtga tgatgtggtg tggttgggcg gtcgttcatt cgttctagat    1620
cggagtagaa tactgtttca aactacctgg tgtatttatt aattttggaa ctgtatgtgt    1680
gtgtcataca tcttcatagt tacgagttta agatggatgg aaatatcgat ctaggatagg    1740
tatacatgtt gatgtgggtt ttactgatgc atatacatga tggcatatgc agcatctatt   1800
catatgctct aaccttgagt acctatctat tataataaac aagtatgttt tataattatt    1860
ttgatcttga tatacttgga tgatggcata tgcagcagct atatgtggat ttttttagcc    1920
ctgccttcat acgctattta tttgcttggt actgtttctt ttgtcgatgc tcaccctgtt    1980
gtttggtgtt acttctgcaa agcttccacc atggcgtgca ggtcgactct agaggatcca    2040
tggtgagcaa gggcgaggag ctgttcaccg gggtggtgcc catcctggtc gagctggacg    2100
gcgacgtaaa cggccacaag ttcagcgtgt ccggcgaggg cgagggcgat gccacctacg    2160
gcaagctgac cctgaagttc atctgcacca ccggcaagct gcccgtgccc tggcccaccc    2220
tcgtgaccac cttcacctac ggcgtgcagt gcttcagccg ctaccccgac cacatgaagc    2280
agcacgactt cttcaagtcc gccatgcccg aaggctacgt ccaggagcgc accatcttct    2340
tcaaggacga cggcaactac aagacccgcg ccgaggtgaa gttcgagggc gacaccctgg    2400
tgaaccgcat cgagctgaag ggcatcgact tcaaggagga cggcaacatc ctggggcaca    2460
agctggagta caactacaac agccacaacg tctatatcat ggccgacaag cagaagaacg    2520
gcatcaaggt gaacttcaag atccgccaca acatcgagga cggcagcgtg cagctcgccg    2580
accactacca gcagaacacc cccatcggcg acggccccgt gctgctgccc gacaaccact    2640
acctgagcac ccagtccgcc ctgagcaaag accccaacga gaagcgcgat cacatggtcc    2700
tgctggagtt cgtgaccgcc gccgggatca ctcacggcat ggacgagctg tacaagtaac    2760
cgggcgagct cgaattcgct gaaatcacca gtctctctct acaaatctat ctctctctat    2820
tttctccata ataatgtgt gagtagtttc ccgataaggg aaattagggt tcttataggg     2880
tttcgctcat gtgttgagca tataagaaac ccttagtatg tatttgtatt tgtaaaatac    2940
ttctatcaat aaaatttcta attcctaaaa ccaaaatcca gtactaaaat ccagatctcc    3000
taaagtccct atagatcttt gtcgtgaata taaaccagac acgagacgac taaacctgga    3060
gcccagacgc cgttcgaagc tagaagtacc gcttaggcag gaggccgtta gggaaaagat    3120
gctaaggcag ggttggttac gttgactccc ccgtaggttt ggtttaaata tgatgaagtg    3180
gacggaagga aggaggaaga caaggaagga taaggttgca ggccctgtgc aaggtaagaa    3240
gatggaaatt tgatagaggt acgctactat acttatacta tacgctaagg gaatgcttgt    3300
atttataccc tataccccct aataacccct tatcaattta agaaataatc cgcataagcc    3360
cccgcttaaa aattggtatc agagccatga ataggtctat gaccaaaact caagaggata    3420
aaacctcacc aaaatacgaa agagttctta actctaaaga taaagatct ttcaagatca     3480
aaactagttc cctcacaccg gagcatgcga tatcctcgag agatctaggc gtaatcatgg    3540
tcatagctgt ttcctgtgtg aaattgttat ccgctcacaa ttccacacaa catacgagcc    3600
ggaagcataa agtgtaaagc ctggggtgcc taatgagtga gctaactcac attaattgcg    3660
ttgcgctcac tgcccgcttt ccagtcggga aacctgtcgt gccagctgca ttaatgaatc    3720
ggccaacgcg cggggagagg cggtttgcgt attgggcgct cttccgcttc ctcgctcact    3780
gactcgctgc gctcggtcgt tcggctgcgg cgagcggtat cagctcactc aaaggcggta    3840
```

| | |
|---|---|
| atacggttat ccacagaatc aggggataac gcaggaaaga acatgtgagc aaaaggccag | 3900 |
| caaaaggcca ggaaccgtaa aaaggccgcg ttgctggcgt ttttccatag gctccgcccc | 3960 |
| cctgacgagc atcacaaaaa tcgacgctca agtcagaggt ggcgaaaccc gacaggacta | 4020 |
| taaagatacc aggcgtttcc ccctggaagc tccctcgtgc gctctcctgt tccgaccctg | 4080 |
| ccgcttaccg gatacctgtc cgcctttctc ccttcgggaa gcgtggcgct ttctcaatgc | 4140 |
| tcacgctgta ggtatctcag ttcggtgtag gtcgttcgct ccaagctggg ctgtgtgcac | 4200 |
| gaaccccccg ttcagcccga ccgctgcgcc ttatccggta actatcgtct tgagtccaac | 4260 |
| ccggtaagac acgacttatc gccactggca gcagccactg gtaacaggat tagcagagcg | 4320 |
| aggtatgtag gcggtgctac agagttcttg aagtggtggc ctaactacgg ctacactaga | 4380 |
| aggacagtat ttggtatctg cgctctgctg aagccagtta ccttcggaaa aagagttggt | 4440 |
| agctcttgat ccggcaaaca aaccaccgct ggtagcggtg gtttttttgt ttgcaagcag | 4500 |
| cagattacgc gcagaaaaaa aggatctcaa gaagatcctt tgatcttttc tacggggtct | 4560 |
| gacgctcagt ggaacgaaaa ctcacgttaa gggattttgg tcatgagatt atcaaaaagg | 4620 |
| atcttcacct agatcctttt aaattaaaaa tgaagtttta aatcaatcta agtatatat | 4680 |
| gagtaaactt ggtctgacag ttaccaatgc ttaatcagtg aggcacctat ctcagcgatc | 4740 |
| tgtctatttc gttcatccat agttgcctga ctccccgtcg tgtagataac tacgatacgg | 4800 |
| gagggcttac catctggccc cagtgctgca atgataccgc gagacccacg ctcaccggct | 4860 |
| ccagatttat cagcaataaa ccagccagcc ggaagggccg agcgcagaag tggtcctgca | 4920 |
| actttatccg cctccatcca gtctattaat tgttgccggg aagctagagt aagtagttcg | 4980 |
| ccagttaata gtttgcgcaa cgttgttgcc attgctacag gcatcgtggt gtcacgctcg | 5040 |
| tcgtttggta tggcttcatt cagctccggt tcccaacgat caaggcgagt tacatgatcc | 5100 |
| cccatgttgt gcaaaaaagc ggttagctcc ttcggtcctc cgatcgttgt cagaagtaag | 5160 |
| ttggccgcag tgttatcact catggttatg gcagcactgc ataattctct tactgtcatg | 5220 |
| ccatccgtaa gatgcttttc tgtgactggt gagtactcaa ccaagtcatt ctgagaatag | 5280 |
| tgtatgcggc gaccgagttg ctcttgcccg gcgtcaatac gggataatac cgcgccacat | 5340 |
| agcagaactt taaaagtgct catcattgga aaacgttctt cggggcgaaa actctcaagg | 5400 |
| atcttaccgc tgttgagatc cagttcgatg taacccactc gtgcacccaa ctgatcttca | 5460 |
| gcatctttta ctttcaccag cgtttctggg tgagcaaaaa caggaaggca aaatgccgca | 5520 |
| aaaaagggaa taagggcgac acggaaatgt tgaatactca tactcttcct ttttcaatat | 5580 |
| tattgaagca tttatcaggg ttattgtctc atgagcggat acatatttga atgtatttag | 5640 |
| aaaaataaac aaataggggt tccgcgcaca tttccccgaa aagtgccacc tgacgt | 5696 |

<210> SEQ ID NO 9
<211> LENGTH: 5696
<212> TYPE: DNA
<213> ORGANISM: Artificial Sequence
<220> FEATURE:
<223> OTHER INFORMATION: Description of Artificial Sequence: Synthetic
    pUbi-BFPm vector

<400> SEQUENCE: 9

| | |
|---|---|
| gagctcggta cctgacccgg tcgtgcccct ctctagagat aatgagcatt gcatgtctaa | 60 |
| gttataaaaa attaccacat attttttttg tcacacttgt ttgaagtgca gtttatctat | 120 |
| ctttatacat atatttaaac tttactctac gaataatata atctatagta ctacaataat | 180 |

```
atcagtgttt tagagaatca tataaatgaa cagttagaca tggtctaaag gacaattgag    240
tattttgaca acaggactct acagttttat cttttagtg tgcatgtgtt ctccttttt     300 tttgcaaata gcttcaccta tataatactt catccatttt attagtacat ccatttaggg    360
tttagggtta atggttttta tagactaatt tttagtac atctatttta ttctatttta     420
gcctctaaat taagaaaact aaaactctat tttagttttt ttatttaata atttagatat    480
aaaatagaat aaaataaagt gactaaaaat taaacaaata ccctttaaga aattaaaaaa    540
actaaggaaa cattttcct gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgat cgagagttcc gctccaccgt    720
tggacttgct ccgctgtcgg catccagaaa ttgcgtggcg gagcggcaga cgtgagccgg    780
cacggcaggc ggcctcctcc tcctctcacg gcaccggcag ctacggggga ttccttccc     840 accgctcctt cgctttccct tcctcgcccg ccgtaataaa tagacacccc ctccacaccc    900
tctttcccca acctcgtgtt gttcggagcg cacacacaca caaccagatc tcccccaaat    960
ccacccgtcg gcacctccgc ttcaaggtac gccgctcgtc ctccccccc ccccctctct   1020 accttctcta gatcggcgtt ccggtccatg gttagggccc ggtagttcta cttctgttca   1080
tgtttgtgtt agatccgtgt ttgtgttaga tccgtgctgc tagcgttcgt acacggatgc   1140
gacctgtacg tcagacacgt tctgattgct aacttgccag tgtttctctt tggggaatcc   1200
tgggatggct ctagccgttc cgcagacggg atcgatttca tgattttttt tgtttcgttg   1260
catagggttt ggtttgccct tttccttat ttcaatatat gccgtgcact tgttgtcgg    1320 gtcatctttt catgcttttt ttgtcttgg ttgtgatgat gtggtctggt tgggcggtcg   1380
ttctagatcg gagtagaatt aattctgttt caaactacct ggtggattta ttaattttgg   1440
atctgtatgt gtgtgccata catattcata gttacgaatt gaagatgatg gatggaaata   1500
tcgatctagg ataggtatac atgttgatgc gggttttact gatgcatata cagagatgct   1560
ttttgttcgc ttggttgtga tgatgtggtg tggttgggcg tcgttcatt cgttctagat   1620 cggagtagaa tactgtttca aactacctgg tgtatttatt aatttggaa ctgtatgtgt   1680 gtgtcataca tcttcatagt tacgagttta agatggatgg aaatatcgat ctaggatagg   1740
tatacatgtt gatgtgggtt ttactgatgc atatacatga tggcatatgc agcatctatt   1800
catatgctct aaccttgagt acctatctat tataataaac aagtatgttt tataattatt   1860
ttgatcttga tatacttgga tgatggcata tgcagcagct atatgtggat ttttttagcc   1920
ctgccttcat acgctatttta tttgcttggt actgtttctt ttgtcgatgc tcaccctgtt   1980
gtttggtgtt acttctgcaa agcttccacc atggcgtgca ggtcgactct agaggatcca   2040
tggtgagcaa gggcgaggag ctgttcaccg ggtggtgcc catcctggtc gagctggacg   2100
gcgacgtaaa cggccacaag ttcagcgtgt ccggcgaggg cgaggcgat gccacctacg   2160 gcaagctgac cctgaagttc atctgcacca ccggcaagct gcccgtgccc tggcccaccc   2220
tcgtgaccac cttcacccac ggcgtgcggt gcttcagccg ctaccccgac cacatgaagc   2280
agcacgactt cttcaagtcc gccatgcccg aaggctacgt ccaggagcgc accatcttct   2340
tcaaggacga cggcaactac aagacccgcg ccgaggtgaa gttcgagggc gacaccctgg   2400
tgaaccgcat cgagctgaag ggcatcgact tcaaggagga cggcaacatc ctggggcaca   2460
agctggagta caactacaac agccacaacg tctatatcat ggccgacaag cagaagaacg   2520
```

-continued

```
gcatcaaggt gaacttcaag atccgccaca acatcgagga cggcagcgtg cagctcgccg    2580
accactacca gcagaacacc cccatcggcg acggccccgt gctgctgccc gacaaccact    2640
acctgagcac ccagtccgcc ctgagcaaag accccaacga gaagcgcgat cacatggtcc    2700
tgctggagtt cgtgaccgcc gccgggatca ctcacggcat ggacgagctg tacaagtaac    2760
cgggcgagct cgaattcgct gaaatcacca gtctctctct acaaatctat ctctctctat    2820
tttctccata aataatgtgt gagtagtttc ccgataaggg aaattagggt tcttataggg    2880
tttcgctcat gtgttgagca tataagaaac ccttagtatg tatttgtatt tgtaaaatac    2940
ttctatcaat aaaatttcta attcctaaaa ccaaaatcca gtactaaaat ccagatctcc    3000
taaagtccct atagatcttt gtcgtgaata taaaccagac acgagacgac taaacctgga    3060
gcccagacgc cgttcgaagc tagaagtacc gcttaggcag gaggccgtta gggaaaagat    3120
gctaaggcag ggttggttac gttgactccc ccgtaggttt ggtttaaata tgatgaagtg    3180
gacggaagga aggaggaaga caaggaagga taaggttgca ggccctgtgc aaggtaagaa    3240
gatggaaatt tgatagaggt acgctactat acttatacta tacgctaagg gaatgcttgt    3300
atttataccc tataccccct aataacccct tatcaattta agaaataatc cgcataagcc    3360
cccgcttaaa aattggtatc agagccatga ataggtctat gaccaaaact caagaggata    3420
aaacctcacc aaaatacgaa agagttctta actctaaaga taaagatct ttcaagatca    3480
aaactagttc cctcacaccg gagcatgcga tatcctcgag agatctaggc gtaatcatgg    3540
tcatagctgt ttcctgtgtg aaattgttat ccgctcacaa ttccacacaa catacgagcc    3600
ggaagcataa agtgtaaagc ctggggtgcc taatgagtga gctaactcac attaattgcg    3660
ttgcgctcac tgcccgcttt ccagtcggga acctgtcgt gccagctgca ttaatgaatc    3720
ggccaacgcg cggggagagg cggtttgcgt attgggcgct cttccgcttc ctcgctcact    3780
gactcgctgc gctcggtcgt tcggctgcgg cgagcggtat cagctcactc aaaggcggta    3840
atacggttat ccacagaatc aggggataac gcaggaaaga acatgtgagc aaaaggccag    3900
caaaaggcca ggaaccgtaa aaaggccgcg ttgctggcgt ttttccatag gctccgcccc    3960
cctgacgagc atcacaaaaa tcgacgctca agtcagaggt ggcgaaaccc gacaggacta    4020
taaagatacc aggcgtttcc ccctggaagc tccctcgtgc gctctcctgt tccgaccctg    4080
ccgcttaccg gatacctgtc cgcctttctc ccttcgggaa gcgtggcgct ttctcaatgc    4140
tcacgctgta ggtatctcag ttcggtgtag tcgttcgct ccaagctggg ctgtgtgcac    4200
gaacccccg ttcagcccga ccgctgcgcc ttatccggta actatcgtct tgagtccaac    4260
ccggtaagac acgacttatc gccactggca gcagccactg gtaacaggat tagcagagcg    4320
aggtatgtag gcggtgctac agagttcttg aagtggtggc ctaactacgg ctacactaga    4380
aggacagtat ttggtatctg cgctctgctg aagccagtta ccttcggaaa aagagttggt    4440
agctcttgat ccggcaaaca aaccaccgct ggtagcggtg gttttttgt ttgcaagcag    4500
cagattacgc gcagaaaaaa aggatctcaa gaagatcctt tgatcttttc tacgggtct    4560
gacgctcagt ggaacgaaaa ctcacgttaa gggattttgg tcatgagatt atcaaaaagg    4620
atcttcacct agatcctttt aaattaaaaa tgaagtttta aatcaatcta agtatatat    4680
gagtaaactt ggtctgacag ttaccaatgc ttaatcagtg aggcacctat ctcagcgatc    4740
tgtctatttc gttcatccat agttgcctga ctccccgtcg tgtagataac tacgatacgg    4800
gagggcttac catctggccc cagtgctgca atgataccgc gagacccacg ctcaccggct    4860
ccagatttat cagcaataaa ccagccagcc ggaagggccg agcgcagaag tggtcctgca    4920
```

```
actttatccg cctccatcca gtctattaat tgttgccggg aagctagagt aagtagttcg    4980
ccagttaata gtttgcgcaa cgttgttgcc attgctacag gcatcgtggt gtcacgctcg    5040
tcgtttggta tggcttcatt cagctccggt tcccaacgat caaggcgagt tacatgatcc    5100
cccatgttgt gcaaaaaagc ggttagctcc ttcggtcctc cgatcgttgt cagaagtaag    5160
ttggccgcag tgttatcact catggttatg gcagcactgc ataattctct tactgtcatg    5220
ccatccgtaa gatgcttttc tgtgactggt gagtactcaa ccaagtcatt ctgagaatag    5280
tgtatgcggc gaccgagttg ctcttgcccg gcgtcaatac gggataatac cgcgccacat    5340
agcagaactt taaaagtgct catcattgga aaacgttctt cggggcgaaa actctcaagg    5400
atcttaccgc tgttgagatc cagttcgatg taacccactc gtgcacccaa ctgatcttca    5460
gcatctttta ctttcaccag cgtttctggg tgagcaaaaa caggaaggca aaatgccgca    5520
aaaaagggaa taagggcgac acggaaatgt tgaatactca tactcttcct ttttcaatat    5580
tattgaagca tttatcaggg ttattgtctc atgagcggat acatatttga atgtatttag    5640
aaaaataaac aaataggggt tccgcgcaca tttccccgaa aagtgccacc tgacgt        5696

<210> SEQ ID NO 10
<211> LENGTH: 3514
<212> TYPE: DNA
<213> ORGANISM: Artificial Sequence
<220> FEATURE:
<223> OTHER INFORMATION: Description of Artificial Sequence: Synthetic
      pUC57-APOBEC1-XTEN-UGI vector

<400> SEQUENCE: 10
cgacgtagcc acctactccc aacatcagcc ggactccgat tacctcggga acttgctccg      60
tagtaagaca ttcatcgcgc ttgctgcctt cgaccaagaa gcggttgttg gcgctctcgc     120
ggcttacgtt ctgcccaggt ttgagcagcc gcgtagtgag atctatatct atgatctcgc     180
agtctccggc gagcaccgga ggcagggcat tgccaccgcg ctcatcaatc tcctcaagca     240
tgaggccaac gcgcttggtg cttatgtgat ctacgtgcaa gcagattacg gtgacgatcc     300
cgcagtggct ctctatacaa agtgggcat acgggaagaa gtgatgcact ttgatatcga     360
cccaagtacc gccacctaac aattcgttca agccgagatc ggcttcccgg ccgcggagtt     420
gttcggtaaa ttgtcacaac gccgctcatg acattaacct ataaaaatag gcgtatcacg     480
aggcccttttt gtctcgcgcg tttcggtgat gacggtgaaa acctctgaca catgcagctc     540
ccggagaagg tcacagcttg tctgtaagcg gatgccggga gcagacaagc ccgtcagggc     600
gcgtcagcgg gtgttggcgg gtgtcggggc tggcttaact atgcggcatc agagcagatt     660
gtactgagag tgcaccatat gcggtgtgaa ataccgcaca gatgcgtaag gagaaaatac     720
cgcatcaggc gccattcgcc attcaggctg cgcaactgtt gggaagggcg atcggtgcgg     780
gcctcttcgc tattacgcca gctggcgaaa ggggatgtg ctgcaaggcg attaagttgg     840
gtaacgccag ggttttccca gtcacgacgt tgtaaaacga cggccagtga attcgagctc     900
ggtacctcgc gaatgccaaa gaagaagagg aaggtttcat cggagaccgg ccctgttgct     960
gttgacccca ccctgcggcg gagaatcgag ccacacgagt cgaggtgtt cttcgaccca    1020
agggagctcc gcaaggagac gtgcctcctg tacgagatca ctggggcgg caggcactcc    1080
atctggaggc acaccagcca aaacaccaac aagcacgtgg aggtcaactt catcgagaag    1140
ttcaccaccg agaggtactt ctgcccaaac acccgctgct ccatcacctg gttcctgtcc    1200
tggagcccat gcggcgagtg ctccaggggcc atcaccgagt tcctcagccg ctacccacac    1260
```

```
gtcaccctgt tcatctacat cgccaggctc taccaccacg ccgacccaag gaacaggcag    1320
ggcctccgcg acctgatctc cagcggcgtg accatccaaa tcatgaccga gcaggagtcc    1380
ggctactgct ggaggaactt cgtcaactac tccccaagca acgaggccca ctggccaagg    1440
tacccacacc tctgggtgcg cctctacgtg ctcgagctgt actgcatcat cctcggcctg    1500
ccaccatgcc tcaacatcct gaggcgcaag caaccacagc tgaccttctt caccatcgcc    1560
ctccaaagct gccactacca gaggctccca ccacacatcc tgtgggctac cggcctcaag    1620
tccggcagcg agacgccagg cacctccgag agcgctacgc tgaacttaa gcaaatcacg     1680 cgtgactccg gcggcagcac caacctgtcc gacatcatcg agaaggagac gggcaagcaa    1740
ctcgtgatcc aggagagcat cctcatgctg ccagaggagg tggaggaggt catcggcaac    1800
aagccagagt ccgacatcct ggtgcacacc gcctacgacg agtccaccga cgagaacgtc    1860
atgctcctga ccagcgacgc cccagagtac aagccatggg ccctcgtcat ccaggacagc    1920
aacgggagac acaagatcaa gatgctgtcg ggggggagcc caagaagaa gcggaaggtg     1980 tagggatccc gggcccgtcg actgcagagg cctgcatgca agcttggcgt aatcatggtc    2040
atagctgttt cctgtgtgaa attgttatcc gctcacaatt ccacacaaca tacgagccgg    2100
aagcataaag tgtaaagcct ggggtgccta atgagtgagc taactcacat taattgcgtt    2160
gcgctcactg cccgctttcc agtcgggaaa cctgtcgtgc cagctgcatt aatgaatcgg    2220
ccaacgcgcg gggagaggcg gtttgcgtat tgggcgctct tccgcttcct cgctcactga    2280
ctcgctgcgc tcggtcgttc ggctgcggcg agcggtatca gctcactcaa aggcggtaat    2340
acggttatcc acagaatcag gggataacgc aggaaagaac atgtgagcaa aaggccagca    2400
aaaggccagg aaccgtaaaa aggccgcgtt gctggcgttt ttccataggc tccgcccccc    2460
tgacgagcat cacaaaaatc gacgctcaag tcagaggtgg cgaaacccga caggactata    2520
aagataccag gcgtttcccc ctggaagctc cctcgtgcgc tctcctgttc cgaccctgcc    2580
gcttaccgga tacctgtccg cctttctccc ttcgggaagc gtggcgcttt ctcatagctc    2640
acgctgtagg tatctcagtt cggtgtaggt cgttcgctcc aagctgggct gtgtgcacga    2700
accccccgtt cagcccgacc gctgcgcctt atccggtaac tatcgtcttg agtccaaccc    2760
ggtaagacac gacttatcgc cactggcagc agccactggt aacaggatta gcagagcgag    2820
gtatgtaggc ggtgctacag agttcttgaa gtggtggcct aactacggct acactagaag    2880
aacagtattt ggtatctgcg ctctgctgaa gccagttacc ttcggaaaaa gagttggtag    2940
ctcttgatcc ggcaaacaaa ccaccgctgg tagcggtggt ttttttgttt gcaagcagca    3000
gattacgcgc agaaaaaaag gatctcaaga agatcctttg atcttttcta cggggtctga    3060
cgctcagtgg aacgaaaact cacgttaagg gattttggtc atgagcgcaa cacccgtggaa   3120 acggatgaag gcacgaaccc agttgacata agcctgttcg gttcgtaaac tgtaatgcaa    3180
gtagcgtatg cgctcacgca actggtccag aaccttgacc gaacgcagcg gtggtaacgg    3240
cgcagtggcg gttttcatgg cttgttatga ctgttttttt gtacagtcta tgcctcgggc    3300
atccaagcag caagcgcgtt acgccgtggg tcgatgtttg atgttatgga gcagcaacga    3360
tgttacgcag cagcaacgat gttacgcagc agggcagtcg ccctaaaaca aagttaggtg    3420
gctcaagtat gggcatcatt cgcacatgta ggctcggccc tgaccaagtc aaatccatgc    3480
gggctgctct tgatcttttc ggtcgtgagt tcgg                                3514
```

<210> SEQ ID NO 11

```
<211> LENGTH: 227
<212> TYPE: PRT
<213> ORGANISM: Artificial Sequence
<220> FEATURE:
<223> OTHER INFORMATION: Description of Artificial Sequence: Synthetic
      APOBEC1

<400> SEQUENCE: 11

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
210                 215                 220

Thr Gly Leu
225

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      XTEN

<400> SEQUENCE: 12

Lys Ser Gly Ser Glu Thr Pro Gly Thr Ser Glu Ser Ala Thr Pro Glu
1               5                   10                  15

<210> SEQ ID NO 13
<211> LENGTH: 1384
<212> TYPE: PRT
<213> ORGANISM: Artificial Sequence
<220> FEATURE:
<223> OTHER INFORMATION: Description of Artificial Sequence: Synthetic
      nCas9(D10A)

<400> SEQUENCE: 13
```

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
```

```
                420             425             430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
            565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
            645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
            725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
            805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
            835                 840                 845
```

```
Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245
```

```
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
Gly Leu Tyr Glu Thr Arg Ile Asp Leu Ser Gln Leu Gly Gly Asp
    1355                1360                1365
Lys Arg Pro Ala Ala Thr Lys Lys Ala Gly Gln Ala Lys Lys Lys
    1370                1375                1380
Lys

<210> SEQ ID NO 14
<211> LENGTH: 1384
<212> TYPE: PRT
<213> ORGANISM: Artificial Sequence
<220> FEATURE:
<223> OTHER INFORMATION: Description of Artificial Sequence: Synthetic
      dCas9

<400> SEQUENCE: 14

Met Asp Lys Lys Tyr Ser Ile Gly Leu Ala Ile Gly Thr Asn Ser Val
1               5                   10                  15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
            35                  40                  45
Gly Ala Leu Leu Phe Asp Ser Gly Glu Thr Ala Glu Ala Thr Arg Leu
        50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
```

-continued

```
Lys Ala Ile Leu Ser Ala Arg Leu Ser Lys Ser Arg Leu Glu Asn
    210                 215                 220
Leu Ile Ala Gln Leu Pro Gly Glu Lys Asn Gly Leu Phe Gly Asn
225                 230                 235                 240
Leu Ile Ala Leu Ser Leu Gly Leu Thr Pro Asn Phe Lys Ser Asn Phe
            245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
```

-continued

```
                625                 630                 635                 640
        His Leu Phe Asp Asp Lys Val Met Lys Gln Leu Lys Arg Arg Arg Tyr
                            645                 650                 655
        Thr Gly Trp Gly Arg Leu Ser Arg Lys Leu Ile Asn Gly Ile Arg Asp
                            660                 665                 670
        Lys Gln Ser Gly Lys Thr Ile Leu Asp Phe Leu Lys Ser Asp Gly Phe
                            675                 680                 685
        Ala Asn Arg Asn Phe Met Gln Leu Ile His Asp Ser Leu Thr Phe
                            690                 695                 700
        Lys Glu Asp Ile Gln Lys Ala Gln Val Ser Gly Gln Gly Asp Ser Leu
        705                 710                 715                 720
        His Glu His Ile Ala Asn Leu Ala Gly Ser Pro Ala Ile Lys Lys Gly
                            725                 730                 735
        Ile Leu Gln Thr Val Lys Val Val Asp Glu Leu Val Lys Val Met Gly
                            740                 745                 750
        Arg His Lys Pro Glu Asn Ile Val Ile Glu Met Ala Arg Glu Asn Gln
                            755                 760                 765
        Thr Thr Gln Lys Gly Gln Lys Asn Ser Arg Glu Arg Met Lys Arg Ile
                            770                 775                 780
        Glu Glu Gly Ile Lys Glu Leu Gly Ser Gln Ile Leu Lys Glu His Pro
        785                 790                 795                 800
        Val Glu Asn Thr Gln Leu Gln Asn Glu Lys Leu Tyr Leu Tyr Tyr Leu
                            805                 810                 815
        Gln Asn Gly Arg Asp Met Tyr Val Asp Gln Glu Leu Asp Ile Asn Arg
                            820                 825                 830
        Leu Ser Asp Tyr Asp Val Asp Ala Ile Val Pro Gln Ser Phe Leu Lys
                            835                 840                 845
        Asp Asp Ser Ile Asp Asn Lys Val Leu Thr Arg Ser Asp Lys Asn Arg
                            850                 855                 860
        Gly Lys Ser Asp Asn Val Pro Ser Glu Val Val Lys Lys Met Lys
        865                 870                 875                 880
        Asn Tyr Trp Arg Gln Leu Leu Asn Ala Lys Leu Ile Thr Gln Arg Lys
                            885                 890                 895
        Phe Asp Asn Leu Thr Lys Ala Glu Arg Gly Gly Leu Ser Glu Leu Asp
                            900                 905                 910
        Lys Ala Gly Phe Ile Lys Arg Gln Leu Val Glu Thr Arg Gln Ile Thr
                            915                 920                 925
        Lys His Val Ala Gln Ile Leu Asp Ser Arg Met Asn Thr Lys Tyr Asp
                            930                 935                 940
        Glu Asn Asp Lys Leu Ile Arg Glu Val Lys Val Ile Thr Leu Lys Ser
        945                 950                 955                 960
        Lys Leu Val Ser Asp Phe Arg Lys Asp Phe Gln Phe Tyr Lys Val Arg
                            965                 970                 975
        Glu Ile Asn Asn Tyr His His Ala His Asp Ala Tyr Leu Asn Ala Val
                            980                 985                 990
        Val Gly Thr Ala Leu Ile Lys Lys Tyr Pro Lys Leu Glu Ser Glu Phe
                            995                 1000                1005
        Val Tyr Gly Asp Tyr Lys Val Tyr Asp Val Arg Lys Met Ile Ala
                            1010                1015                1020
        Lys Ser Glu Gln Glu Ile Gly Lys Ala Thr Ala Lys Tyr Phe Phe
                            1025                1030                1035
        Tyr Ser Asn Ile Met Asn Phe Phe Lys Thr Glu Ile Thr Leu Ala
                            1040                1045                1050
```

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Lys Arg Pro Ala Ala Thr Lys Lys Ala Gly Gln Ala Lys Lys Lys
1370                1375                1380

Lys

<210> SEQ ID NO 15
<211> LENGTH: 83
<212> TYPE: PRT
<213> ORGANISM: Artificial Sequence
<220> FEATURE:
<223> OTHER INFORMATION: Description of Artificial Sequence: Synthetic
      UGI

<400> SEQUENCE: 15

Thr Asn Leu Ser Asp Ile Ile Glu Lys Glu Thr Gly Lys Gln Leu Val
1               5                   10                  15

Ile Gln Glu Ser Ile Leu Met Leu Pro Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
50                  55                  60

Lys Pro Trp Ala Leu Val Ile Gln Asp Ser Asn Gly Glu Asn Lys Ile
65                  70                  75                  80

Lys Met Leu

<210> SEQ ID NO 16
<211> LENGTH: 239
<212> TYPE: PRT
<213> ORGANISM: Artificial Sequence
<220> FEATURE:
<223> OTHER INFORMATION: Description of Artificial Sequence: Synthetic
      GFP

<400> SEQUENCE: 16

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235

<210> SEQ ID NO 17
<211> LENGTH: 239
<212> TYPE: PRT
<213> ORGANISM: Artificial Sequence
<220> FEATURE:
<223> OTHER INFORMATION: Description of Artificial Sequence: Synthetic BFP

<400> SEQUENCE: 17

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

<210> SEQ ID NO 18
<211> LENGTH: 4107
<212> TYPE: DNA
<213> ORGANISM: Artificial Sequence
<220> FEATURE:
<223> OTHER INFORMATION: Description of Artificial Sequence: Synthetic WT spCas9 nucleotide sequence

<400> SEQUENCE: 18

| | |
|---|---|
| atggataaga aatactcaat aggcttagat atcggcacaa atagcgtcgg atgggcggtg | 60 |
| atcactgatg aatataaggt tccgtctaaa aagttcaagg ttctgggaaa tacagaccgc | 120 |
| cacagtatca aaaaaaatct tatagggget cttttatttg acagtggaga gacagcggaa | 180 |
| gcgactcgtc tcaaacggac agctcgtaga aggtatacac gtcggaagaa tcgtatttgt | 240 |
| tatctacagg agatttttc aaatgagatg gcgaaagtag atgatagttt ctttcatcga | 300 |
| cttgaagagt cttttttggt ggaagaagac aagaagcatg aacgtcatcc tatttttgga | 360 |
| aatatagtag atgaagttgc ttatcatgag aaatatccaa ctatctatca tctgcgaaaa | 420 |
| aaattggtag attctactga taaagcggat ttgcgcttaa tctatttggc cttagcgcat | 480 |
| atgattaagt ttcgtggtca tttttgatt gagggagatt taaatcctga taatagtgat | 540 |

```
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga agagacaaga agactttttat ccattttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaagaagaa ttatttcaaa aaaatagaat gttttgatag tgttgaaatt   1740
tcaggagttg aagatagatt taatgcttca ttaggtacct accatgattt gctaaaaatt   1800
attaaagata aagattttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040 gatttttttga aatcagatgg ttttgccaat cgcaatttta tgcagctgat ccatgatgat   2100
agtttgacat ttaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
```

| | |
|---|---|
| aaattagttt ctgacttccg aaaagatttc caattctata agtacgtga gattaacaat | 2940 |
| taccatcatg cccatgatgc gtatctaaat gccgtcgttg gaactgcttt gattaagaaa | 3000 |
| tatccaaaac ttgaatcgga gtttgtctat ggtgattata agtttatga tgttcgtaaa | 3060 |
| atgattgcta agtctgagca agaaataggc aaagcaaccg caaaatattt cttttactct | 3120 |
| aatatcatga acttcttcaa aacagaaatt acacttgcaa atggagagat tcgcaaacgc | 3180 |
| cctctaatcg aaactaatgg ggaaactgga gaaattgtct gggataaagg gcgagatttt | 3240 |
| gccacagtgc gcaaagtatt gtccatgccc caagtcaata ttgtcaagaa aacagaagta | 3300 |
| cagacaggcg gattctccaa ggagtcaatt ttaccaaaaa gaaattcgga caagcttatt | 3360 |
| gctcgtaaaa aagactggga tccaaaaaaa tatggtggtt ttgatagtcc aacggtagct | 3420 |
| tattcagtcc tagtggttgc taaggtggaa aaagggaaat cgaagaagtt aaaatccgtt | 3480 |
| aaagagttac tagggatcac aattatggaa agaagttcct ttgaaaaaaa tccgattgac | 3540 |
| tttttagaag ctaaaggata taaggaagtt aaaaaagact taatcattaa actacctaaa | 3600 |
| tatagtcttt ttgagttaga aaacggtcgt aaacggatgc tggctagtgc cggagaatta | 3660 |
| caaaaaggaa atgagctggc tctgccaagc aaatatgtga atttttata tttagctagt | 3720 |
| cattatgaaa agttgaaggg tagtccagaa gataacgaac aaaaacaatt gtttgttgag | 3780 |
| cagcataagc attatttaga tgagattatt gagcaaatca gtgaattttc taagcgtgtt | 3840 |
| attttagcag atgccaattt agataaagtt cttagtgcat ataacaaaca tagagacaaa | 3900 |
| ccaatacgtg aacaagcaga aaatattatt catttattta cgttgacgaa tcttggagct | 3960 |
| cccgctgctt ttaaatattt tgatacaaca attgatcgta acgatatac gtctacaaaa | 4020 |
| gaagttttag atgccactct tatccatcaa tccatcactg gtctttatga aacacgcatt | 4080 |
| gatttgagtc agctaggagg tgactga | 4107 |

<210> SEQ ID NO 19
<211> LENGTH: 5214
<212> TYPE: DNA
<213> ORGANISM: Artificial Sequence
<220> FEATURE:
<223> OTHER INFORMATION: Description of Artificial Sequence: Synthetic
      Fusion NLS-APOBEC1-XTEN-nCas9-UGI-NLS nucleotide sequence

<400> SEQUENCE: 19

| | |
|---|---|
| atgccaaaga agaagaggaa ggtttcatcg gagaccggcc tgttgctgt tgaccccacc | 60 |
| ctgcggcgga gaatcgagcc acacgagttc gaggtgttct tcgacccaag ggagctccgc | 120 |
| aaggagacgt gcctcctgta cgagatcaac tggggcggca gcactccat ctggaggcac | 180 |
| accagccaaa acaccaacaa gcacgtggag gtcaacttca tcgagaagtt caccaccgag | 240 |
| aggtacttct gccaaacac ccgctgctcc atcacctggt tcctgtcctg agcccatgc | 300 |
| ggcgagtgct ccagggccat accgagttc ctcagccgct acccacacgt caccctgttc | 360 |
| atctacatcg ccaggctcta ccaccacgcc gacccaagga acaggcaggg cctccgcgac | 420 |
| ctgatctcca gcggcgtgac catccaaatc atgaccgagc aggagtccgg ctactgctgg | 480 |
| aggaacttcg tcaactactc cccaagcaac gaggcccact ggccaaggta cccacacctc | 540 |
| tgggtgcgcc tctacgtgct cgagctgtac tgcatcatcc tcggcctgcc accatgcctc | 600 |
| aacatcctga ggcgcaagca accacagctg accttcttca ccatcgccct ccaaagctgc | 660 |
| cactaccaga ggctcccacc acacatcctg tgggctaccg gctcaagtc cggcagcgag | 720 |
| acgccaggca cctccgagag cgctacgcct gaacttaagg acaagaagta ctcgatcggc | 780 |

```
ctcgccatcg ggacgaactc agttggctgg gccgtgatca ccgacgagta caaggtgccc      840
tctaagaagt tcaaggtcct ggggaacacc gaccgccatt ccatcaagaa gaacctcatc      900
ggcgctctcc tgttcgacag cggggagacc gctgaggcta cgaggctcaa gagaaccgct      960
aggcgccggt acacgagaag gaagaacagg atctgctacc tccaagagat tttctccaac     1020
gagatggcca aggttgacga ttcattcttc caccgcctgg aggagtcttt cctcgtggag     1080
gaggataaga agcacgagcg gcatcccatc ttcggcaaca tcgtggacga ggttgcctac     1140
cacgagaagt accctacgat ctaccatctg cggaagaagc tcgtggactc caccgataag     1200
gcggacctca gactgatcta cctcgctctg gcccacatga tcaagttccg cggccatttc     1260
ctgatcgagg gggatctcaa cccagacaac agcgatgttg acaagctgtt catccaactc     1320
gtgcagacct acaaccaact cttcgaggag aacccgatca cgcctctgg cgtggacgcg     1380
aaggctatcc tgtccgcgag gctctcgaag tccaggaggc tggagaacct gatcgctcag     1440
ctcccaggcg agaagaagaa cggcctgttc gggaacctca tcgctctcag cctggggctc     1500
accccgaact tcaagtcgaa cttcgatctc gctgaggacg ccaagctgca actctccaag     1560
gacacctacg acgatgacct cgataacctc ctggcccaga tcggcgatca atacgcggac     1620
ctgttcctcg ctgccaagaa cctgtcggac gccatcctcc tgtcagatat cctccgcgtg     1680
aacaccgaga tcacgaaggc tccactctct gcctccatga tcaagcgcta cgacgagcac     1740
catcaggatc tgaccctcct gaaggcgctg gtccgccaac agctccccga agtacaag     1800
gagattttct cgatcagtc gaagaacggc tacgctgggt acatcgacgg cggggcctca     1860
caagaggagt tctacaagtt catcaagcca atcctggaga gatggacgg cacgaggag     1920
ctcctggtga agctcaacag ggaggacctc ctgcggaagc agagaacctt cgataacggc     1980
agcatcccc accaaatcca tctcggggag ctgcacgcca tcctgagaag gcaagaggac     2040
ttctacccct tcctcaagga taaccgggag aagatcgaga agatcctgac cttcagaatc     2100
ccatactacg tcgccctct cgcgcggggg aactcaagat tcgcttggat gacccgcaag     2160
tctgaggaga ccatcacgcc gtggaacttc gaggaggtgg tggacaaggg cgctagcgct     2220
cagtcgttca tcgagaggat gaccaacttc gacaagaacc tgcccaacga aaggtgctc     2280
cctaagcact cgctcctgta cgagtacttc accgtctaca cgagctcac gaaggtgaag     2340
tacgtcaccg agggcatgcg caagccagcg ttcctgtccg gggagcagaa gaaggctatc     2400
gtggacctcc tgttcaagac caaccggaag gtcacggtta agcaactcaa ggaggactac     2460
ttcaagaaga tcgagtgctt cgattcggtc gagatcagcg gcgttgagga ccgcttcaac     2520
gccagcctcg ggacctacca cgatctcctg aagatcatca aggataagga cttcctggac     2580
aacgaggaga acgaggatat cctggaggac atcgtgctga ccctcacgct gttcgaggac     2640
agggagatga tcgaggagcg cctgaagacg tacgcccatc tcttcgatga caaggtcatg     2700
aagcaactca agcgccggag atacaccggc tgggggaggc tgtcccgcaa gctcatcaac     2760
ggcatccggg acaagcagtc cggaagacc atcctcgact tcctcaagag cgatggcttc     2820
gccaacagga acttcatgca actgatccac gatgacagcc tcaccttcaa ggaggatatc     2880
caaaaggctc aagtgagcgg ccaggggac tcgctgcacg agcatatcgc gaacctcgct     2940
ggctcccccg cgatcaagaa gggcatcctc cagaccgtga aggttgtgga cgagctcgtg     3000
aaggtcatgg ccggcacaa gcctgagaac atcgtcatcg agatggccag agagaaccaa     3060
accacgcaga aggggcaaaa gaactctagg gagcgcatga gcgcatcga ggagggcatc     3120
aaggagctgg ggtcccaaat cctcaaggag cacccagtgg agaacaccca actgcagaac     3180
```

```
gagaagctct acctgtacta cctccagaac ggcagggata tgtacgtgga ccaagagctg    3240
gatatcaacc gcctcagcga ttacgacgtc gatcatatcg ttccccagtc tttcctgaag    3300
gatgactcca tcgacaacaa ggtcctcacc aggtcggaca agaaccgcgg caagtcagat    3360
aacgttccat ctgaggaggt cgttaagaag atgaagaact actggaggca gctcctgaac    3420
gccaagctga tcacgcaaag gaagttcgac aacctcacca aggctgagag aggcgggctc    3480
tcagagctgg acaaggccgg cttcatcaag cggcagctgg tcgagaccag acaaatcacg    3540
aagcacgttg cgcaaatcct cgactctcgg atgaacacga agtacgatga aacgacaag     3600
ctgatcaggg aggttaaggt gatcaccctg aagtctaagc tcgtctccga cttcaggaag    3660
gatttccagt tctacaaggt tcgcgagatc aacaactacc accatgccca tgacgcttac    3720
ctcaacgctg tggtcggcac cgctctgatc aagaagtacc caaagctgga gtccgagttc    3780
gtgtacgggg actacaaggt ttacgatgtg cgcaagatga tcgccaagtc ggagcaagag    3840
atcggcaagg ctaccgccaa gtacttcttc tactcaaaca tcatgaactt cttcaagacc    3900
gagatcacgc tggccaacgg cgagatccgg aagagaccgc tcatcgagac caacggcgag    3960
acgggggaga tcgtgtggga caagggcagg gatttcgcga ccgtccgcaa ggttctctcc    4020
atgccccagg tgaacatcgt caagaagacc gaggtccaaa cgggcgggtt ctcaaaggag    4080
tctatcctgc ctaagcggaa cagcgacaag ctcatcgcca gaagaaagga ctgggaccca    4140
aagaagtacg gcgggttcga cagccctacc gtggcctact cggtcctggt tgtggcgaag    4200
gttgagaagg gcaagtccaa gaagctcaag agcgtgaagg agctcctggg gatcaccatc    4260
atggagaggt ccagcttcga gaagaaccca atcgacttcc tggaggccaa gggctacaag    4320
gaggtgaaga aggacctgat catcaagctc ccgaagtact ctctcttcga gctggagaac    4380
ggcaggaaga gaatgctggc ttccgctggc gagctccaga aggggaacga gctcgcgctg    4440
ccaagcaagt acgtgaactt cctctacctg gcttcccact cgagaagct caagggcagc    4500
ccggaggaca acgagcaaaa gcagctgttc gtcgagcagc acaagcatta cctcgacgag    4560
atcatcgagc aaatctccga gttcagcaag cgcgtgatcc tcgccgacgc gaacctggat    4620
aaggtcctct ccgcctacaa caagcaccgg gacaagccca tcagagagca gcggagaac    4680
atcatccatc tcttcacccct gacgaacctc ggcgctcctg ctgctttcaa gtacttcgac    4740
accacgatcg atcggaagag atacacctcc acgaaggagg tcctggacgc gaccctcatc    4800
caccagtcga tcaccggcct gtacgagacg aggatcgacc tctcacaact cggcggggat    4860
aagagacccg cagcaaccaa gaaggcaggg caagcaaaga agaagaagac gcgtgactcc    4920
ggcggcagca ccaacctgtc cgacatcatc gagaaggaga cgggcaagca actcgtgatc    4980
caggagagca tcctcatgct gccagaggag gtggaggagg tcatcggcaa caagccgagt    5040
tccgacatcc tggtgcacac cgcctacgac gagtccaccg acgagaacgt catgctcctg    5100
accagcgacg cccagagta caagccatgg gccctcgtca tccaggacag caacggggag    5160
aacaagatca agatgctgtc ggggggggagc ccaaagaaga agcggaaggt gtag        5214
```

<210> SEQ ID NO 20
<211> LENGTH: 5214
<212> TYPE: DNA
<213> ORGANISM: Artificial Sequence
<220> FEATURE:
<223> OTHER INFORMATION: Description of Artificial Sequence: Synthetic
      fusion NLS-APOBEC1-XTEN-dCas9-UGI-NLS nucleotide sequence

<400> SEQUENCE: 20

```
atgccaaaga agaagaggaa ggtttcatcg agaccggcc ctgttgctgt tgaccccacc        60
ctgcggcgga gaatcgagcc acacgagttc gaggtgttct tcgacccaag ggagctccgc       120
aaggagacgt gcctcctgta cgagatcaac tggggcggca ggcactccat ctggaggcac       180
accagccaaa acaccaacaa gcacgtggag gtcaacttca tcgagaagtt caccaccgag       240
aggtacttct gcccaaacac ccgctgctcc atcacctggt tcctgtcctg agcccatgc        300 ggcgagtgct ccagggccat caccgagttc ctcagccgct acccacacgt caccctgttc       360
atctacatcg ccaggctcta ccaccacgcc gacccaagga caggcagggg cctccgcgac       420
ctgatctcca gcggcgtgac catccaaatc atgaccgagc aggagtccgg ctactgctgg       480
aggaacttcg tcaactactc cccaagcaac gaggcccact ggccaaggta cccacacctc       540
tgggtgcgcc tctacgtgct cgagctgtac tgcatcatcc tcggcctgcc accatgcctc       600
aacatcctga ggcgcaagca accacagctg accttcttca ccatcgccct ccaaagctgc       660
cactaccaga ggctcccacc acacatcctg tgggctaccg gcctcaagtc cggcagcgag       720
acgccaggca cctccgagag cgctacgcct gaacttaagg acaagaagta ctcgatcggc       780
ctcgccatcg ggacgaactc agttggctgg ccgtgatcca ccgacgagta caaggtgccc       840
tctaagaagt tcaaggtcct ggggaacacc gaccgccatt ccatcaagaa gaacctcatc       900
ggcgctctcc tgttcgacag cggggagacc gctgaggcta cgaggctcaa gagaaccgct       960
aggcgccggt acacgagaag gaagaacagg atctgctacc tccaagagat tttctccaac      1020
gagatggcca aggttgacga ttcattcttc caccgcctgg aggagtcttt cctcgtggag      1080
gaggataaga agcacgagcg gcatcccatc ttcggcaaca tcgtggacga ggttgcctac      1140
cacgagaagt accctacgat ctaccatctg cggaagaagc tcgtggactc caccgataag      1200
gcggacctca gactgatcta cctcgctctg gcccacatga tcaagttccg cggccatttc      1260
ctgatcgagg gggatctcaa cccagacaac agcgatgttg acaagctgtt catccaactc      1320
gtgcagacct acaaccaact cttcgaggag aacccgatca acgcctctgg cgtggacgcg      1380
aaggctatcc tgtccgcgag gctctcgaag tccaggaggc tggagaacct gatcgctcag      1440
ctcccaggcg agaagaagaa cggcctgttc gggaacctca tcgctctcag cctgggctc       1500 accccgaact tcaagtcgaa cttcgatctc gctgaggacg ccaagctgca actctccaag      1560
gacacctacg acgatgacct cgataacctc ctggcccaga tcggcgatca atacgcggac      1620
ctgttcctcg ctgccaagaa cctgtcggac gccatcctcc tgtcagatat cctccgcgtg      1680
aacaccgaga tcacgaaggc tccactctct gcctccatga tcaagcgcta cgacgagcac      1740
catcaggatc tgacctcct gaaggcgctg gtccgccaac agctcccgga agtacaag         1800 gagatttct cgatcagtc gaagaacggc tacgctggt acatcgacgg cggggcctca         1860
caagaggagt tctacaagtt catcaagcca atcctggaga gatggacgg cacggaggag        1920 ctcctggtga agctcaacag ggaggacctc ctgcggaagc agagaacctt cgataacggc      1980
agcatccccc accaaatcca tctcggggag ctgcacgcca tcctgagaag gcaagaggac      2040 ttctacccctt tcctcaagga taaccgggag aagatcgaga agatcctgac cttcagaatc      2100
ccatactacg tcggccctct cgcgcggggg aactcaagat tcgcttggat gacccgcaag      2160
tctgaggaga ccatcacgcc gtggaacttc gaggaggtgg tggacaaggg cgctagcgct      2220
cagtcgttca tcgagaggat gaccaacttc gacaagaacc tgcccaacga gaaggtgctc      2280
cctaagcact cgctcctgta cgagtacttc accgtctaca acgagctcac gaaggtgaag      2340
```

```
tacgtcaccg agggcatgcg caagccagcg ttcctgtccg gggagcagaa gaaggctatc    2400
gtggacctcc tgttcaagac caaccggaag gtcacggtta agcaactcaa ggaggactac    2460
ttcaagaaga tcgagtgctt cgattcggtc gagatcagcg gcgttgagga ccgcttcaac    2520
gccagcctcg ggacctacca cgatctcctg aagatcatca aggataagga cttcctggac    2580
aacgaggaga acgaggatat cctggaggac atcgtgctga ccctcacgct gttcgaggac    2640
agggagatga tcgaggagcg cctgaagacg tacgcccatc tcttcgatga caaggtcatg    2700
aagcaactca gcgccggag atacaccggc tgggggaggc tgtcccgcaa gctcatcaac    2760
ggcatccggg acaagcagtc cgggaagacc atcctcgact tcctcaagag cgatggcttc    2820
gccaacagga acttcatgca actgatccac gatgacagcc tcaccttcaa ggaggatatc    2880
caaaaggctc aagtgagcgg ccaggggac tcgctgcacg agcatatcgc gaacctcgct    2940
ggctcccccg cgatcaagaa gggcatcctc cagaccgtga aggttgtgga cgagctcgtg    3000
aaggtcatgg gccggcacaa gcctgagaac atcgtcatcg agatggccag agagaaccaa    3060
accacgcaga agggcaaaaa gaactctagg gagcgcatga agcgcatcga ggagggcatc    3120
aaggagctgg ggtcccaaat cctcaaggag cacccagtgg agaacaccca actgcagaac    3180
gagaagctct acctgtacta cctccagaac ggcagggata tgtacgtgga ccaagagctg    3240
gatatcaacc gcctcagcga ttacgacgtc gatgctatcg ttccccagtc tttcctgaag    3300
gatgactcca tcgacaacaa ggtcctcacc aggtcggaca gaaccgcgg caagtcagat    3360 aacgttccat ctgaggaggt cgttaagaag atgaagaact actggaggca gctcctgaac    3420
gccaagctga tcacgcaaag gaagttcgac aacctcacca aggctgagag aggcgggctc    3480
tcagagctgg acaaggccgg cttcatcaag cggcagctgg tcgagaccag acaaatcacg    3540
aagcacgttg cgcaaatcct cgactctcgg atgaacacga agtacgatga gaacgacaag    3600
ctgatcaggg aggttaaggt gatcaccctg aagtctaagc tcgtctccga cttcaggaag    3660
gatttccagt tctacaaggt tcgcgagatc aacaactacc accatgccca tgacgcttac    3720
ctcaacgctg tggtcggcac cgctctgatc aagaagtacc caaagctgga gtccgagttc    3780
gtgtacgggg actacaaggt ttacgatgtg cgcaagatga tcgccaagtc ggagcaagag    3840
atcggcaagg ctaccgccaa gtacttcttc tactcaaaca tcatgaactt cttcaagacc    3900
gagatcacgc tggccaacgg cgagatccgg aagagaccgc tcatcgagac caacggcgag    3960 acggggaga tcgtgtggga caagggcagg gatttcgcga ccgtccgcaa ggttctctcc    4020
atgccccagg tgaacatcgt caagaagacc gaggtccaaa cgggcgggtt ctcaaaggag    4080
tctatcctgc ctaagcggaa cagcgacaag ctcatcgcca gaaagaagga ctgggaccca    4140
aagaagtacg gcgggttcga cagccctacc gtggcctact cggtcctggt tgtggcgaag    4200
gttgagaagg gcaagtccaa gaagctcaag agcgtgaagg agctcctggg gatcaccatc    4260
atggagaggt ccagcttcga gaagaaccca atcgacttcc tggaggccaa gggctacaag    4320
gaggtgaaga aggacctgat catcaagctc ccgaagtact ctctcttcga gctggagaac    4380
ggcaggaaga gaatgctggc ttccgctggc gagctccaga gggaacga gctcgcgctg    4440 ccaagcaagt acgtgaactt cctctacctg gcttcccact acgagaagct caagggcagc    4500
ccggaggaca acgagcaaaa gcagctgttc gtcgagcagc acaagcatta cctcgacgag    4560
atcatcgagc aaatctccga gttcagcaag cgcgtgatcc tcgccgacgc gaacctggat    4620
aaggtcctct ccgcctacaa caagcaccgg gacaagccca tcagagagca gcggagaac    4680 atcatccatc tcttcacccct gacgaacctc ggcgctcctg ctgctttcaa gtacttcgac    4740
```

```
accacgatcg atcggaagag atacacctcc acgaaggagg tcctggacgc gaccctcatc    4800
caccagtcga tcaccggcct gtacgagacg aggatcgacc tctcacaact cggcggggat    4860
aagagacccg cagcaaccaa gaaggcaggg caagcaaaga agaagaagac gcgtgactcc    4920
ggcggcagca ccaacctgtc cgacatcatc gagaaggaga cgggcaagca actcgtgatc    4980
caggagagca tcctcatgct gccagaggag gtggaggagg tcatcggcaa caagccagag    5040
tccgacatcc tggtgcacac cgcctacgac gagtccaccg acgagaacgt catgctcctg    5100
accagcgacg ccccagagta caagccatgg gccctcgtca tccaggacag caacggggag    5160
aacaagatca agatgctgtc ggggggagc ccaaagaaga agcggaaggt gtag           5214
```

<210> SEQ ID NO 21
<211> LENGTH: 1368
<212> TYPE: PRT
<213> ORGANISM: Artificial Sequence
<220> FEATURE:
<223> OTHER INFORMATION: Description of Artificial Sequence: Synthetic
   WT spCas9

<400> SEQUENCE: 21

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

-continued

```
Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
```

-continued

```
            690             695             700
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110
```

```
Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 22
<211> LENGTH: 1737
<212> TYPE: PRT
<213> ORGANISM: Artificial Sequence
<220> FEATURE:
<223> OTHER INFORMATION: Description of Artificial Sequence: Synthetic
      Fusion NLS-APOBEC1-XTEN-nCas9-UGI-NLS

<400> SEQUENCE: 22

Met Pro Lys Lys Lys Arg Lys Val Ser Ser Glu Thr Gly Pro Val Ala
1               5                   10                  15

Val Asp Pro Thr Leu Arg Arg Arg Ile Glu Pro His Glu Phe Glu Val
                20                  25                  30

Phe Phe Asp Pro Arg Glu Leu Arg Lys Glu Thr Cys Leu Leu Tyr Glu
            35                  40                  45

Ile Asn Trp Gly Gly Arg His Ser Ile Trp Arg His Thr Ser Gln Asn
        50                  55                  60

Thr Asn Lys His Val Glu Val Asn Phe Ile Glu Lys Phe Thr Thr Glu
65                  70                  75                  80

Arg Tyr Phe Cys Pro Asn Thr Arg Cys Ser Ile Thr Trp Phe Leu Ser
```

```
            85                  90                  95
Trp Ser Pro Cys Gly Glu Cys Ser Arg Ala Ile Thr Glu Phe Leu Ser
            100                 105                 110
Arg Tyr Pro His Val Thr Leu Phe Ile Tyr Ile Ala Arg Leu Tyr His
            115                 120                 125
His Ala Asp Pro Arg Asn Arg Gln Gly Leu Arg Asp Leu Ile Ser Ser
130                 135                 140
Gly Val Thr Ile Gln Ile Met Thr Glu Gln Glu Ser Gly Tyr Cys Trp
145                 150                 155                 160
Arg Asn Phe Val Asn Tyr Ser Pro Ser Asn Glu Ala His Trp Pro Arg
                165                 170                 175
Tyr Pro His Leu Trp Val Arg Leu Tyr Val Leu Glu Leu Tyr Cys Ile
                180                 185                 190
Ile Leu Gly Leu Pro Pro Cys Leu Asn Ile Leu Arg Arg Lys Gln Pro
                195                 200                 205
Gln Leu Thr Phe Phe Thr Ile Ala Leu Gln Ser Cys His Tyr Gln Arg
    210                 215                 220
Leu Pro Pro His Ile Leu Trp Ala Thr Gly Leu Lys Ser Gly Ser Glu
225                 230                 235                 240
Thr Pro Gly Thr Ser Glu Ser Ala Thr Pro Glu Leu Lys Asp Lys Lys
                245                 250                 255
Tyr Ser Ile Gly Leu Ala Ile Gly Thr Asn Ser Val Gly Trp Ala Val
                260                 265                 270
Ile Thr Asp Glu Tyr Lys Val Pro Ser Lys Lys Phe Lys Val Leu Gly
                275                 280                 285
Asn Thr Asp Arg His Ser Ile Lys Lys Asn Leu Ile Gly Ala Leu Leu
290                 295                 300
Phe Asp Ser Gly Glu Thr Ala Glu Ala Thr Arg Leu Lys Arg Thr Ala
305                 310                 315                 320
Arg Arg Arg Tyr Thr Arg Arg Lys Asn Arg Ile Cys Tyr Leu Gln Glu
                325                 330                 335
Ile Phe Ser Asn Glu Met Ala Lys Val Asp Asp Ser Phe Phe His Arg
                340                 345                 350
Leu Glu Glu Ser Phe Leu Val Glu Glu Asp Lys Lys His Glu Arg His
                355                 360                 365
Pro Ile Phe Gly Asn Ile Val Asp Glu Val Ala Tyr His Glu Lys Tyr
                370                 375                 380
Pro Thr Ile Tyr His Leu Arg Lys Lys Leu Val Asp Ser Thr Asp Lys
385                 390                 395                 400
Ala Asp Leu Arg Leu Ile Tyr Leu Ala Leu Ala His Met Ile Lys Phe
                405                 410                 415
Arg Gly His Phe Leu Ile Glu Gly Asp Leu Asn Pro Asp Asn Ser Asp
                420                 425                 430
Val Asp Lys Leu Phe Ile Gln Leu Val Gln Thr Tyr Asn Gln Leu Phe
                435                 440                 445
Glu Glu Asn Pro Ile Asn Ala Ser Gly Val Asp Ala Lys Ala Ile Leu
                450                 455                 460
Ser Ala Arg Leu Ser Lys Ser Arg Arg Leu Glu Asn Leu Ile Ala Gln
465                 470                 475                 480
Leu Pro Gly Glu Lys Lys Asn Gly Leu Phe Gly Asn Leu Ile Ala Leu
                485                 490                 495
Ser Leu Gly Leu Thr Pro Asn Phe Lys Ser Asn Phe Asp Leu Ala Glu
                500                 505                 510
```

```
Asp Ala Lys Leu Gln Leu Ser Lys Asp Thr Tyr Asp Asp Leu Asp
            515                 520                 525

Asn Leu Leu Ala Gln Ile Gly Asp Gln Tyr Ala Asp Leu Phe Leu Ala
    530                 535                 540

Ala Lys Asn Leu Ser Asp Ala Ile Leu Leu Ser Asp Ile Leu Arg Val
545                 550                 555                 560

Asn Thr Glu Ile Thr Lys Ala Pro Leu Ser Ala Ser Met Ile Lys Arg
                565                 570                 575

Tyr Asp Glu His His Gln Asp Leu Thr Leu Leu Lys Ala Leu Val Arg
            580                 585                 590

Gln Gln Leu Pro Glu Lys Tyr Lys Glu Ile Phe Phe Asp Gln Ser Lys
            595                 600                 605

Asn Gly Tyr Ala Gly Tyr Ile Asp Gly Gly Ala Ser Gln Glu Glu Phe
            610                 615                 620

Tyr Lys Phe Ile Lys Pro Ile Leu Glu Lys Met Asp Gly Thr Glu Glu
625                 630                 635                 640

Leu Leu Val Lys Leu Asn Arg Glu Asp Leu Leu Arg Lys Gln Arg Thr
                645                 650                 655

Phe Asp Asn Gly Ser Ile Pro His Gln Ile His Leu Gly Glu Leu His
            660                 665                 670

Ala Ile Leu Arg Arg Gln Glu Asp Phe Tyr Pro Phe Leu Lys Asp Asn
            675                 680                 685

Arg Glu Lys Ile Glu Lys Ile Leu Thr Phe Arg Ile Pro Tyr Tyr Val
            690                 695                 700

Gly Pro Leu Ala Arg Gly Asn Ser Arg Phe Ala Trp Met Thr Arg Lys
705                 710                 715                 720

Ser Glu Glu Thr Ile Thr Pro Trp Asn Phe Glu Glu Val Val Asp Lys
                725                 730                 735

Gly Ala Ser Ala Gln Ser Phe Ile Glu Arg Met Thr Asn Phe Asp Lys
            740                 745                 750

Asn Leu Pro Asn Glu Lys Val Leu Pro Lys His Ser Leu Leu Tyr Glu
            755                 760                 765

Tyr Phe Thr Val Tyr Asn Glu Leu Thr Lys Val Lys Tyr Val Thr Glu
            770                 775                 780

Gly Met Arg Lys Pro Ala Phe Leu Ser Gly Glu Gln Lys Lys Ala Ile
785                 790                 795                 800

Val Asp Leu Leu Phe Lys Thr Asn Arg Lys Val Thr Val Lys Gln Leu
                805                 810                 815

Lys Glu Asp Tyr Phe Lys Lys Ile Glu Cys Phe Asp Ser Val Glu Ile
            820                 825                 830

Ser Gly Val Glu Asp Arg Phe Asn Ala Ser Leu Gly Thr Tyr His Asp
            835                 840                 845

Leu Leu Lys Ile Ile Lys Asp Lys Asp Phe Leu Asp Asn Glu Glu Asn
850                 855                 860

Glu Asp Ile Leu Glu Asp Ile Val Leu Thr Leu Thr Leu Phe Glu Asp
865                 870                 875                 880

Arg Glu Met Ile Glu Glu Arg Leu Lys Thr Tyr Ala His Leu Phe Asp
                885                 890                 895

Asp Lys Val Met Lys Gln Leu Lys Arg Arg Arg Tyr Thr Gly Trp Gly
            900                 905                 910

Arg Leu Ser Arg Lys Leu Ile Asn Gly Ile Arg Asp Lys Gln Ser Gly
            915                 920                 925
```

```
Lys Thr Ile Leu Asp Phe Leu Lys Ser Asp Gly Phe Ala Asn Arg Asn
            930             935             940

Phe Met Gln Leu Ile His Asp Asp Ser Leu Thr Phe Lys Glu Asp Ile
945             950             955             960

Gln Lys Ala Gln Val Ser Gly Gln Gly Asp Ser Leu His Glu His Ile
                965             970             975

Ala Asn Leu Ala Gly Ser Pro Ala Ile Lys Lys Gly Ile Leu Gln Thr
                980             985             990

Val Lys Val Val Asp Glu Leu Val Lys Val Met Gly Arg His Lys Pro
        995             1000            1005

Glu Asn Ile Val Ile Glu Met Ala Arg Glu Asn Gln Thr Thr Gln
    1010            1015            1020

Lys Gly Gln Lys Asn Ser Arg Glu Arg Met Lys Arg Ile Glu Glu
    1025            1030            1035

Gly Ile Lys Glu Leu Gly Ser Gln Ile Leu Lys Glu His Pro Val
    1040            1045            1050

Glu Asn Thr Gln Leu Gln Asn Glu Lys Leu Tyr Leu Tyr Tyr Leu
    1055            1060            1065

Gln Asn Gly Arg Asp Met Tyr Val Asp Gln Glu Leu Asp Ile Asn
    1070            1075            1080

Arg Leu Ser Asp Tyr Asp Val Asp His Ile Val Pro Gln Ser Phe
    1085            1090            1095

Leu Lys Asp Asp Ser Ile Asp Asn Lys Val Leu Thr Arg Ser Asp
    1100            1105            1110

Lys Asn Arg Gly Lys Ser Asp Asn Val Pro Ser Glu Glu Val Val
    1115            1120            1125

Lys Lys Met Lys Asn Tyr Trp Arg Gln Leu Leu Asn Ala Lys Leu
    1130            1135            1140

Ile Thr Gln Arg Lys Phe Asp Asn Leu Thr Lys Ala Glu Arg Gly
    1145            1150            1155

Gly Leu Ser Glu Leu Asp Lys Ala Gly Phe Ile Lys Arg Gln Leu
    1160            1165            1170

Val Glu Thr Arg Gln Ile Thr Lys His Val Ala Gln Ile Leu Asp
    1175            1180            1185

Ser Arg Met Asn Thr Lys Tyr Asp Glu Asn Asp Lys Leu Ile Arg
    1190            1195            1200

Glu Val Lys Val Ile Thr Leu Lys Ser Lys Leu Val Ser Asp Phe
    1205            1210            1215

Arg Lys Asp Phe Gln Phe Tyr Lys Val Arg Glu Ile Asn Asn Tyr
    1220            1225            1230

His His Ala His Asp Ala Tyr Leu Asn Ala Val Val Gly Thr Ala
    1235            1240            1245

Leu Ile Lys Lys Tyr Pro Lys Leu Glu Ser Glu Phe Val Tyr Gly
    1250            1255            1260

Asp Tyr Lys Val Tyr Asp Val Arg Lys Met Ile Ala Lys Ser Glu
    1265            1270            1275

Gln Glu Ile Gly Lys Ala Thr Ala Lys Tyr Phe Phe Tyr Ser Asn
    1280            1285            1290

Ile Met Asn Phe Phe Lys Thr Glu Ile Thr Leu Ala Asn Gly Glu
    1295            1300            1305

Ile Arg Lys Arg Pro Leu Ile Glu Thr Asn Gly Glu Thr Gly Glu
    1310            1315            1320

Ile Val Trp Asp Lys Gly Arg Asp Phe Ala Thr Val Arg Lys Val
```

-continued

```
                1325                1330                1335

Leu Ser Met Pro Gln Val Asn Ile Val Lys Lys Thr Glu Val Gln
        1340                1345                1350

Thr Gly Gly Phe Ser Lys Glu Ser Ile Leu Pro Lys Arg Asn Ser
    1355                1360                1365

Asp Lys Leu Ile Ala Arg Lys Lys Asp Trp Asp Pro Lys Lys Tyr
        1370                1375                1380

Gly Gly Phe Asp Ser Pro Thr Val Ala Tyr Ser Val Leu Val Val
        1385                1390                1395

Ala Lys Val Glu Lys Gly Lys Ser Lys Lys Leu Lys Ser Val Lys
        1400                1405                1410

Glu Leu Leu Gly Ile Thr Ile Met Glu Arg Ser Ser Phe Glu Lys
        1415                1420                1425

Asn Pro Ile Asp Phe Leu Glu Ala Lys Gly Tyr Lys Glu Val Lys
        1430                1435                1440

Lys Asp Leu Ile Ile Lys Leu Pro Lys Tyr Ser Leu Phe Glu Leu
        1445                1450                1455

Glu Asn Gly Arg Lys Arg Met Leu Ala Ser Ala Gly Glu Leu Gln
        1460                1465                1470

Lys Gly Asn Glu Leu Ala Leu Pro Ser Lys Tyr Val Asn Phe Leu
        1475                1480                1485

Tyr Leu Ala Ser His Tyr Glu Lys Leu Lys Gly Ser Pro Glu Asp
        1490                1495                1500

Asn Glu Gln Lys Gln Leu Phe Val Glu Gln His Lys His Tyr Leu
        1505                1510                1515

Asp Glu Ile Ile Glu Gln Ile Ser Glu Phe Ser Lys Arg Val Ile
        1520                1525                1530

Leu Ala Asp Ala Asn Leu Asp Lys Val Leu Ser Ala Tyr Asn Lys
        1535                1540                1545

His Arg Asp Lys Pro Ile Arg Glu Gln Ala Glu Asn Ile Ile His
        1550                1555                1560

Leu Phe Thr Leu Thr Asn Leu Gly Ala Pro Ala Ala Phe Lys Tyr
        1565                1570                1575

Phe Asp Thr Thr Ile Asp Arg Lys Arg Tyr Thr Ser Thr Lys Glu
        1580                1585                1590

Val Leu Asp Ala Thr Leu Ile His Gln Ser Ile Thr Gly Leu Tyr
        1595                1600                1605

Glu Thr Arg Ile Asp Leu Ser Gln Leu Gly Gly Asp Lys Arg Pro
        1610                1615                1620

Ala Ala Thr Lys Lys Ala Gly Gln Ala Lys Lys Lys Lys Thr Arg
        1625                1630                1635

Asp Ser Gly Gly Ser Thr Asn Leu Ser Asp Ile Ile Glu Lys Glu
        1640                1645                1650

Thr Gly Lys Gln Leu Val Ile Gln Glu Ser Ile Leu Met Leu Pro
        1655                1660                1665

Glu Glu Val Glu Glu Val Ile Gly Asn Lys Pro Glu Ser Asp Ile
        1670                1675                1680

Leu Val His Thr Ala Tyr Asp Glu Ser Thr Asp Glu Asn Val Met
        1685                1690                1695

Leu Leu Thr Ser Asp Ala Pro Glu Tyr Lys Pro Trp Ala Leu Val
        1700                1705                1710

Ile Gln Asp Ser Asn Gly Glu Asn Lys Ile Lys Met Leu Ser Gly
        1715                1720                1725
```

```
Gly Ser  Pro Lys Lys Lys Arg  Lys Val
    1730                1735

<210> SEQ ID NO 23
<211> LENGTH: 1737
<212> TYPE: PRT
<213> ORGANISM: Artificial Sequence
<220> FEATURE:
<223> OTHER INFORMATION: Description of Artificial Sequence: Synthetic
      fusion NLS-APOBEC1-XTEN-dCas9-UGI-NLS

<400> SEQUENCE: 23

Met Pro Lys Lys Arg Lys Val Ser Ser Glu Thr Gly Pro Val Ala
1               5                   10                  15

Val Asp Pro Thr Leu Arg Arg Arg Ile Glu Pro His Glu Phe Glu Val
            20                  25                  30

Phe Phe Asp Pro Arg Glu Leu Arg Lys Glu Thr Cys Leu Leu Tyr Glu
        35                  40                  45

Ile Asn Trp Gly Gly Arg His Ser Ile Trp Arg His Thr Ser Gln Asn
    50                  55                  60

Thr Asn Lys His Val Glu Val Asn Phe Ile Glu Lys Phe Thr Thr Glu
65                  70                  75                  80

Arg Tyr Phe Cys Pro Asn Thr Arg Cys Ser Ile Thr Trp Phe Leu Ser
                85                  90                  95

Trp Ser Pro Cys Gly Glu Cys Ser Arg Ala Ile Thr Glu Phe Leu Ser
            100                 105                 110

Arg Tyr Pro His Val Thr Leu Phe Ile Tyr Ile Ala Arg Leu Tyr His
        115                 120                 125

His Ala Asp Pro Arg Asn Arg Gln Gly Leu Arg Asp Leu Ile Ser Ser
    130                 135                 140

Gly Val Thr Ile Gln Ile Met Thr Glu Gln Glu Ser Gly Tyr Cys Trp
145                 150                 155                 160

Arg Asn Phe Val Asn Tyr Ser Pro Ser Asn Glu Ala His Trp Pro Arg
                165                 170                 175

Tyr Pro His Leu Trp Val Arg Leu Tyr Val Leu Glu Leu Tyr Cys Ile
            180                 185                 190

Ile Leu Gly Leu Pro Pro Cys Leu Asn Ile Leu Arg Arg Lys Gln Pro
        195                 200                 205

Gln Leu Thr Phe Phe Thr Ile Ala Leu Gln Ser Cys His Tyr Gln Arg
    210                 215                 220

Leu Pro Pro His Ile Leu Trp Ala Thr Gly Leu Lys Ser Gly Ser Glu
225                 230                 235                 240

Thr Pro Gly Thr Ser Glu Ser Ala Thr Pro Glu Leu Lys Asp Lys Lys
                245                 250                 255

Tyr Ser Ile Gly Leu Ala Ile Gly Thr Asn Ser Val Gly Trp Ala Val
            260                 265                 270

Ile Thr Asp Glu Tyr Lys Val Pro Ser Lys Lys Phe Lys Val Leu Gly
        275                 280                 285

Asn Thr Asp Arg His Ser Ile Lys Lys Asn Leu Ile Gly Ala Leu Leu
    290                 295                 300

Phe Asp Ser Gly Glu Thr Ala Glu Ala Thr Arg Leu Lys Arg Thr Ala
305                 310                 315                 320

Arg Arg Arg Tyr Thr Arg Arg Lys Asn Arg Ile Cys Tyr Leu Gln Glu
                325                 330                 335

Ile Phe Ser Asn Glu Met Ala Lys Val Asp Asp Ser Phe Phe His Arg
```

-continued

```
                340                 345                 350
Leu Glu Glu Ser Phe Leu Val Glu Glu Asp Lys Lys His Glu Arg His
            355                 360                 365
Pro Ile Phe Gly Asn Ile Val Asp Glu Val Ala Tyr His Glu Lys Tyr
        370                 375                 380
Pro Thr Ile Tyr His Leu Arg Lys Lys Leu Val Asp Ser Thr Asp Lys
385                 390                 395                 400
Ala Asp Leu Arg Leu Ile Tyr Leu Ala Leu Ala His Met Ile Lys Phe
                405                 410                 415
Arg Gly His Phe Leu Ile Glu Gly Asp Leu Asn Pro Asp Asn Ser Asp
            420                 425                 430
Val Asp Lys Leu Phe Ile Gln Leu Val Gln Thr Tyr Asn Gln Leu Phe
        435                 440                 445
Glu Glu Asn Pro Ile Asn Ala Ser Gly Val Asp Ala Lys Ala Ile Leu
    450                 455                 460
Ser Ala Arg Leu Ser Lys Ser Arg Arg Leu Glu Asn Leu Ile Ala Gln
465                 470                 475                 480
Leu Pro Gly Glu Lys Lys Asn Gly Leu Phe Gly Asn Leu Ile Ala Leu
                485                 490                 495
Ser Leu Gly Leu Thr Pro Asn Phe Lys Ser Asn Phe Asp Leu Ala Glu
            500                 505                 510
Asp Ala Lys Leu Gln Leu Ser Lys Asp Thr Tyr Asp Asp Asp Leu Asp
        515                 520                 525
Asn Leu Leu Ala Gln Ile Gly Asp Gln Tyr Ala Asp Leu Phe Leu Ala
    530                 535                 540
Ala Lys Asn Leu Ser Asp Ala Ile Leu Leu Ser Asp Ile Leu Arg Val
545                 550                 555                 560
Asn Thr Glu Ile Thr Lys Ala Pro Leu Ser Ala Ser Met Ile Lys Arg
                565                 570                 575
Tyr Asp Glu His His Gln Asp Leu Thr Leu Leu Lys Ala Leu Val Arg
            580                 585                 590
Gln Gln Leu Pro Glu Lys Tyr Lys Glu Ile Phe Phe Asp Gln Ser Lys
        595                 600                 605
Asn Gly Tyr Ala Gly Tyr Ile Asp Gly Gly Ala Ser Gln Glu Glu Phe
    610                 615                 620
Tyr Lys Phe Ile Lys Pro Ile Leu Glu Lys Met Asp Gly Thr Glu Glu
625                 630                 635                 640
Leu Leu Val Lys Leu Asn Arg Glu Asp Leu Leu Arg Lys Gln Arg Thr
                645                 650                 655
Phe Asp Asn Gly Ser Ile Pro His Gln Ile His Leu Gly Glu Leu His
            660                 665                 670
Ala Ile Leu Arg Arg Gln Glu Asp Phe Tyr Pro Phe Leu Lys Asp Asn
        675                 680                 685
Arg Glu Lys Ile Glu Lys Ile Leu Thr Phe Arg Ile Pro Tyr Tyr Val
    690                 695                 700
Gly Pro Leu Ala Arg Gly Asn Ser Arg Phe Ala Trp Met Thr Arg Lys
705                 710                 715                 720
Ser Glu Glu Thr Ile Thr Pro Trp Asn Phe Glu Glu Val Val Asp Lys
                725                 730                 735
Gly Ala Ser Ala Gln Ser Phe Ile Glu Arg Met Thr Asn Phe Asp Lys
            740                 745                 750
Asn Leu Pro Asn Glu Lys Val Leu Pro Lys His Ser Leu Leu Tyr Glu
        755                 760                 765
```

```
Tyr Phe Thr Val Tyr Asn Glu Leu Thr Lys Val Lys Tyr Val Thr Glu
    770                 775                 780
Gly Met Arg Lys Pro Ala Phe Leu Ser Gly Glu Gln Lys Lys Ala Ile
785                 790                 795                 800
Val Asp Leu Leu Phe Lys Thr Asn Arg Lys Val Thr Val Lys Gln Leu
                    805                 810                 815
Lys Glu Asp Tyr Phe Lys Lys Ile Glu Cys Phe Asp Ser Val Glu Ile
                820                 825                 830
Ser Gly Val Glu Asp Arg Phe Asn Ala Ser Leu Gly Thr Tyr His Asp
            835                 840                 845
Leu Leu Lys Ile Ile Lys Asp Lys Asp Phe Leu Asp Asn Glu Glu Asn
    850                 855                 860
Glu Asp Ile Leu Glu Asp Ile Val Leu Thr Leu Thr Leu Phe Glu Asp
865                 870                 875                 880
Arg Glu Met Ile Glu Glu Arg Leu Lys Thr Tyr Ala His Leu Phe Asp
                    885                 890                 895
Asp Lys Val Met Lys Gln Leu Lys Arg Arg Arg Tyr Thr Gly Trp Gly
                900                 905                 910
Arg Leu Ser Arg Lys Leu Ile Asn Gly Ile Arg Asp Lys Gln Ser Gly
            915                 920                 925
Lys Thr Ile Leu Asp Phe Leu Lys Ser Asp Gly Phe Ala Asn Arg Asn
    930                 935                 940
Phe Met Gln Leu Ile His Asp Asp Ser Leu Thr Phe Lys Glu Asp Ile
945                 950                 955                 960
Gln Lys Ala Gln Val Ser Gly Gln Gly Asp Ser Leu His Glu His Ile
                    965                 970                 975
Ala Asn Leu Ala Gly Ser Pro Ala Ile Lys Lys Gly Ile Leu Gln Thr
                980                 985                 990
Val Lys Val Val Asp Glu Leu Val  Lys Val Met Gly Arg His Lys Pro
            995                 1000                1005
Glu Asn Ile Val Ile Glu Met  Ala Arg Glu Asn Gln  Thr Thr Gln
        1010                1015                1020
Lys Gly Gln Lys Asn Ser Arg  Glu Arg Met Lys Arg  Ile Glu Glu
        1025                1030                1035
Gly Ile Lys Glu Leu Gly Ser  Gln Ile Leu Lys Glu  His Pro Val
        1040                1045                1050
Glu Asn Thr Gln Leu Gln Asn  Glu Lys Leu Tyr Leu  Tyr Tyr Leu
        1055                1060                1065
Gln Asn Gly Arg Asp Met Tyr  Val Asp Gln Glu Leu  Asp Ile Asn
        1070                1075                1080
Arg Leu Ser Asp Tyr Asp Val  Asp Ala Ile Val Pro  Gln Ser Phe
        1085                1090                1095
Leu Lys Asp Asp Ser Ile Asp  Asn Lys Val Leu Thr  Arg Ser Asp
        1100                1105                1110
Lys Asn Arg Gly Lys Ser Asp  Asn Val Pro Ser Glu  Glu Val Val
        1115                1120                1125
Lys Lys Met Lys Asn Tyr Trp  Arg Gln Leu Leu Asn  Ala Lys Leu
        1130                1135                1140
Ile Thr Gln Arg Lys Phe Asp  Asn Leu Thr Lys Ala  Glu Arg Gly
        1145                1150                1155
Gly Leu Ser Glu Leu Asp Lys  Ala Gly Phe Ile Lys  Arg Gln Leu
        1160                1165                1170
```

-continued

Val Glu Thr Arg Gln Ile Thr Lys His Val Ala Gln Ile Leu Asp
1175                1180                1185

Ser Arg Met Asn Thr Lys Tyr Asp Glu Asn Asp Lys Leu Ile Arg
1190                1195                1200

Glu Val Lys Val Ile Thr Leu Lys Ser Lys Leu Val Ser Asp Phe
1205                1210                1215

Arg Lys Asp Phe Gln Phe Tyr Lys Val Arg Glu Ile Asn Asn Tyr
1220                1225                1230

His His Ala His Asp Ala Tyr Leu Asn Ala Val Val Gly Thr Ala
1235                1240                1245

Leu Ile Lys Lys Tyr Pro Lys Leu Glu Ser Glu Phe Val Tyr Gly
1250                1255                1260

Asp Tyr Lys Val Tyr Asp Val Arg Lys Met Ile Ala Lys Ser Glu
1265                1270                1275

Gln Glu Ile Gly Lys Ala Thr Ala Lys Tyr Phe Phe Tyr Ser Asn
1280                1285                1290

Ile Met Asn Phe Phe Lys Thr Glu Ile Thr Leu Ala Asn Gly Glu
1295                1300                1305

Ile Arg Lys Arg Pro Leu Ile Glu Thr Asn Gly Glu Thr Gly Glu
1310                1315                1320

Ile Val Trp Asp Lys Gly Arg Asp Phe Ala Thr Val Arg Lys Val
1325                1330                1335

Leu Ser Met Pro Gln Val Asn Ile Val Lys Lys Thr Glu Val Gln
1340                1345                1350

Thr Gly Gly Phe Ser Lys Glu Ser Ile Leu Pro Lys Arg Asn Ser
1355                1360                1365

Asp Lys Leu Ile Ala Arg Lys Lys Asp Trp Asp Pro Lys Lys Tyr
1370                1375                1380

Gly Gly Phe Asp Ser Pro Thr Val Ala Tyr Ser Val Leu Val Val
1385                1390                1395

Ala Lys Val Glu Lys Gly Lys Ser Lys Lys Leu Lys Ser Val Lys
1400                1405                1410

Glu Leu Leu Gly Ile Thr Ile Met Glu Arg Ser Ser Phe Glu Lys
1415                1420                1425

Asn Pro Ile Asp Phe Leu Glu Ala Lys Gly Tyr Lys Glu Val Lys
1430                1435                1440

Lys Asp Leu Ile Ile Lys Leu Pro Lys Tyr Ser Leu Phe Glu Leu
1445                1450                1455

Glu Asn Gly Arg Lys Arg Met Leu Ala Ser Ala Gly Glu Leu Gln
1460                1465                1470

Lys Gly Asn Glu Leu Ala Leu Pro Ser Lys Tyr Val Asn Phe Leu
1475                1480                1485

Tyr Leu Ala Ser His Tyr Glu Lys Leu Lys Gly Ser Pro Glu Asp
1490                1495                1500

Asn Glu Gln Lys Gln Leu Phe Val Glu Gln His Lys His Tyr Leu
1505                1510                1515

Asp Glu Ile Ile Glu Gln Ile Ser Glu Phe Ser Lys Arg Val Ile
1520                1525                1530

Leu Ala Asp Ala Asn Leu Asp Lys Val Leu Ser Ala Tyr Asn Lys
1535                1540                1545

His Arg Asp Lys Pro Ile Arg Glu Gln Ala Glu Asn Ile Ile His
1550                1555                1560

Leu Phe Thr Leu Thr Asn Leu Gly Ala Pro Ala Ala Phe Lys Tyr

```
              1565                1570                1575
Phe Asp Thr Thr Ile Asp Arg Lys Arg Tyr Thr Ser Thr Lys Glu
        1580                1585                1590
Val Leu Asp Ala Thr Leu Ile His Gln Ser Ile Thr Gly Leu Tyr
        1595                1600                1605
Glu Thr Arg Ile Asp Leu Ser Gln Leu Gly Gly Asp Lys Arg Pro
        1610                1615                1620
Ala Ala Thr Lys Lys Ala Gly Gln Ala Lys Lys Lys Thr Arg
        1625                1630                1635
Asp Ser Gly Gly Ser Thr Asn Leu Ser Asp Ile Glu Lys Glu
        1640                1645                1650
Thr Gly Lys Gln Leu Val Ile Gln Glu Ser Ile Leu Met Leu Pro
        1655                1660                1665
Glu Glu Val Glu Glu Val Ile Gly Asn Lys Pro Glu Ser Asp Ile
        1670                1675                1680
Leu Val His Thr Ala Tyr Asp Glu Ser Thr Asp Glu Asn Val Met
        1685                1690                1695
Leu Leu Thr Ser Asp Ala Pro Glu Tyr Lys Pro Trp Ala Leu Val
        1700                1705                1710
Ile Gln Asp Ser Asn Gly Glu Asn Lys Ile Lys Met Leu Ser Gly
        1715                1720                1725
Gly Ser Pro Lys Lys Lys Arg Lys Val
        1730                1735
```

<210> SEQ ID NO 24
<211> LENGTH: 474
<212> TYPE: DNA
<213> ORGANISM: Artificial Sequence
<220> FEATURE:
<223> OTHER INFORMATION: Description of Artificial Sequence: Synthetic
      ZmCENH3 encoding sequence

<400> SEQUENCE: 24

```
atggctcgaa ccaagcacca ggccgtgagg aagacggcgg agaagcccaa gaagaagctc      60
cagttcgagc gctcaggtgg tgcgagtacc tcggcgacgc cggaaagggc tgctgggacc     120
gggggaagag cggcgtctgg aggtgactca gttaagaaga cgaaaccacg ccaccgctgg     180
cggccaggga ctgtagcgct gcgggagatc aggaagtacc agaagtccac tgaaccgctc     240
atccccttg cgcctttcgt ccgtgtggtg agggagttaa ccaatttcgt aacaaacggg     300
aaagtagagc gctataccgc agaagccctc cttgcgctgc aagaggcagc agaattccac     360
ttgatagaac tgtttgaaat ggcgaatctg tgtgccatcc atgccaagcg tgtcacaatc     420
atgcaaaagg acatacaact tgcaaggcgt atcggaggaa ggcgttgggc atga            474
```

<210> SEQ ID NO 25
<211> LENGTH: 157
<212> TYPE: PRT
<213> ORGANISM: Artificial Sequence
<220> FEATURE:
<223> OTHER INFORMATION: Description of Artificial Sequence: Synthetic
      ZmCENH3

<400> SEQUENCE: 25

```
Met Ala Arg Thr Lys His Gln Ala Val Arg Lys Thr Ala Glu Lys Pro
1               5                   10                  15
Lys Lys Lys Leu Gln Phe Glu Arg Ser Gly Gly Ala Ser Thr Ser Ala
            20                  25                  30
```

```
Thr Pro Glu Arg Ala Ala Gly Thr Gly Gly Arg Ala Ala Ser Gly Gly
             35                  40                  45

Asp Ser Val Lys Lys Thr Lys Pro Arg His Arg Trp Arg Pro Gly Thr
 50                  55                  60

Val Ala Leu Arg Glu Ile Arg Lys Tyr Gln Lys Ser Thr Glu Pro Leu
 65                  70                  75                  80

Ile Pro Phe Ala Pro Phe Val Arg Val Val Arg Glu Leu Thr Asn Phe
                 85                  90                  95

Val Thr Asn Gly Lys Val Glu Arg Tyr Thr Ala Glu Ala Leu Leu Ala
                100                 105                 110

Leu Gln Glu Ala Ala Glu Phe His Leu Ile Glu Leu Phe Glu Met Ala
            115                 120                 125

Asn Leu Cys Ala Ile His Ala Lys Arg Val Thr Ile Met Gln Lys Asp
        130                 135                 140

Ile Gln Leu Ala Arg Arg Ile Gly Gly Arg Arg Trp Ala
145                 150                 155

<210> SEQ ID NO 26
<211> LENGTH: 1917
<212> TYPE: DNA
<213> ORGANISM: Artificial Sequence
<220> FEATURE:
<223> OTHER INFORMATION: Description of Artificial Sequence: Synthetic
      ZmALS1 encoding sequence

<400> SEQUENCE: 26
atggccaccg ccgccaccgc ggccgccgcg ctcaccggcg ccactaccgc tacgcccaag     60
tcgaggcgcc gagcccacca cttggccacc cggcgcgccc tcgccgcgcc catcaggtgc    120
tcagcgttgt cacgcgccac gccgacggct ccccggcca ctccgctacg tccgtggggc    180
cccaacgagc cccgcaaggg ctccgacatc ctcgtcgagg ctctcgagcg ctgtggcgtc    240
cgtgacgtct tcgcctaccc cggcggcgca tccatggaga tccaccaggc actcacccgc    300
tcccccgtca tcgccaacca cctcttccgc acgaacaag gggaggcctt cgccgcctcc    360
ggctacgcgc gctcctcggg ccgcgttggc gtctgcatcg ccacctccgg ccccggcgcc    420
accaacctag tctctgcgct cgcagacgcg ttgctcgact ccgtcccat gtcgccatc    480 acgggacagg tgccgcgacg catgattggc accgacgcct tcaggagac gccatcgtc    540 gaggtcaccc gctccatcac caagcacaac tacctggtcc tcgacgtcga cgacatcccc    600
cgcgtcgtgc aggaggcctt cttcctcgca tcctctggtc gcccggggcc ggtgcttgtt    660
gacatcccca aggacatcca gcagcagatg gcggtgccgg cctgggacac gcccatgagt    720
ctgcctgggt acatcgcgcg ccttcccaag cctcccgcga ctgaatttct tgagcaggtg    780
ctgcgtcttg ttggtgaatc acggcgccct gttctttatg ttggcggtgg ctgtgcagca    840
tcaggtgagg agttgtgccg ctttgtggag ttgactggaa tcccagtcac aactactctt    900
atgggccttg caacttccc cagcgacgac ccactgtcac tgcgcatgct ggtatgcat    960 ggcacagtgt atgcaaatta tgcagtggat aaggccgatc tgttgcttgc atttggtgtg   1020
cggtttgatg atcgtgtgac agggaaaatt gaggcttttg caggcagagc taagattgtg   1080
cacattgata ttgatcctgc tgagattggc aagaacaagc agccacatgt gtccatctgt   1140
gcagatgtta agcttgcttt cagggcatg aatactcttc tggaaggaag cacatcaaag   1200
aagagctttg acttcggctc atggcatgat gaattggat agcaaaagcg ggagtttccc   1260
cttgggtata aaatcttcaa tgaggaaatc cagccacaat atgctattca ggttcttgat   1320
```

-continued

```
gagttgacga agggagaaggc catcattgcc acaggtgttg ggcagcacca gatgtgggcg    1380
gcacagtatt acacttacaa gcggccaagg cagtggctgt cttcagctgg tcttggggct    1440
atgggatttg gtttgccggc tgctgctggt gctgctgtgg ccaacccagg tgtcactgtt    1500
gttgacatcg acggagatgg tagcttcctc atgaacattc aggagctagc tatgatccgt    1560
attgagaacc tcccagtcaa ggtctttgtg ctaaacaacc agcacctcgg gatggtggtg    1620
cagtgggagg acaggttcta taaggccaat agagcacaca cattcttggg aaacccagag    1680
aacgaaagtg agatatatcc agattttgtg gcaattgcca aagggttcaa cattccagca    1740
gtccgtgtga caaagaagag cgaagtccat gcagcaatca gaagatgct tgaggctcca    1800 gggccgtacc tcttggatat aatcgtcccg caccaggagc atgtgttgcc tatgatccct    1860
agtggtgggg ctttcaagga tatgatcctg gatggtgatg gcaggactgt gtattga       1917
```

<210> SEQ ID NO 27
<211> LENGTH: 638
<212> TYPE: PRT
<213> ORGANISM: Artificial Sequence
<220> FEATURE:
<223> OTHER INFORMATION: Description of Artificial Sequence: Synthetic ZmALS1

<400> SEQUENCE: 27

```
Met Ala Thr Ala Ala Thr Ala Ala Ala Leu Thr Gly Ala Thr Thr
1               5                   10                  15

Ala Thr Pro Lys Ser Arg Arg Ala His His Leu Ala Thr Arg Arg
                20                  25                  30

Ala Leu Ala Ala Pro Ile Arg Cys Ser Ala Leu Ser Arg Ala Thr Pro
                35                  40                  45

Thr Ala Pro Pro Ala Thr Pro Leu Arg Pro Trp Gly Pro Asn Glu Pro
    50                  55                  60

Arg Lys Gly Ser Asp Ile Leu Val Glu Ala Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
                100                 105                 110

Gln Gly Glu Ala Phe Ala Ala Ser Gly Tyr Ala Arg Ser Ser Gly Arg
            115                 120                 125

Val Gly Val Cys Ile Ala Thr Ser Gly Pro Gly Ala Thr Asn Leu Val
        130                 135                 140

Ser Ala Leu Ala Asp Ala Leu Leu Asp Ser Val Pro Ile Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
                180                 185                 190

Val Leu Asp Val Asp Asp Ile Pro Arg Val Val Gln Glu Ala Phe Phe
            195                 200                 205

Leu Ala Ser Ser Gly Arg Pro Gly Pro Val Leu Val Asp Ile Pro Lys
        210                 215                 220

Asp Ile Gln Gln Gln Met Ala Val Pro Ala Trp Asp Thr Pro Met Ser
225                 230                 235                 240

Leu Pro Gly Tyr Ile Ala Arg Leu Pro Lys Pro Pro Ala Thr Glu Phe
                245                 250                 255
```

Leu Glu Gln Val Leu Arg Leu Val Gly Ser Arg Arg Pro Val Leu
            260                 265                 270

Tyr Val Gly Gly Cys Ala Ala Ser Gly Glu Glu Leu Cys Arg Phe
        275                 280                 285

Val Glu Leu Thr Gly Ile Pro Val Thr Thr Leu Met Gly Leu Gly
    290                 295                 300

Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
                325                 330                 335

Ala Phe Gly Val Arg Phe Asp Asp Arg Val Thr Gly Lys Ile Glu Ala
                340                 345                 350

Phe Ala Gly Arg Ala Lys Ile Val His Ile Asp Ile Asp Pro Ala Glu
                355                 360                 365

Ile Gly Lys Asn Lys Gln Pro His Val Ser Ile Cys Ala Asp Val Lys
                370                 375                 380

Leu Ala Leu Gln Gly Met Asn Thr Leu Leu Glu Gly Ser Thr Ser Lys
385                 390                 395                 400

Lys Ser Phe Asp Phe Gly Ser Trp His Asp Glu Leu Asp Gln Gln Lys
                405                 410                 415

Arg Glu Phe Pro Leu Gly Tyr Lys Ile Phe Asn Glu Glu Ile Gln Pro
                420                 425                 430

Gln Tyr Ala Ile Gln Val Leu Asp Glu Leu Thr Lys Gly Lys Ala Ile
                435                 440                 445

Ile Ala Thr Gly Val Gly Gln His Gln Met Trp Ala Ala Gln Tyr Tyr
                450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Gly Ala Ala Val Ala Asn Pro
                485                 490                 495

Gly Val Thr Val Val Asp Ile Asp Gly Asp Gly Ser Phe Leu Met Asn
                500                 505                 510

Ile Gln Glu Leu Ala Met Ile Arg Ile Glu Asn Leu Pro Val Lys Val
                515                 520                 525

Phe Val Leu Asn Asn Gln His Leu Gly Met Val Val Gln Trp Glu Asp
530                 535                 540

Arg Phe Tyr Lys Ala Asn Arg Ala His Thr Phe Leu Gly Asn Pro Glu
545                 550                 555                 560

Asn Glu Ser Glu Ile Tyr Pro Asp Phe Val Ala Ile Ala Lys Gly Phe
                565                 570                 575

Asn Ile Pro Ala Val Arg Val Thr Lys Lys Ser Glu Val His Ala Ala
                580                 585                 590

Ile Lys Lys Met Leu Glu Ala Pro Gly Pro Tyr Leu Leu Asp Ile Ile
                595                 600                 605

Val Pro His Gln Glu His Val Leu Pro Met Ile Pro Ser Gly Gly Ala
                610                 615                 620

Phe Lys Asp Met Ile Leu Asp Gly Asp Gly Arg Thr Val Tyr
625                 630                 635

<210> SEQ ID NO 28
<211> LENGTH: 1917
<212> TYPE: DNA
<213> ORGANISM: Artificial Sequence
<220> FEATURE:
<223> OTHER INFORMATION: Description of Artificial Sequence: Synthetic ZmALS2 encoding sequence

<400> SEQUENCE: 28

```
atggccaccg ccgccgccgc gtctaccgcg ctcactggcg ccactaccgc tgcgcccaag      60
gcgaggcgcc gggcgcacct cctgccacc cgccgcgccc tcgccgcgcc catcaggtgc     120
tcagcggcgt caccgccat gccgatggct ccccggcca ccccgctccg gccgtgggc      180
cccaccgatc cccgcaaggg cgccgacatc tcgtcgagt ccctcgagcg ctgcggcgtc     240
cgcgacgtct tcgcctaccc cggcggcgcg tccatggaga tccaccaggc actcacccgc     300
tcccccgtca tcgccaacca cctcttccgc cacgagcaag gggaggcctt tgcggcctcc     360
ggctacgcgc gctcctcggg ccgcgtcggc gtctgcatcg ccacctccgg ccccggcgcc     420
accaaccttg tctccgcgct cgccgacgcg ctgctcgatt ccgtccccat ggtcgccatc     480
acgggacagg tgccgcgacg catgattggc accgacgcct ccaggagac gcccatcgtc     540
gaggtcaccc gctccatcac caagcacaac tacctggtcc tcgacgtcga cgacatcccc     600
cgcgtcgtgc aggaggcttt cttcctcgcc tcctctggtc gaccgggggcc ggtgcttgtc     660
gacatcccca aggacatcca gcagcagatg gcggtgcctg tctgggacaa gcccatgagt     720
ctgcctgggt acattgcgcg ccttcccaag ccccctgcga ctgagttgct tgagcaggtg     780
ctgcgtcttg ttggtgaatc ccggcgcccct gttctttatg ttggcggtgg ctgcgcagca     840
tctggtgagg agttgcgacg ctttgtggag ctgactggaa tcccggtcac aactactctt     900
atgggcctcg gcaacttccc cagcgacgac ccactgtctc tgcgcatgct aggtatgcat     960
ggcacggtgt atgcaaatta tgcagtggat aaggccgatc tgttgcttgc acttggtgtg    1020
cggtttgatg atcgtgtgac agggaagatt gaggcttttg caagcagggc taagattgtg    1080
cacgttgata ttgatccggc tgagattggc aagaacaagc agccacatgt gtccatctgt    1140
gcagatgtta agcttgcttt gcagggcatg aatgctcttc ttgaaggaag cacatcaaag    1200
aagagctttg actttggctc atggaacgat gagttggatc agcagaagag ggaattcccc    1260
cttgggtata aacatctaa tgaggagatc cagccacaat atgctattca ggttcttgat    1320
gagctgacga aggcgaggc catcatcggc acaggtgttg gcagcacca gatgtgggcg    1380
gcacagtact acacttacaa gcggccaagg cagtggttgt cttcagctgg tcttggggct    1440
atgggatttg gtttgccggc tgctgctggt gcttctgtgg ccaacccagg tgttactgtt    1500
gttgacatcg atggagatgg tagctttctc atgaacgttc aggagctagc tatgatccga    1560
attgagaacc tcccggtgaa ggtctttgtg ctaaacaacc agcacctggg gatggtggtg    1620
cagtgggagg acaggttcta taaggccaac agagcgcaca catacttggg aaacccagag    1680
aatgaaagtg agatatatcc agatttcgtg acgatcgcca aagggttcaa cattccagcg    1740
gtccgtgtga caaagaagaa cgaagtccgc gcagcgataa agaagatgct cgagactcca    1800
gggccgtacc tcttggatat aatcgtccca caccaggagc atgtgttgcc tatgatccct    1860
agtggtgggg ctttcaagga tatgatcctg gatggtgatg gcaggactgt gtactga        1917
```

<210> SEQ ID NO 29
<211> LENGTH: 638
<212> TYPE: PRT
<213> ORGANISM: Artificial Sequence
<220> FEATURE:
<223> OTHER INFORMATION: Description of Artificial Sequence: Synthetic ZmALS2

<400> SEQUENCE: 29

-continued

```
Met Ala Thr Ala Ala Ala Ser Thr Ala Leu Thr Gly Ala Thr Thr
1               5                   10                  15

Ala Ala Pro Lys Ala Arg Arg Arg Ala His Leu Leu Ala Thr Arg Arg
                20                  25                  30

Ala Leu Ala Ala Pro Ile Arg Cys Ser Ala Ala Ser Pro Ala Met Pro
            35                  40                  45

Met Ala Pro Pro Ala Thr Pro Leu Arg Pro Trp Gly Pro Thr Asp Pro
50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Val Trp Asp Lys Pro Met Ser
225                 230                 235                 240

Leu Pro Gly Tyr Ile Ala Arg Leu Pro Lys Pro Pro Ala Thr Glu Leu
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Arg Arg Phe
        275                 280                 285

Val Glu Leu Thr Gly Ile Pro Val Thr Thr Thr Leu Met Gly Leu Gly
    290                 295                 300

Asn Phe Pro Ser Asp Asp Pro Leu Ser Leu Arg Met Leu Gly Met His
305                 310                 315                 320

Gly Thr Val Tyr Ala Asn Tyr Ala Val Asp Lys Ala Asp Leu Leu Leu
                325                 330                 335

Ala Leu Gly Val Arg Phe Asp Asp Arg Val Thr Gly Lys Ile Glu Ala
            340                 345                 350

Phe Ala Ser Arg Ala Lys Ile Val His Val Asp Ile Asp Pro Ala Glu
        355                 360                 365

Ile Gly Lys Asn Lys Gln Pro His Val Ser Ile Cys Ala Asp Val Lys
    370                 375                 380

Leu Ala Leu Gln Gly Met Asn Ala Leu Leu Glu Gly Ser Thr Ser Lys
385                 390                 395                 400

Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
```

```
                    420                 425                 430
Gln Tyr Ala Ile Gln Val Leu Asp Glu Leu Thr Lys Gly Glu Ala Ile
                435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Gly Ala Ser Val Ala Asn Pro
                485                 490                 495

Gly Val Thr Val Val Asp Ile Asp Gly Asp Gly Ser Phe Leu Met Asn
                500                 505                 510

Val Gln Glu Leu Ala Met Ile Arg Ile Glu Asn Leu Pro Val Lys Val
                515                 520                 525

Phe Val Leu Asn Asn Gln His Leu Gly Met Val Val Gln Trp Glu Asp
                530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Asn Glu Val Arg Ala Ala
                580                 585                 590

Ile Lys Lys Met Leu Glu Thr Pro Gly Pro Tyr Leu Leu Asp Ile Ile
                595                 600                 605

Val Pro His Gln Glu His Val Leu Pro Met Ile Pro Ser Gly Gly Ala
                610                 615                 620

Phe Lys Asp Met Ile Leu Asp Gly Asp Gly Arg Thr Val Tyr
625                 630                 635

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      N terminal NLS

<400> SEQUENCE: 30

Pro Lys Lys Lys Arg Lys Val
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      C terminal NLS

<400> SEQUENCE: 31

Ser Gly Gly Ser Pro Lys Lys Lys Arg Lys Val
1               5                   10

<210> SEQ ID NO 32
<211> LENGTH: 42
<212> TYPE: PRT
<213> ORGANISM: Arabidopsis thaliana

<400> SEQUENCE: 32

Thr His Met Leu Ala Pro Pro Gln Ile Asn Arg Trp Thr Ala Glu Ala
1               5                   10                  15
```

```
Leu Val Ala Leu Gln Glu Ala Ala Glu Asp Tyr Leu Val Gly Leu Phe
            20                  25                  30

Ser Asp Ser Met Leu Cys Ala Ile His Ala
            35                  40

<210> SEQ ID NO 33
<211> LENGTH: 48
<212> TYPE: PRT
<213> ORGANISM: Hordeum vulgare

<400> SEQUENCE: 33

Ala Asp Asn Leu Thr Pro Leu Ser Asn Lys Lys Glu Ser Lys Pro Thr
1               5                   10                  15

Pro Trp Thr Pro Leu Ala Leu Leu Ser Leu Gln Glu Ser Ala Glu Tyr
            20                  25                  30

His Leu Val Asp Leu Phe Gly Lys Ala Asn Leu Cys Ala Ile His Ser
            35                  40                  45

<210> SEQ ID NO 34
<211> LENGTH: 42
<212> TYPE: PRT
<213> ORGANISM: Zea mays

<400> SEQUENCE: 34

Thr Asn Phe Val Thr Asn Gly Lys Val Glu Arg Tyr Thr Ala Glu Ala
1               5                   10                  15

Leu Leu Ala Leu Gln Glu Ala Ala Glu Phe His Leu Ile Glu Leu Phe
            20                  25                  30

Glu Met Ala Asn Leu Cys Ala Ile His Ala
            35                  40

<210> SEQ ID NO 35
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Thr Asn Phe Val Thr Asn Gly Lys Val Glu Arg Tyr Thr Ala Glu Ala
1               5                   10                  15

Phe Leu Ala Leu Gln Glu Ala Ala Glu Phe His Leu Ile Glu Leu Phe
            20                  25                  30

Glu Met Ala Asn Leu Cys Ala Ile His Ala
            35                  40

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr Asn Phe Val Thr Asn Gly Lys Val Glu Arg Tyr Thr Ala Glu Val
1               5                   10                  15

Leu Leu Ala Leu Gln Glu Ala Ala Glu Phe His Leu Ile Glu Leu Phe
            20                  25                  30

Glu Met Ala Asn Leu Cys Ala Ile His Ala
```

35                  40

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Asn Phe Val Thr Asn Gly Lys Val Glu Arg Tyr Thr Ala Glu Ala
1               5                   10                  15

Leu Phe Ala Leu Gln Glu Ala Ala Glu Phe His Leu Ile Glu Leu Phe
            20                  25                  30

Glu Met Ala Asn Leu Cys Ala Ile His Ala
        35                  40

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Thr Asn Phe Val Thr Asn Gly Lys Val Glu Arg Tyr Thr Ala Glu Ala
1               5                   10                  15

Phe Phe Ala Leu Gln Glu Ala Ala Glu Phe His Leu Ile Glu Leu Phe
            20                  25                  30

Glu Met Ala Asn Leu Cys Ala Ile His Ala
        35                  40

<210> SEQ ID NO 39
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Thr Asn Phe Val Thr Asn Gly Lys Val Glu Arg Tyr Thr Ala Glu Val
1               5                   10                  15

Phe Leu Ala Leu Gln Glu Ala Ala Glu Phe His Leu Ile Glu Leu Phe
            20                  25                  30

Glu Met Ala Asn Leu Cys Ala Ile His Ala
        35                  40

<210> SEQ ID NO 40
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Thr Asn Phe Val Thr Asn Gly Lys Val Glu Arg Tyr Thr Ala Glu Val
1               5                   10                  15

Leu Phe Ala Leu Gln Glu Ala Ala Glu Phe His Leu Ile Glu Leu Phe
            20                  25                  30

```
Glu Met Ala Asn Leu Cys Ala Ile His Ala
        35                  40
```

<210> SEQ ID NO 41
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Thr Asn Phe Val Thr Asn Gly Lys Val Glu Arg Tyr Thr Ala Glu Val
1               5                   10                  15

Phe Phe Ala Leu Gln Glu Ala Ala Glu Phe His Leu Ile Glu Leu Phe
            20                  25                  30

Glu Met Ala Asn Leu Cys Ala Ile His Ala
        35                  40
```

<210> SEQ ID NO 42
<211> LENGTH: 43
<212> TYPE: DNA
<213> ORGANISM: Triticum aestivum

<400> SEQUENCE: 42
gccgttcctg gtcgacatca acaacctcga cggcagcttc gtg                         43

<210> SEQ ID NO 43
<211> LENGTH: 59
<212> TYPE: DNA
<213> ORGANISM: Oryza sativa

<400> SEQUENCE: 43
accgagttta ggttcgctga ccagccagcg tctggcgccg gcgccgccgc tgaccccctt       59

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
accgagttta ggttcgctga ctagccagcg tctggcgccg gcgccgccgc tgaccccctt       59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
accgagttta ggttcgctga ttagccagcg tctggcgccg gcgccgccgc tgaccccctt       59

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
accgagttta ggttcgctga ccagtcagcg tctggcgccg gcgccgccgc tgacccctt    59

<210> SEQ ID NO 47
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
accgagttta ggttcgctga tcagccagcg tctggcgccg gcgccgccgc tgacccctt    59

<210> SEQ ID NO 48
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
accgagttta ggttcgctga ccagtcagcg tctggcgccg gcgccgccgc tgacccctt    59

<210> SEQ ID NO 49
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
accgagttta ggttcgctga ctagccagcg tctggcgccg gcgccgccgc tgacccctt    59

<210> SEQ ID NO 50
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accgagttta ggttcgctga ccagttagcg tctggcgccg gcgccgccgc tgacccctt    59

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
accgagttta ggttcgctga ctagccagcg tctggcgccg gcgccgccgc tgacccctt    59

<210> SEQ ID NO 52
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
accgagttta ggttcgctga ttagtcagcg tctggcgccg gcgccgccgc tgacccctt    59

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
accgagttta ggttcgctga ccagctagcg tctggcgccg gcgccgccgc tgacccctt    59

<210> SEQ ID NO 54
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
accgagttta ggttcgctga ttagccagcg tctggcgccg gcgccgccgc tgacccctt    59

<210> SEQ ID NO 55
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
accgagttta ggttcgctga ccagtcagcg tctggcgccg gcgccgccgc tgacccctt    59

<210> SEQ ID NO 56
<211> LENGTH: 23
<212> TYPE: DNA
<213> ORGANISM: Zea mays

<400> SEQUENCE: 56
caggtgccgc gacgcatgat tgg                                          23

<210> SEQ ID NO 57
<211> LENGTH: 44
<212> TYPE: DNA
<213> ORGANISM: Zea mays

<400> SEQUENCE: 57
ccatcacggg acaggtgccg cgacgcatga ttggcaccga cgcc                   44

<210> SEQ ID NO 58
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ccatcacggg acaggtgtcg cgacgcatga ttggcaccga cgcc                   44

<210> SEQ ID NO 59
<211> LENGTH: 44
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 59
ccatcacggg acaggtgttg cgacgcatga ttggcaccga cgcc                    44

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ccatcacggg acaggtgctg cgacgcatga ttggcaccga cgcc                    44

<210> SEQ ID NO 61
<211> LENGTH: 23
<212> TYPE: DNA
<213> ORGANISM: Oryza sativa

<400> SEQUENCE: 61
gaccagccag cgtctggcgc cgg                                           23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
acccacggcg tgcagtgctt cag                                           23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acccacggcg tgcagtgctt cgg                                           23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
acctacggcg tgcagtgctt cgg                                           23

<210> SEQ ID NO 65
<211> LENGTH: 23
<212> TYPE: DNA
<213> ORGANISM: Triticum aestivum

<400> SEQUENCE: 65
gtcgacatca acaacctcga cgg                                           23
```

<210> SEQ ID NO 66
<211> LENGTH: 23
<212> TYPE: DNA
<213> ORGANISM: Oryza sativa

<400> SEQUENCE: 66
gaccagccag cgtctggcgc cgg                                             23

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Gly Gly Ser
1               5

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Gly Gly Ser Gly Gly Gly Gly Ser Gly Gly Gly Gly Ser
1               5                   10                  15

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Lys Arg Lys Val
1               5

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 71
aagaagagaa aggtc                                                    15

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cccaagaaga agaggaaggt g                                             21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccaaagaaga agaggaaggt t                                             21

<210> SEQ ID NO 74
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74 tcgggggga gcccaaagaa gaagcggaag gtg                                 33

<210> SEQ ID NO 75
<211> LENGTH: 23
<212> TYPE: DNA
<213> ORGANISM: Zea mays

<400> SEQUENCE: 75
agccctcctt gcgctgcaag agg                                           23

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gattagtcag cgtcg                                                    15

<210> SEQ ID NO 77
<211> LENGTH: 23
<212> TYPE: DNA
<213> ORGANISM: Oryza sativa

<400> SEQUENCE: 77
acccacggcg tgcagtgctt cgg                                           23

<210> SEQ ID NO 78
<211> LENGTH: 23
```

```
<212> TYPE: DNA
<213> ORGANISM: Triticum aestivum

<400> SEQUENCE: 78
acccacggcg tgcagtgctt cgg                                              23

<210> SEQ ID NO 79
<211> LENGTH: 23
<212> TYPE: DNA
<213> ORGANISM: Zea mays

<400> SEQUENCE: 79
acccacggcg tgcagtgctt cgg                                              23

<210> SEQ ID NO 80
<211> LENGTH: 23
<212> TYPE: DNA
<213> ORGANISM: Oryza sativa

<400> SEQUENCE: 80
cggcgacggc gagcaagtgg agg                                              23

<210> SEQ ID NO 81
<211> LENGTH: 23
<212> TYPE: DNA
<213> ORGANISM: Oryza sativa

<400> SEQUENCE: 81
ctcttctgtc aacccagcca tgg                                              23

<210> SEQ ID NO 82
<211> LENGTH: 23
<212> TYPE: DNA
<213> ORGANISM: Triticum aestivum

<400> SEQUENCE: 82
cttcctgggc tacacgctca agg                                              23

<210> SEQ ID NO 83
<211> LENGTH: 23
<212> TYPE: DNA
<213> ORGANISM: Triticum aestivum

<400> SEQUENCE: 83
aaggacctca tccccatggg cgg                                              23

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggcaacccac ggcgtgcagt gctt                                             24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 85
cttgacccac ggcgtgcagt gctt                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
agcaacccac ggcgtgcagt gctt                                          24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggcagaccag ccagcgtctg gcgc                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggcacggcga cggcgagcaa gtgg                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcactcttc tgtcaaccca gcca                                          24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cttggtcgac atcaacaacc tcga                                          24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
```
cttgcttcct gggctacacg ctca                                          24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cttgaaggac ctcatcccca tggg                                          24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agcaagccct ccttgcgctg caag                                          24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aaacaagcac tgcacgccgt gggt                                          24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaacgcgcca gacgctggct ggtc                                          24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aaacccactt gctcgccgtc gccg                                          24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

```
aaactggctg ggttgacaga agag                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aaactcgagg ttgttgatgt cgac                                              24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaactgagcg tgtagcccag gaag                                              24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aaaccccatg gggatgaggt cctt                                              24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaccttgca gcgcaaggag ggct                                              24

<210> SEQ ID NO 102
<211> LENGTH: 23
<212> TYPE: DNA
<213> ORGANISM: Oryza sativa

<400> SEQUENCE: 102
gaccagccgg cgtgtggtgc agg                                               23

<210> SEQ ID NO 103
<211> LENGTH: 23
<212> TYPE: DNA
<213> ORGANISM: Oryza sativa

<400> SEQUENCE: 103
gaccagccag cgtctgaagg cgg                                               23

<210> SEQ ID NO 104
<211> LENGTH: 23
<212> TYPE: DNA
<213> ORGANISM: Oryza sativa
```

<400> SEQUENCE: 104
gaccaagcag cggctggcgc cgg                                        23

<210> SEQ ID NO 105
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acggcgtgca gtgcttcggc cgctaccccg acca                            34

<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tggtcggggt agcggccgaa gcactgcacg ccgt                            34

<210> SEQ ID NO 107
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggcttaagga caagaagtac tcgatcggcc t                               31

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gcgacgcgtc ttcttcttct ttgcttgccc tgc                             33

<210> SEQ ID NO 109
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cgggatccat gccaaagaag aagaggaagg tttcatc                         37

<210> SEQ ID NO 110
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ccgtgtacac tacaccttcc gcttcttctt tgggctc                     37

<210> SEQ ID NO 111
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aatacttgta tggccgcggc catgccaaag aagaagagg                   39

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
acttgtatgg aggcctgagc tctacacctt ccgcttctt                   39

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
atggtgagca agggcgagga g                                       21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cctcgatgtt gtggcggatc t                                       21

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cgatgtcgag ggcgatgcca cctac                                   25

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116

```
tggtcaaagt cgtgctgctt catgtgg                                          27
```

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

```
atcacgcgag ggcgatgcca cctac                                            25
```

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

```
gcctaaaagt cgtgctgctt catgtgg                                          27
```

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

```
agttcccgag ggcgatgcca cctac                                            25
```

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
ctctacaagt cgtgctgctt catgtgg                                          27
```

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
cactcacgag ggcgatgcca cctac                                            25
```

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
tgttggaagt cgtgctgctt catgtgg                                        27
```

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gtggcccgag ggcgatgcca cctac                                          25
```

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

```
cgaaacaagt cgtgctgctt catgtgg                                        27
```

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125

```
cgtacgcgag ggcgatgcca cctac                                          25
```

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126

```
ccactcaagt cgtgctgctt catgtgg                                        27
```

<210> SEQ ID NO 127
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127

```
ggtagcccga gggcgatgcc acctac                                         26
```

<210> SEQ ID NO 128
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

```
atcagtaagt cgtgctgctt catgtgg                                        27
```

<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
caccggccga gggcgatgcc acctac                                          26

<210> SEQ ID NO 130
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
atcgtgaagt cgtgctgctt catgtgg                                         27

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
atgagccgag ggcgatgcca cctac                                           25

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
aggaataagt cgtgctgctt catgtgg                                         27

<210> SEQ ID NO 133
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
caaaaggcga gggcgatgcc acctac                                          26

<210> SEQ ID NO 134
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tagttgaagt cgtgctgctt catgtgg                                         27

```
<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tcggcacgag ggcgatgcca cctac                                            25

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gaatgaaagt cgtgctgctt catgtgg                                          27

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tcccgacgag ggcgatgcca cctac                                            25

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cttcgaaagt cgtgctgctt catgtgg                                          27

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ttcaggacat cgagatggag aag                                              23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acaacgcaaa tctatccatg ctc                                              23
```

```
<210> SEQ ID NO 141
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cgatgtgccg acatccgcaa gtaccag                                              27

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tggtcatcat catcgtcagc tgcggc                                               26

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
atcacggccg acatccgcaa gtaccag                                              27

<210> SEQ ID NO 144
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gcctaatcat catcgtcagc tgcggc                                               26

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
agttccgccg acatccgcaa gtaccag                                              27

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ctctactcat catcgtcagc tgcggc                                               26

<210> SEQ ID NO 147
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cactcagccg acatccgcaa gtaccag                                          27

<210> SEQ ID NO 148
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tgttggtcat catcgtcagc tgcggc                                           26

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gatgtcacct gatgatctga agtagc                                           26

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
atgatggtgg tcgcccagat                                                  20

<210> SEQ ID NO 151
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cgatgtggtg caggttcctg gaccat                                           26

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tggtcaatga tggtggtcgc ccagat                                           26

<210> SEQ ID NO 153
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
atcacgggtg caggttcctg gaccat                                              26

<210> SEQ ID NO 154
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gcctaaatga tggtggtcgc ccagat                                              26

<210> SEQ ID NO 155
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
agttccggtg caggttcctg gaccat                                              26

<210> SEQ ID NO 156
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ctctacatga tggtggtcgc ccagat                                              26

<210> SEQ ID NO 157
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cactcaggtg caggttcctg gaccat                                              26

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tgttggatga tggtggtcgc ccagat                                              26

<210> SEQ ID NO 159
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 159
cgctgatgtg ttgtttgttg cga                                             23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cctgcagagc aagctcaagc tca                                             23

<210> SEQ ID NO 161
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cgatgttcgc tggcccaaat ctccct                                          26

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tggtcagaca tggctgcagc ctggtt                                          26

<210> SEQ ID NO 163
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
atcacgtcgc tggcccaaat ctccct                                          26

<210> SEQ ID NO 164
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcctaagaca tggctgcagc ctggtt                                          26

<210> SEQ ID NO 165
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 165
agttcctcgc tggcccaaat ctccct                                          26

<210> SEQ ID NO 166
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ctctacgaca tggctgcagc ctggtt                                          26

<210> SEQ ID NO 167
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cactcatcgc tggcccaaat ctccct                                          26

<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tgttgggaca tggctgcagc ctggtt                                          26

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
actccgtcta ccgaccattg ag                                              22

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tagaccatgg aggacatggg cat                                             23

<210> SEQ ID NO 171
<211> LENGTH: 27
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 171
gtggccaggg cctcaccgtg gagcaga                                           27

<210> SEQ ID NO 172
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cgaaactccc ctcgcaggaa gagcag                                            26

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
cgtacgaggg cctcaccgtg gagcaga                                           27

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ccactctccc ctcgcaggaa gagcag                                            26

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggtagcaggg cctcaccgtg gagcaga                                           27

<210> SEQ ID NO 176
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
atcagttccc ctcgcaggaa gagcag                                            26

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
cggaataggg cctcaccgtg gagcaga                                         27

<210> SEQ ID NO 178
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tctgagtccc ctcgcaggaa gagcag                                          26

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
caatcatcga tgtactagtg tggtccag                                        28

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ggatgtcggc gaaggagtcg aact                                            24

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
atgagctatg tatggctggc gcagagc                                         27

<210> SEQ ID NO 182
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aggaatgtat gatcccgtcc accagc                                          26

<210> SEQ ID NO 183
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
caaaagtatg tatggctggc gcagagc                                27

<210> SEQ ID NO 184
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tagttggtat gatcccgtcc accagc                                 26

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
caccggtatg tatggctggc gcagagc                                27

<210> SEQ ID NO 186
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
atcgtggtat gatcccgtcc accagc                                 26

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ctagcttatg tatggctggc gcagagc                                27

<210> SEQ ID NO 188
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tctgaggtat gatcccgtcc accagc                                 26

<210> SEQ ID NO 189
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gtccccttcc ttccgatcta atctc				25

<210> SEQ ID NO 190
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgcacgcagt caaataatgg tacga				25

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cgatgtcatc aagctgccca acatccc				27

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tggtcatcgg tcatccatgc cttctcgt				28

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
atcacgcatc aagctgccca acatccc				27

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gcctaatcgg tcatccatgc cttctcgt				28

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
agttcccatc aagctgccca acatccc     27

<210> SEQ ID NO 196
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
ctctactcgg tcatccatgc cttctcgt     28

<210> SEQ ID NO 197
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ctataccatc aagctgccca acatccc     27

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
tctgagtcgg tcatccatgc cttctcgt     28

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
aatgtgccag ttccatgtgg gtgt     24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
gcaggccata atgctgtcgg gtat     24

<210> SEQ ID NO 201
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
atgagcatgg aaagttattc ttctgagaa                                    29

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
aggaattatg aagaggatct aacagagag                                    30

<210> SEQ ID NO 203
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
caaaagatgg aaagttattc ttctgagaa                                    29

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
tagttgtatg aagaggatct aacagagag                                    30

<210> SEQ ID NO 205
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
tcggcaatgg aaagttattc ttctgagaa                                    29

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gaatgatatg aagaggatct aacagagag                                    30

<210> SEQ ID NO 207
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctatacatgg aaagttattc ttctgagaa                                    29

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
tctgagtatg aagaggatct taacagagag                                    30

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
atgtcggcca gcaacaacaa                                               20

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
agtagtgtat ccatcctcgt gcat                                          24

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
aatagcccat tcaccttgtt caaca                                         25

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
cagccataga ccatagtact acaccac                                       27

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tcatcctcga acactaggct gaag                                          24

```
<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tactactcgc agcgcatcac tca                                              23

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
attgaacggt gtcacttcag acca                                             24

<210> SEQ ID NO 216
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tattgagctg atcagctgaa cagaac                                           26

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
actcgctgga actatccatc ttggc                                            25

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aagcgctcga cggcgtgga                                                   19

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ctccgacatc ctcgtcgagg ct                                               22
```

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
gattcaccaa caagacgcag ca                                              22

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
aaccacctct tccgccacga g                                               21

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
acgcagcacc tgctcaagca ac                                              22

<210> SEQ ID NO 223
<211> LENGTH: 5
<212> TYPE: PRT
<213> ORGANISM: Unknown
<220> FEATURE:
<223> OTHER INFORMATION: Description of Unknown: Wheat, Rice or Maize sequence
<220> FEATURE:
<221> NAME/KEY: MOD_RES
<222> LOCATION: (2)..(2)
<223> OTHER INFORMATION: His or Tyr

<400> SEQUENCE: 223

Thr Xaa Gly Val Gln
1               5

<210> SEQ ID NO 224
<211> LENGTH: 15
<212> TYPE: DNA
<213> ORGANISM: Unknown
<220> FEATURE:
<223> OTHER INFORMATION: Description of Unknown: Wheat, Rice or Maize sequence

<400> SEQUENCE: 224
acccacggcg tgcag                                                      15

<210> SEQ ID NO 225
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 225

```
gccgttcctg gttgatatta acaacctcga cggcagcttc gtg                          43
```

<210> SEQ ID NO 226
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

```
gccgttcctg gttgacatca acaacctcga cggcagcttc gtg                          43
```

<210> SEQ ID NO 227
<211> LENGTH: 5
<212> TYPE: PRT
<213> ORGANISM: Oryza sativa

<400> SEQUENCE: 227

Asp Gln Pro Ala Ser
1               5

<210> SEQ ID NO 228
<211> LENGTH: 15
<212> TYPE: DNA
<213> ORGANISM: Oryza sativa

<400> SEQUENCE: 228

```
gaccagccag cgtcg                                                         15
```

<210> SEQ ID NO 229
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229

```
gatcagccag cgtcg                                                         15
```

<210> SEQ ID NO 230
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230

```
gactagccag cgtcg                                                         15
```

<210> SEQ ID NO 231
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231

```
gaccagtcag cgtcg                                                         15
```

<210> SEQ ID NO 232
<211> LENGTH: 15

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gaccagctag cgtcg                                                    15

<210> SEQ ID NO 233
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gattagccag cgtcg                                                    15

<210> SEQ ID NO 234
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gaccagttag cgtcg                                                    15
```